(12) United States Patent
Watkins et al.

(10) Patent No.: US 11,117,893 B2
(45) Date of Patent: Sep. 14, 2021

(54) METHODS FOR PREPARATION OF SUBSTITUTED PYRIDINES AND RELATED NOVEL COMPOUNDS

(71) Applicants: Edmond Blake Watkins, Jackson, TN (US); Dilipkumar Uredi, Jackson, TN (US); Damoder Reddy Motati, Decatur, GA (US)

(72) Inventors: Edmond Blake Watkins, Jackson, TN (US); Dilipkumar Uredi, Jackson, TN (US); Damoder Reddy Motati, Decatur, GA (US)

(73) Assignee: Union University, Jackson, TN (US)

( * ) Notice: Subject to any disclaimer, the term of this patent is extended or adjusted under 35 U.S.C. 154(b) by 0 days.

(21) Appl. No.: 16/580,138

(22) Filed: Sep. 24, 2019

(65) Prior Publication Data

US 2020/0095245 A1 Mar. 26, 2020

Related U.S. Application Data

(60) Provisional application No. 62/735,517, filed on Sep. 24, 2018.

(51) Int. Cl.

| | | |
|---|---|---|
| C07D 471/04 | (2006.01) |
| C07D 471/14 | (2006.01) |
| C07D 491/048 | (2006.01) |
| C07D 495/04 | (2006.01) |
| C07D 409/06 | (2006.01) |
| C07D 405/04 | (2006.01) |
| C07D 213/06 | (2006.01) |
| C07D 217/04 | (2006.01) |
| C07D 401/04 | (2006.01) |

(52) U.S. Cl.
CPC ......... *C07D 471/04* (2013.01); *C07D 213/06* (2013.01); *C07D 217/04* (2013.01); *C07D 401/04* (2013.01); *C07D 405/04* (2013.01); *C07D 409/06* (2013.01); *C07D 471/14* (2013.01); *C07D 491/048* (2013.01); *C07D 495/04* (2013.01)

(58) Field of Classification Search
None
See application file for complete search history.

(56) References Cited

FOREIGN PATENT DOCUMENTS

CN 108358834 A 8/2018

OTHER PUBLICATIONS

Wei et al, Organic Letters, 17(24), 5974-5977 (Year: 2015).*
Song et al, Organic Letters, 15(13), 3274-3277 (Year: 2013).*
Engelbert Ciganek et al. Intramolecular diels-alder reactions. 4 . Additions to naphthalene. Journal of Heterocyclic Chemistry 1994, 31 (5) , 1251-1257.

* cited by examiner

*Primary Examiner* — Zinna Northington Davis
(74) *Attorney, Agent, or Firm* — JWIP & Patent Services, LLC; Jacob G. Weintraub, Esq.

(57) ABSTRACT

The present invention relates to novel methods of preparation of substituted pyridines and the compounds produced therefrom. In particular, the present invention provides efficient methods for the construction of diversely substituted pyridines, with varying substitution patterns under simple and metal-free conditions with high atom- and pot-economy and excellent functional group tolerance, and which are useful for the synthesis of natural products.

11 Claims, No Drawings

METHODS FOR PREPARATION OF SUBSTITUTED PYRIDINES AND RELATED NOVEL COMPOUNDS

RELATED APPLICATIONS

This application claims priority to U.S. Provisional Patent Application No. 62/735,517, filed on Sep. 24, 2018; the entirety of which is incorporated herein by reference.

BACKGROUND OF THE INVENTION

Pyridines are scaffolds found in numerous natural products and biologically active molecules, and are ubiquitous in pharmaceuticals, agrochemicals and in advanced organic materials such as OLEDs and fluorescent sensors. Pyridine and its derivatives have significant applications as organic bases, ligands, catalysts and directing groups in C—H activation reactions. Further, fused-pyridine heterocycles, including carbolines, are also ubiquitous structural motifs prevalent in natural products, pharmaceuticals, agrochemicals, materials and ligand scaffolds among other examples; thus highlighting the significance of such structures. Among the isomeric α—, β-, γ—, and δ-carbolines, the most abundant framework in nature is β-carboline.

β-Carbolines possess a wide array of pharmacological properties, including anti-inflammatory, anti-Alzheimer, antimalarial, antibacterial, antitumor, anti-HIV activities and others. The structural similarity of $C_1$-substituted β-carboline alkaloids with 2-substituted pyridines revealed their potential as directing groups for C—H functionalization reactions. Hence, the development of efficient methodologies for the construction of the carboline skeleton has attracted substantial attention in synthetic chemistry. The augmentation of processes that tease new reactivity out of easily accessible precursors continues to spur the chemistry community toward pioneering methodologies that provide rapid access to nitrogen-containing heterocycles.

Traditional methods of pyridine synthesis (Chichibabin and Hantzsch reactions) involve condensation of carbonyl compounds and amines. More recently, transition metal-catalyzed cross couplings, ring-closing metathesis, cycloadditions, radical reactions and microwave-assisted reactions have been developed for the synthesis of pyridines. In fact, these reported pyridine synthetic methods, which require metal catalysts or multi-step synthetic starting materials, more importantly lack diversity in the substitution pattern achieved through the process.

While the Bischler-Napieralski, Pictet-Spengler and Graebe-Ullmann reactions are the conventional approaches for the synthesis of β- or γ-carboline derivatives, in recent years several new protocols for the synthesis of β- or γ-carboline frameworks have been developed using a range of starting materials and metal catalysts. Examples include the cyclization/iminoannulation of acetylene derivatives with pre-functionalized indoles; metal-catalyzed cyclization/functionalization of various precursors prepared in multiple steps. In this regard, while much effort has been devoted to the development of metal-catalyzed cyclizations, alternative and/or complementary methods using more practical, environmentally benign and metal-free conditions are lacking.

Reactions employing mild and metal-free protocols are ideal because they circumvent the use of toxic metals, excess oxidant/additive, as well as the preconstruction of starting materials in multiple steps in multi-phase type additions. Mild and metal-free reactions have a significant impact in organic synthesis due to their greener and environmentally benign properties, with the potential to reduce cost as well as reduce waste generation. This makes metal-free synthesis of complex heterocyclic scaffolds a highly attractive strategy as an atom-economic and environmentally benign process.

Despite progress, there is still a need to develop an efficient method for the construction of diversely substituted pyridines, with varying substitution patterns under simple and metal-free conditions with high atom- and pot-economy and excellent functional group tolerance, and which may be applicable to the total synthesis of biologically important natural products.

SUMMARY OF THE INVENTION

Accordingly, the present invention is directed to novel methods of preparation of substituted pyridines and the compounds produced therefrom. In particular, the present invention provides efficient methods for the construction of diversely substituted pyridines, with varying substitution patterns under simple and metal-free conditions with high atom- and pot-economy and excellent functional group tolerance, and which are useful for the synthesis of natural products.

As such, one aspect of the invention provides a method of preparation of a substituted pyridine of formula I:

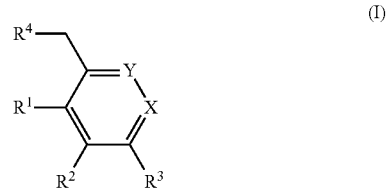

(I)

wherein
$R^1$ is selected from the group consisting of H, ($C_1$-$C_4$) alkyl (e.g., methyl), ($C_1$-$C_{10}$)alkenyl (e.g., ethylene), phenyl, indolylalkyl (e.g., 2-hydroxy-2-(1-methyl-1H-indol-3-yl)ethyl), aryl (e.g., phenyl or napthyl), and heteroaryl (e.g., thiophenyl or furanyl), each of which may be optionally substituted with 1 to 5 substituents selected from the group consisting of ($C_1$-$C_4$)haloalkyl (e.g., $CF_3$), ($C_1$-$C_4$)alkoxy (e.g., —$OCH_3$), —CN, halogen (e.g., F, Br, Cl), $NO_2$, ($C_1$-$C_4$)alkyl (e.g., methyl) and OH;

$R^2$ is selected from the group consisting of H and ($C_1$-$C_4$)alkyl (e.g., methyl);

or $R^1$ and $R^2$ may be taken together with the carbons to which they are attached to form a ring structure selected from the group consisting of cycloalkyl, heterocyclyl, aryl, and heteroaryl (e.g., each of which monocyclic or polycyclic that may be fused or bridged), each of which may be optionally substituted with 1 to 3 substituents selected from the group consisting of ($C_1$-$C_4$)haloalkyl (e.g., $CF_3$), ($C_1$-$C_4$)alkoxy (e.g., —$OCH_3$), —CN, halogen (e.g., Br), $NO_2$, ($C_1$-$C_4$)alkyl (e.g., methyl), ($C_1$-$C_4$)alkenyl (e.g., propenyl), and OH;

$R^3$ is selected from the group consisting of H, ($C_1$-$C_4$) alkyl (e.g., methyl), ($C_1$-$C_6$)alkylcarbonyl (e.g., 3-methylbutanoyl), and benzyl;

$R^4$ is selected from the group consisting of H, —$CH_2$, ($C_1$-$C_{10}$)alkyl (e.g., straight or branched ($C_1$-$C_{10}$) alkyl (e.g., $CH_3$)), ($C_1$-$C_{10}$)alkenyl (e.g., straight or branched (C₁-C₁₀)alkenyl (e.g., heptenyl or octenyl)), each of which is optionally substituted with 1 to 4 substituents selected from the group consisting of (C₁-C₄)alkyl (e.g., methyl), halogen (e.g., Br), —CN, —C(O)O—(C₁-C₄)alkyl (e.g., —C(O)OCH₃), —O—(C₁-C₄)alkyl (e.g., —OCH₃); and X and Y are independently selected from N and CR₅, wherein R₅ is H or (C₁-C₄)alkyl (e.g., CH₃), and wherein one of X or Y is N and the other is CR₅, comprising the step of single phase addition of a substituted or unsubstituted α,β-unsaturated carbonyl to a substituted or unsubstituted propargyl amine under metal-free conditions (MFC).

Another aspect of the present invention provides a compound of formula (I)

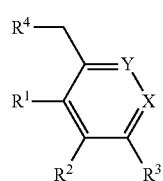

(I)

wherein

R¹ is selected from the group consisting of H, (C₁-C₄) alkyl (e.g., methyl), (C₁-C₁₀)alkenyl (e.g., ethylene), phenyl, indolylalkyl (e.g., 2-hydroxy-2-(1-methyl-1H-indol-3-yl) ethyl), aryl (e.g., phenyl or napthyl), and heteroaryl (e.g., thiophenyl or furanyl), each of which may be optionally substituted with 1 to 5 substituents selected from the group consisting of (C₁-C₄)haloalkyl (e.g., CF₃), (C₁-C₄)alkoxy (e.g., —OCH₃), —CN, halogen (e.g., F, Br, Cl), NO₂, (C₁-C₄)alkyl (e.g., methyl) and OH;

R² is selected from the group consisting of H and (C₁-C₄)alkyl (e.g., methyl); or R¹ and R² may be taken together with the carbons to which they are attached to form a ring structure selected from the group consisting of cycloalkyl, heterocyclyl, aryl, and heteroaryl (e.g., each of which monocyclic or polycyclic that may be fused or bridged), each of which may be optionally substituted with 1 to 3 substituents selected from the group consisting of (C₁-C₄)haloalkyl (e.g., CF₃), (C₁-C₄)alkoxy (e.g., —OCH₃), —CN, halogen (e.g., Br), NO₂, (C₁-C₄)alkyl (e.g., methyl), (C₁-C₄)alkenyl (e.g., propenyl), and OH;

R³ is selected from the group consisting of H, (C₁-C₄) alkyl (e.g., methyl), (C₁-C₆)alkylcarbonyl (e.g., 3-methylbutanoyl), and benzyl;

R⁴ is selected from the group consisting of H, —CH₂, (C₁-C₁₀)alkyl (e.g., straight or branched (C₁-C₁₀)alkyl (e.g., CH₃)), (C₁-C₁₀)alkenyl (e.g., straight or branched (C₁-C₁₀) alkenyl (e.g., heptenyl or octenyl)), each of which is optionally substituted with 1 to 4 substituents selected from the group consisting of (C₁-C₄)alkyl (e.g., methyl), halogen (e.g., Br), —CN, —C(O)O—(C₁-C₄)alkyl (e.g., —C(O)OCH₃), —O—(C₁-C₄)alkyl (e.g., —OCH₃); and X and Y are independently selected from N and CR₅, wherein R₅ is H or (C₁-C₄)alkyl (e.g., CH₃), and wherein one of X or Y is N and the other is CR₅.

with the proviso that the compound of formula (I) is not:

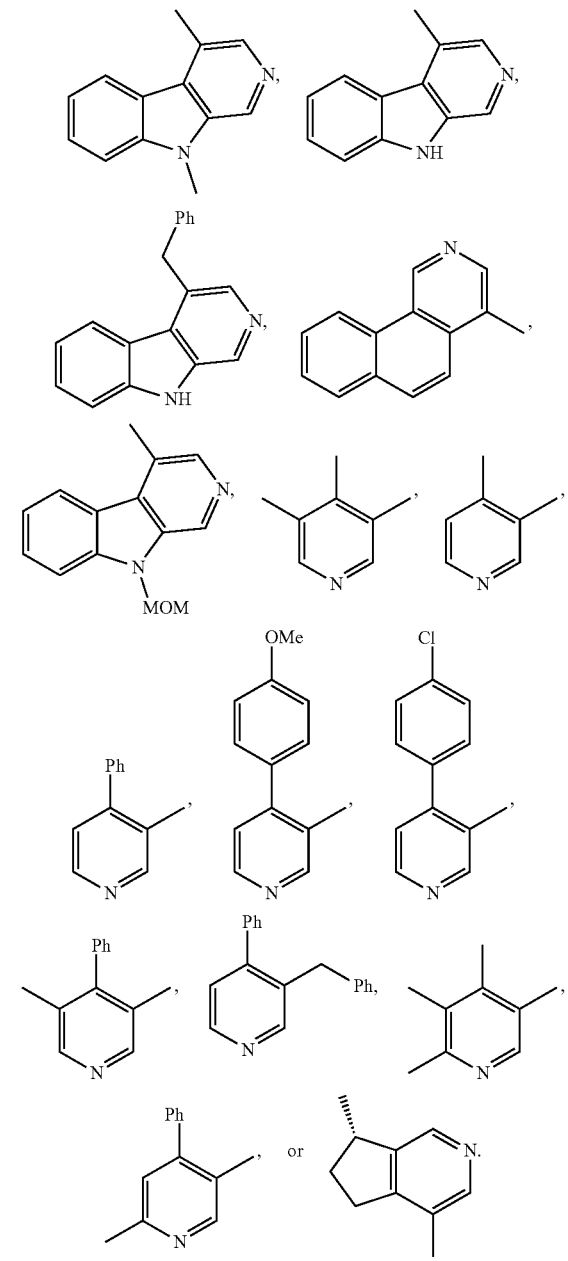

Another aspect of the present invention provides a compound selected from the following:

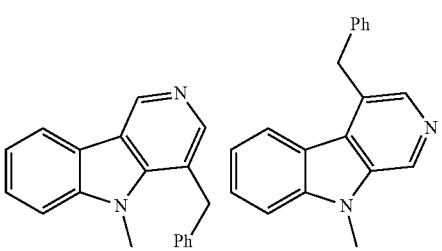

-continued
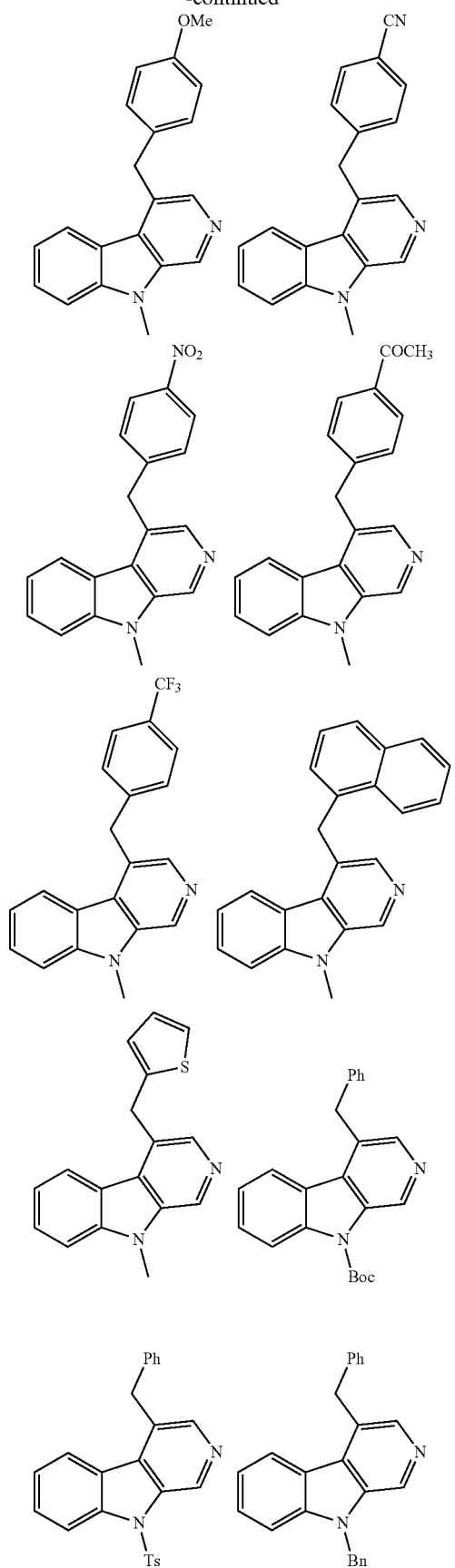
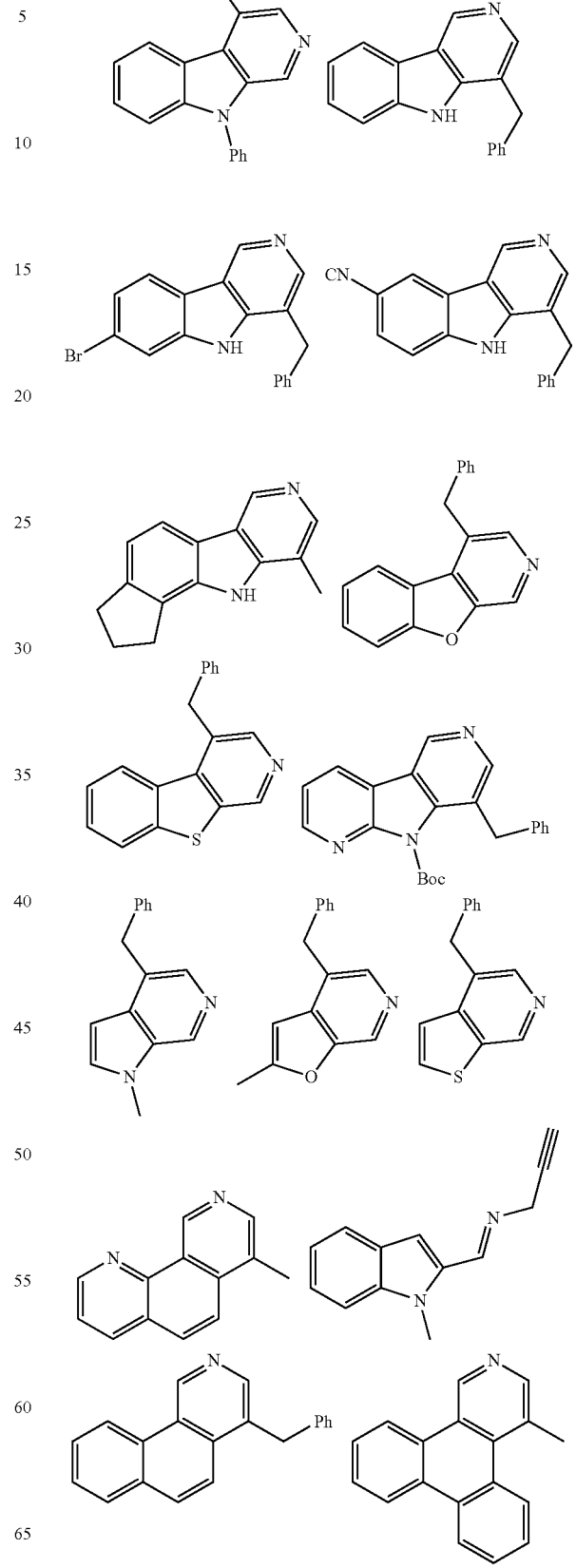

-continued
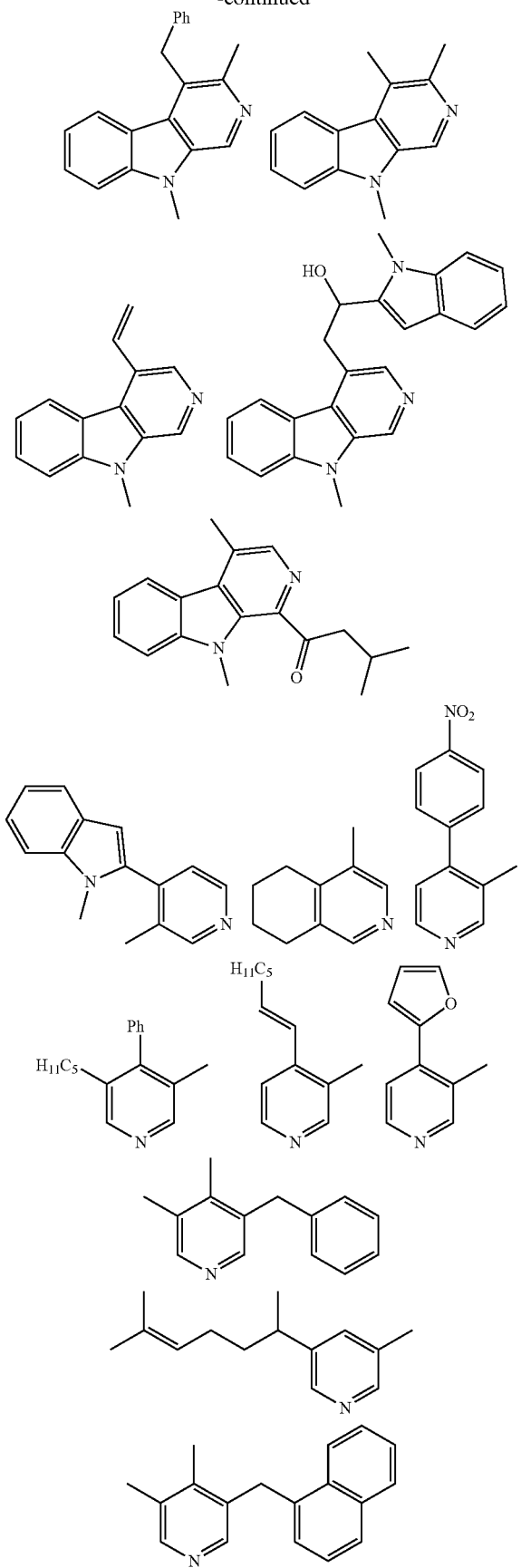
-continued
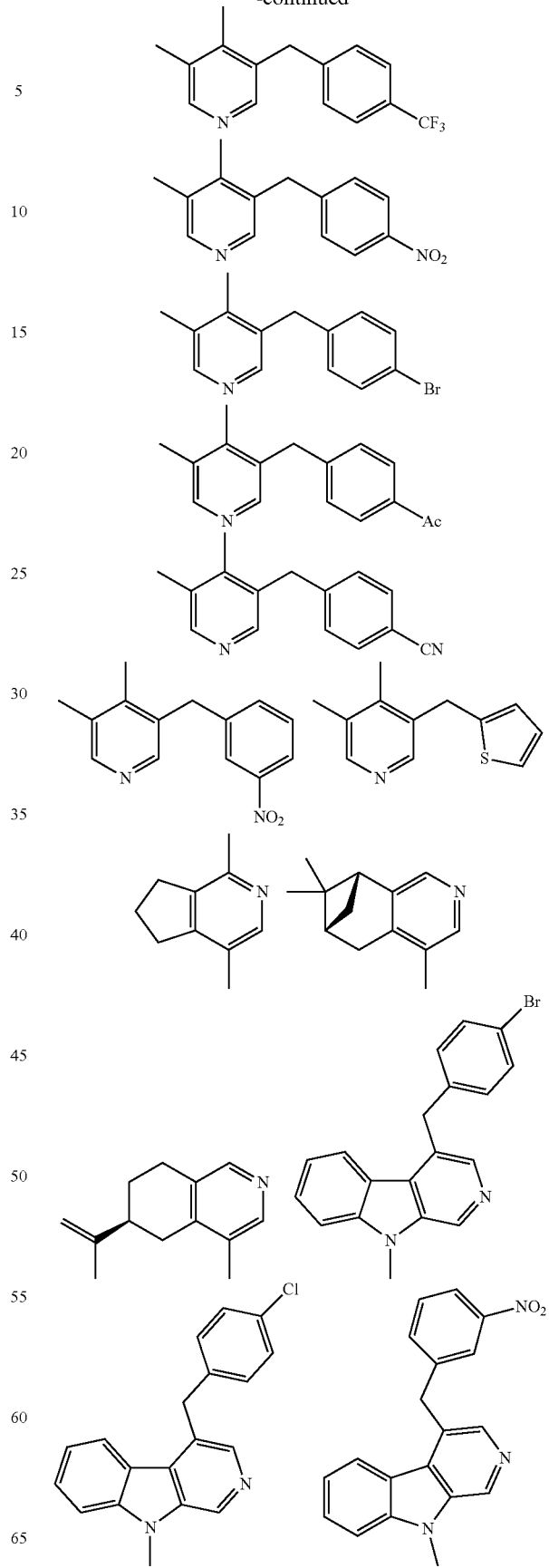

-continued

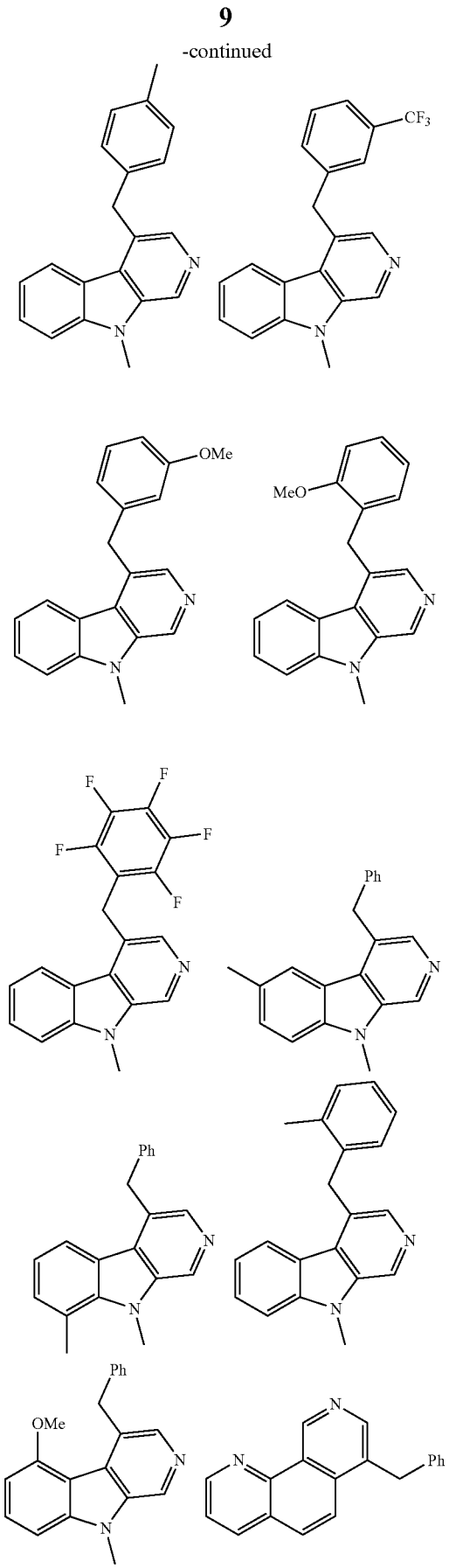

-continued

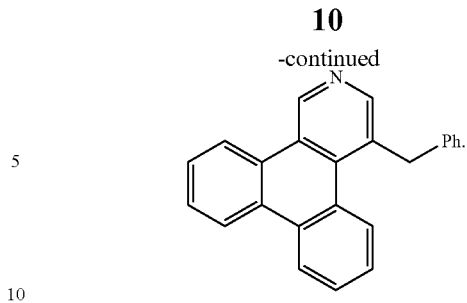

DETAILED DESCRIPTION OF THE INVENTION

The present invention provides a single-phase synthesis of diversely substituted pyridines from readily available α,β-unsaturated carbonyl compounds and propargylic amines. This provides broad substrate scope and allows access to multi-substituted pyridines with select control of the substitution pattern under mild and metal-free conditions. The methodology provided herein provides a novel strategy for the synthesis of substituted pyridines, β-carbolines, γ-carbolines, and fused aromatic aza heterocycles. The present protocol has a broad substrate scope and is applicable to late stage derivatizations of natural products and key intermediates.

As such, the present invention is directed to novel methods of preparation of substituted pyridines and the compounds produced therefrom. In particular, the present invention provides efficient methods for the construction of diversely substituted pyridines, with varying substitution patterns under simple and metal-free conditions with high atom- and pot-economy and excellent functional group tolerance, and which are useful for the synthesis of natural products.

The present invention, including methods and the compounds produced therefrom will be described with reference to the following definitions that, for convenience, are set forth below. Unless otherwise specified, the below terms used herein are defined as follows:

I. Definitions

As used herein, the term "a," "an," "the" and similar terms used in the context of the present invention (especially in the context of the claims) are to be construed to cover both the singular and plural unless otherwise indicated herein or clearly contradicted by the context.

As used herein, "alkyl" refers to a linear or branched saturated or unsaturated aliphatic $C_1$-$C_6$ hydrocarbon, unless some other number of carbon atoms is specified. Unsaturation in the form of a double (i.e., an "alkenyl") or triple (i.e., an "alkynyl") carbon-carbon bond may be internal or terminally located and, in the case of a double bond, both cis and trans isomers are included. In one example, an optionally substituted alkyl can be independently substituted with one or more substituents selected from oxo, ($C_3$-$C_6$)cycloalkyloxy, ($C_1$-$C_4$)alkylthio, ($C_3$-$C_6$)cycloalkylthio-, —C(O)NH$_2$, —C(O)NH($C_1$-$C_4$)alkyl, —C(O)N[($C_1$-$C_4$)alkyl($C_1$-$C_4$)alkyl], ($C_1$-$C_4$ alkyl)-C(O)—, ($C_1$-$C_4$)alkylsulfonyl-, —S(O)$_2$NH$_2$, —S(O)$_2$NH($C_1$-$C_4$)alkyl, —S(O)$_2$N[($C_1$-$C_4$)alkyl($C_1$-$C_4$)alkyl], ($C_1$-$C_4$)haloalkyl (e.g., $CF_3$), ($C_1$-$C_4$) alkoxy (e.g., —OCH$_3$), —CN, halogen (e.g., F, Br, Cl), NO$_2$, and OH. Examples of alkyl groups include, but are not limited to, methyl, ethyl, n-propyl, isopropyl, t-butyl, n-pentyl, n-hexyl, isobutyl, neopentyl, cis- and trans-2-butenyl, isobutenyl and propargyl. $C_1$-$C_4$ alkyl is the subset of alkyl limited to a total of up to 4 carbon atoms.

In each case in which a size range for the number of atoms in a ring or chain is disclosed, all subsets are disclosed. Thus, $C_x$-$C_y$ includes all subsets, e.g., $C_1$-$C_4$ includes $C_1$-$C_2$, $C_2$-$C_4$, and $C_1$-$C_3$ as well as $C_1$, $C_2$, $C_3$ and $C_4$.

As used herein "alkoxy" refers to an alkyl-O— group wherein alkyl is as defined above. $C_1$-$C_6$ alkoxy is the subset of alkyl-O— where the subset of alkyl is limited to a total of up to 6 carbon atoms. Examples of alkoxy groups include methoxy, trifluoromethoxy, ethoxy, trifluoroethoxy, and propoxy.

As used herein, "alkylthio" refers to an alkyl—S— group wherein alkyl is as defined above. $C_1$-$C_6$ alkylthio is the subset of alkyl—S— where the subset of alkyl is limited to a total of up to 6 carbon atoms.

As used herein, "alkylamino" refers to alkyl—NH— wherein alkyl is as defined above.

As used herein, the term "aryl" means a mono- or polycyclic hydrocarbon, containing from 6 to 15 carbon atoms, in which at least one ring is aromatic. Examples of suitable aryl groups include, but are not limited to, phenyl, tolyl, anthracenyl, fluorenyl, indenyl, azulenyl, and naphthyl 1H-phenalenyl as well as benzo-fused carbocyclic moieties such as 5,6,7,8-tetrahydronaphthyl. Aryl groups included in compounds of this invention may be optionally substituted with one or more substituents. In one embodiment, the aryl group is a monocyclic ring, wherein the ring comprises 6 carbon atoms. An optionally substituted aryl can be independently substituted with one or more substituents selected from ($C_1$-$C_4$)haloalkyl (e.g., $CF_3$), ($C_1$-$C_4$)alkoxy (e.g., —$OCH_3$), —CN, halogen (e.g., Br), $NO_2$, ($C_1$-$C_4$)alkyl (e.g., methyl), ($C_1$-$C_4$)alkenyl (e.g., propenyl), OH, ($C_1$-$C_4$)alkylthio, ($C_3$-$C_7$)cycloalkylthio, ($C_3$-$C_7$)cycloalkyloxy, aryloxy, ($C_1$-$C_4$)alkoxy($C_1$-$C_4$)alkyloxy, hetero($C_3$-$C_7$)cycloalkyloxy, heteroaryloxy, —OC(O)$R_a$, —OC(O)NH$R_a$, —OC(O)N($R_a$)($R_b$), —S(O)$R_a$, —NH$R_a$, —N($R_a$)($R_b$), —NHC(O)$R_a$, —N($R_a$)C(O)$R_b$, —NHC(O)O$R_a$, —N($R_a$)C(O)O$R_b$, —N($R_a$)—C(O)—NH($R_b$), —N($R_a$)—C(O)—N ($R_b$)$_2$, —C(O)$NH_2$, —C(O)NH$R_a$, —C(O)N($R_a$)($R_b$), —$CO_2$H, —$CO_2$$R_a$, —COR$_a$ and R$_c$ wherein R$_a$, R$_b$ and R$_c$ are independently chosen from ($C_1$-$C_6$)alkyl, ($C_1$-$C_4$)alkoxy ($C_1$-$C_4$)alkyl, —$CH_2CH_2OH$, —$CH_2CH_2OMe$, ($C_3$-$C_7$)cycloalkyl, ($C_3$-$C_7$)cycloalkyl($C_1$-$C_4$)alkyl, aryl, arylalkyl, heteroaryl, heteroarylalkyl, hetero($C_3$-$C_7$)cycloalkyl, and hetero($C_3$-$C_7$)cycloalkyl($C_1$-$C_4$)alkyl, each of which is optionally and independently substituted with up to three groups selected from halogen, ($C_1$-$C_6$)alkyl, ($C_3$-$C_7$)cycloalkyl, ($C_3$-$C_7$)cycloalkyloxy, ($C_3$-$C_7$)cycloalkylalkoxy, CN, $CHF_2$, $CF_3$, $CH_2CF_3$, NHMe, $NMe_2$, piperidinyl, morpholinyl, N—Me-piperazinyl, piperazinyl, $OCF_3$, $OCHF_2$, $OCH_2CF_3$, SMe, each of which are attached via carbon-carbon or carbon-nitrogen or carbon-oxygen single bonds, and none of which are substituted; or R$_a$ and R$_b$ taken together with the atom(s) to which they are attached form a 5-6 membered ring. In other cases, an optionally substituted aryl can be independently substituted with one or more substituents selected from halogen $CF_3$, CN, ($C_1$-$C_6$)alkyl, ($C_3$-$C_7$)cycloalkyl, ($C_1$-$C_4$)alkoxy, ($C_3$-$C_7$)cycloalkylthio, ($C_3$-$C_7$)cycloalkyloxy, hetero($C_3$-$C_7$)cycloalkyl, C(O)$NH_2$, —C(O)NH$R_a$, —C(O)N($R_a$)($R_b$) wherein R$_a$ and R$_b$ are defined as above. In further cases, an optionally substituted aryl can be independently substituted with one or more substituents selected from halogen $CF_3$, CN, ($C_1$-$C_6$)alkyl, ($C_3$-$C_7$)cycloalkyl, ($C_3$-$C_7$)cycloalkyloxy, and hetero($C_3$-$C_7$)cycloalkyl.

As used herein "cycloalkyl" is a $C_3$-$C_8$ cyclic non-aromatic hydrocarbon which may contain a single double bond. An optionally substituted cycloalkyl can be independently substituted with one or more substituents selected from oxo, —($C_3$-$C_7$)cycloalkyl, ($C_3$-$C_7$)cycloalkylalkyl, ($C_3$-$C_7$)cycloalkyloxy, ($C_1$-$C_4$)alkylthio, ($C_3$-$C_6$)cycloalkylthio-, —C(O)$NH_2$, —C(O)NH($C_1$-$C_4$)alkyl, —C(O)N[($C_1$-$C_4$)alkyl($C_1$-$C_4$)alkyl], ($C_1$-$C_4$ alkyl)-C(O)—, ($C_1$-$C_4$)alkylsulfonyl-, —S(O)$_2NH_2$, —S(O)$_2$NH($C_1$-$C_4$)alkyl, —S(O)$_2$N[($C_1$-$C_4$)alkyl($C_1$-$C_4$)alkyl], ($C_1$-$C_4$)haloalkyl (e.g., $CF_3$), ($C_1$-$C_4$)alkoxy (e.g., —$OCH_3$), —CN, halogen (e.g., Br), $NO_2$, ($C_1$-$C_6$)alkyl (e.g., methyl), ($C_1$-$C_4$)alkenyl (e.g., propenyl), and OH. In other cases, an optionally substituted cycloalkyl can be independently substituted with one or more substituents selected from F, oxo, ($C_1$-$C_4$)alkoxy, ($C_3$-$C_7$)cycloalkyl, —C(O)NH($C_1$-$C_4$)alkyl, —C(O)N[($C_1$-$C_4$)alkyl($C_1$-$C_4$)alkyl], ($C_1$-$C_4$ alkyl)-C(O)—, ($C_1$-$C_4$)alkylsulfonyl-, —S(O)$_2$NH($C_1$-$C_4$)alkyl, —S(O)$_2$N[($C_1$-$C_4$)alkyl($C_1$-$C_4$)alkyl]. In further cases, an optionally substituted cycloalkyl can be independently substituted with one substituent selected from oxo, OH, ($C_1$-$C_6$)alkyl, ($C_1$-$C_4$)alkoxy, ($C_3$-$C_7$)cycloalkylalkyl, ($C_3$-$C_7$)cycloalkyloxy, ($C_1$-$C_4$)alkylthio, ($C_3$-$C_6$)cycloalkylthio-, —C(O)$NH_2$, —C(O)NH($C_1$-$C_4$)alkyl, —C(O)N[($C_1$-$C_4$)alkyl($C_1$-$C_4$)alkyl], ($C_1$-$C_4$ alkyl)-C(O)—, ($C_1$-$C_4$)alkylsulfonyl-, —S(O)$_2NH_2$, —S(O)$_2$NH($C_1$-$C_4$)alkyl, —S(O)$_2$N[($C_1$-$C_4$)alkyl ($C_1$-$C_4$)alkyl]. Examples of cycloalkyl groups include cyclopropyl, cyclobutyl, cyclopentyl, cyclohexyl, cyclopentenyl and cyclohexenyl.

As used herein, "halogen" refers to F, Cl, Br or I. In particular embodiments, halogens are F, Cl and Br.

As used herein, the term "halo-substituted alkyl" or "haloalkyl" refers to an alkyl as defined herein which is substituted by one or more halogen atoms, or halo groups as defined herein. The haloalkyl can be monohaloalkyl, dihaloalkyl, polyhaloalkyl, or perhaloalkyl. For example, a monohaloalkyl contains one iodo, bromo, chloro or fluoro within the alkyl group. For multiple substituted haloalkyls, the halo atoms may be the same or a combination of different halo groups within the alkyl. Typically the polyhaloalkyl contains up to 6, or 4, or 3, or 2 halo groups. In a preferred embodiment, halo-substituted alkyl groups have about 1 to 6 carbons, or 1-3 carbons. Non-limiting examples of haloalkyl include fluoromethyl, difluoromethyl, trifluoromethyl, chloromethyl, dichloromethyl, trichloromethyl, pentafluoroethyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms.

As used herein, the term "heteroaryl" refers to a 5-14 membered monocyclic- or polycyclic (e.g., bicyclic- or tricyclic-aromatic) ring system, having 1 to 8 heteroatoms selected from N, O or S. Typically, the heteroaryl is a 5-10 membered ring system (e.g., 5-7 membered monocycle or an 8-10 membered bicycle). A 5-7 membered monocyclic ring system preferably contains 1 to 3 heteroatoms each independently selected from O, N, or S. Exemplary heteroaryl groups include, but are not limited to indolyl, quinolonyl, 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, and 2-, 4-, or 5-pyrimidinyl.

As used herein, the term "heterocyclyl" means a monocyclic or a polycyclic, saturated or unsaturated, non-aromatic ring or ring system which typically contains 5- to 20-members and at least one heteroatom. A heterocyclic ring system can contain saturated ring(s) or unsaturated non-aromatic ring(s), or a mixture thereof. A 3- to 10-membered heterocycle can contain up to 5 heteroatoms, and a 7- to 20-membered heterocycle can contain up to 7 heteroatoms. Typically, a heterocycle has at least one carbon atom ring member. Each heteroatom is independently selected from nitrogen, which can be oxidized (e.g., N(O)) or quaternized, oxygen and sulfur, including sulfoxide and sulfone. The heterocycle may be attached via any heteroatom or carbon atom. Representative heterocycles include morpholinyl, thiomorpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl, and the like. A heteroatom may be substituted with a protecting group known to those of ordinary skill in the art, for example, a nitrogen atom may be substituted with a tert-butoxycarbonyl group. Furthermore, the heterocyclyl included in compounds of this invention may be optionally substituted with one or more substituents. Only stable isomers of such substituted heterocyclic groups are contemplated in this definition.

The language "metal-free conditions (MFC) is used herein to describe reactions conditions that are completely absent any and all transition metals.

As used herein the term "dose" is the amount of active pharmaceutical ingredient (API) administered to a subject. For example 1 mg means 1 mg of API was orally administered to each subject each day.

As used herein, the language "single phase" as used herein to describe a one pot synthetic scheme that does not require prior steps for pre-synthetic preparation of reaction intermediates. In particular, and for clarity, single phase addition of the present invention is distinct from prior methods that require a pre-step preparation of a phosphorus ylide.

As used herein, the terms "subject", and "patient" are used interchangeably. The terms "subject" and "patient" refer to an animal (e.g., a bird such as a chicken, quail or turkey) or a mammal including non-primates (e.g., a cow, pig, horse, sheep, rabbit, guinea pig, rat, cat, dog, and mouse) and primates (e.g., a monkey, chimpanzee and a human). In a particular embodiment, the subject is a human.

The terms "treating", "treatment", or the like, as used herein covers the treatment of a disease-state (i.e., disorder, symptom, or condition) in an animal, and includes at least one of: (i) preventing the disease-state from occurring, in particular, when such animal is predisposed to the disease-state but has not yet developed symptoms of having it; (ii) inhibiting the disease-state, i.e., partially or completely arresting its development; (iii) relieving the disease-state, i.e., causing regression of symptoms of the disease-state, or ameliorating a symptom of the disease-state; and (iv) reversal or regression of the disease-state, preferably eliminating or curing of the disease-state. In a preferred embodiment the terms "treating", "treatment", or the like, covers the treatment of a disease-state in an animal and includes at least one of (ii), (iii) and (iv) above. In a preferred embodiment of the present disclosure the animal is a mammal, preferably a primate, more preferably a human. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

The expression "therapeutically effective," as used herein, describes amounts or doses of a compound useful for improving or treating of a disorder or symptom, alone or in combination with other compounds/compositions, which are therapeutically effective for the purpose for which they were intended and achieve a therapeutic effect. In certain embodiments, to achieve a therapeutic effect, doses or amounts are provided by a well-regulated or well-designed regimen of administration. As such, therapeutically effective amounts or doses include amounts or doses that would not otherwise be therapeutically effective alone (i.e., in the absence of the combinations of the present invention), or what might otherwise be referred to as a subclinical dose. The amount needed to elicit the therapeutic response can be determined based on the age, health, size and sex of the patient. Optimal amounts can also be determined based on monitoring of the patient's response to treatment. Administration may be by any route, including, without limitation, parenteral, oral, sublingual, transdermal, topical, intranasal, intratracheal, or intrarectal. In certain embodiments, administration of the compounds may be by the oral route.

II. Methods of the Invention

The present invention provides a commercially viable mild method for the preparation of substituted or fused pyridines from single phase addition of a substituted or unsubstituted α,β-unsaturated carbonyl to a substituted or unsubstituted propargyl amine, under metal-free conditions (MFC). Additionally, the method does not suffer from electronic effects or regioselectivity issues like many of the previously existing methods. Moreover, it allows for broad substrate scope and functional group compatibility. Advantageously, the method is environmentally benign and high yielding, given the elimination of the harsh reaction conditions known for existing reactions.

One embodiment of the present invention provides a method of preparation of a substituted pyridine of formula I:

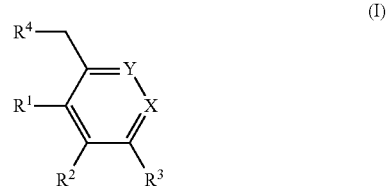

wherein
$R^1$ is selected from the group consisting of H, $(C_1-C_4)$ alkyl (e.g., methyl), $(C_1-C_{10})$alkenyl (e.g., ethylene), phenyl, indolylalkyl (e.g., 2-hydroxy-2-(1-methyl-1H-indol-3-yl)ethyl), aryl (e.g., phenyl or napthyl), and heteroaryl (e.g., thiophenyl or furanyl), each of which may be optionally substituted with 1 to 5 substituents (e.g., 1 to 3 substituents) selected from the group consisting of $(C_1-C_4)$haloalkyl (e.g., $CF_3$), $(C_1-C_4)$alkoxy (e.g., —$OCH_3$), —CN, halogen (e.g., F, Br, Cl), $NO_2$, $(C_1-C_4)$alkyl (e.g., methyl) and OH;
$R^2$ is selected from the group consisting of H and $(C_1-C_4)$alkyl (e.g., methyl);
or $R^1$ and $R^2$ may be taken together with the carbons to which they are attached to form a ring structure selected from the group consisting of cycloalkyl, heterocyclyl, aryl, and heteroaryl (e.g., each of which monocyclic or polycyclic that may be fused or bridged), each of which may be optionally substituted with 1 to 3 substituents selected from the group consisting of ($C_1$-$C_4$)haloalkyl (e.g., $CF_3$), ($C_1$-$C_4$)alkoxy (e.g., —$OCH_3$), —CN, halogen (e.g., Br), $NO_2$, ($C_1$-$C_4$)alkyl (e.g., methyl), ($C_1$-$C_4$)alkenyl (e.g., propenyl), and OH;

$R^3$ is selected from the group consisting of H, ($C_1$-$C_4$) alkyl (e.g., methyl), ($C_1$-$C_6$)alkylcarbonyl (e.g., 3-methylbutanoyl), and benzyl;

$R^4$ is selected from the group consisting of H, —$CH_2$, ($C_1$-$C_{10}$)alkyl (e.g., straight or branched ($C_1$-$C_{10}$) alkyl (e.g., $CH_3$)), ($C_1$-$C_{10}$)alkenyl (e.g., straight or branched ($C_1$-$C_{10}$)alkenyl (e.g., heptenyl or octenyl)), each of which is optionally substituted with 1 to 4 substituents selected from the group consisting of ($C_1$-$C_4$)alkyl (e.g., methyl), halogen (e.g., Br), —CN, —C(O)O—($C_1$-$C_4$)alkyl (e.g., —C(O)$OCH_3$), —O—($C_1$-$C_4$)alkyl (e.g., —$OCH_3$); and X and Y are independently selected from N and $CR_5$, wherein $R_5$ is H or ($C_1$-$C_4$)alkyl (e.g., $CH_3$), and wherein one of X or Y is N and the other is $CR_5$, comprising the step of single phase addition of a substituted or unsubstituted α,β-unsaturated carbonyl to a substituted or unsubstituted propargyl amine under metal-free conditions (MFC).

In certain embodiments of the present invention, $R^1$ and $R^2$ may be taken together with the pyridine to form a substituted or unsubstituted cyclic ring selected from the group consisting of an indole (e.g., forming a carboline with the pyridine ring), naphthalene, 1H-phenalene, thiophene, furan, imidazole, pyridine, anthracene, and quinolone.

In certain embodiments of the present invention, the metal-free conditions (MFC) comprises single phase addition in a polar solvent (e.g., such as N,N—dimethylformamide (DMF), ethyl acetate, or methanol) and a weak base (e.g., $K_2CO_3$, $NaHCO_3$, NaOAc, $CsCO_3$, $K_2HPO_4$, and DBU) under heating. In certain embodiments of the present invention, the metal-free conditions (MFC) comprise a mild base (e.g., $K_2CO_3$, $NaHCO_3$, NaOAc, $CsCO_3$, $K_2HPO_4$, and DBU) held at less than or equal to 100° C. (e.g., 80° C.). In certain embodiments of the present invention, the metal-free conditions (MFC) comprise a mild base (e.g., $K_2CO_3$, $NaHCO_3$, NaOAc, $CsCO_3$, $K_2HPO_4$, and DBU) held at less than or equal to 80° C.

In certain embodiments of the present invention, the metal-free conditions (MFC) comprises single phase addition in a polar solvent (e.g., such as N,N—dimethylformamide (DMF), ethyl acetate, or methanol) and a weak base (e.g., $K_2CO_3$, $NaHCO_3$, NaOAc, $CsCO_3$, $K_2HPO_4$, and DBU) under heating for less than 10 hours.

In certain embodiments of the present invention, the mild base is selected from the group consisting of $K_2CO_3$, $NaHCO_3$, NaOAc, $CsCO_3$, $K_2HPO_4$, and DBU. In a particular embodiment, the mild base is $NaHCO_3$.

In certain embodiments of the present invention, the method produces yields of greater than 80%. In certain embodiments, the mild base addition is performed in DMF.

In certain embodiments of the present invention, the substituted or unsubstituted α,β-unsaturated carbonyl is a compound of formula II:

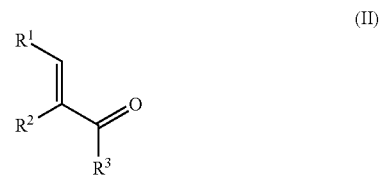

(II)

wherein $R^1$ is selected from the group consisting of H, ($C_1$-$C_4$) alkyl (e.g., methyl), ($C_1$-$C_{10}$)alkenyl (e.g., ethylene), phenyl, indolylalkyl (e.g., 2-hydroxy-2-(1-methyl-1H-indol-3-yl) ethyl), aryl (e.g., phenyl or napthyl), and heteroaryl (e.g., thiophenyl or furanyl), each of which may be optionally substituted with 1 to 5 substituents selected from the group consisting of ($C_1$-$C_4$)haloalkyl (e.g., $CF_3$), ($C_1$-$C_4$)alkoxy (e.g., —$OCH_3$), —CN, halogen (e.g., F, Br, Cl), $NO_2$, ($C_1$-$C_4$)alkyl (e.g., methyl) and OH;

$R^2$ is selected from the group consisting of H and ($C_1$-$C_4$)alkyl (e.g., methyl); or $R^1$ and $R^2$ may be taken together with the carbons to which they are attached to form a ring structure selected from the group consisting of cycloalkyl, heterocyclyl, aryl, and heteroaryl (e.g., each of which monocyclic or polycyclic that may be fused or bridged), each of which may be optionally substituted with 1 to 3 substituents selected from the group consisting of ($C_1$-$C_4$)haloalkyl (e.g., $CF_3$), ($C_1$-$C_4$)alkoxy (e.g., —$OCH_3$), —CN, halogen (e.g., Br), $NO_2$, ($C_1$-$C_4$)alkyl (e.g., methyl), ($C_1$-$C_4$)alkenyl (e.g., propenyl), and OH; and $R^3$ is selected from the group consisting of H, ($C_1$-$C_4$) alkyl (e.g., methyl), ($C_1$-$C_6$)alkylcarbonyl (e.g., 3-methylbutanoyl), and benzyl.

In certain embodiments of the present invention, the substituted or unsubstituted propargyl amine is a compound of formula III:

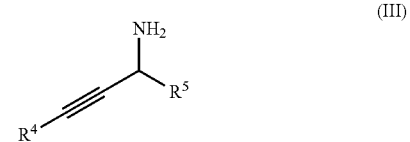

(III)

wherein $R^4$ is selected from the group consisting of H, —$CH_2$, ($C_1$-$C_{10}$)alkyl (e.g., straight or branched ($C_1$-$C_{10}$)alkyl (e.g., $CH_3$)), ($C_1$-$C_{10}$)alkenyl (e.g., straight or branched ($C_1$-$C_{10}$)alkenyl (e.g., heptenyl or octenyl)), each of which is optionally substituted with 1 to 4 substituents selected from the group consisting of ($C_1$-$C_4$)alkyl (e.g., methyl), halogen (e.g., Br), —CN, —C(O)O— ($C_1$-$C_4$)alkyl (e.g., —C(O)$OCH_3$), —O—($C_1$-$C_4$)alkyl (e.g., —$OCH_3$); and $R_5$ is H or ($C_1$-$C_4$)alkyl (e.g., $CH_3$).

In certain embodiments of the present invention, the compound of formula (I) is selected from a compound of formula (IV):

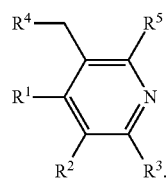
(IV)

In certain embodiments of the present invention, the compound of formula (I) is selected from a compound of formula (V):

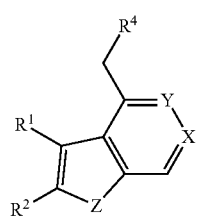
(V)

wherein
Z is selected from the group consisting of —O—, —S—, —N($R_6$)—, wherein $R_6$ is H, ($C_1$-$C_4$)alkyl (e.g., methyl), tosyl, benzyl, phenyl, tert-butyloxycarbonyl, In certain embodiments of the present invention, the compound of formula (I) is selected from a compound of formula (VI):

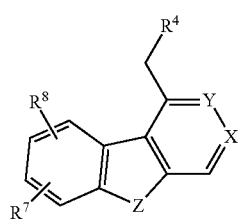
(VI)

wherein
Z is selected from the group consisting of —O—, —S—, —N($R_6$)—, wherein $R_6$ is H, ($C_1$-$C_4$)alkyl (e.g., methyl), tosyl, benzyl, phenyl, tert-butyloxycarbonyl; and
$R^7$ and $R^8$ are each independently selected from the group consisting of H, ($C_1$-$C_4$)haloalkyl (e.g., $CF_3$), ($C_1$-$C_4$)alkoxy (e.g., —$OCH_3$), —CN, halogen (e.g., Br), $NO_2$, ($C_1$-$C_4$) alkyl (e.g., methyl), ($C_1$-$C_4$)alkenyl (e.g., propenyl), and OH.

In certain embodiments of the present invention, the compound of formula (I) is selected from

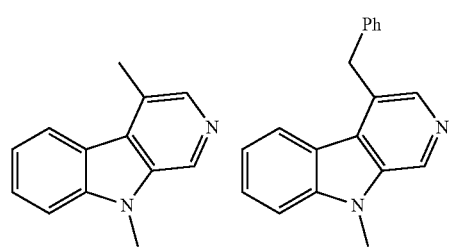

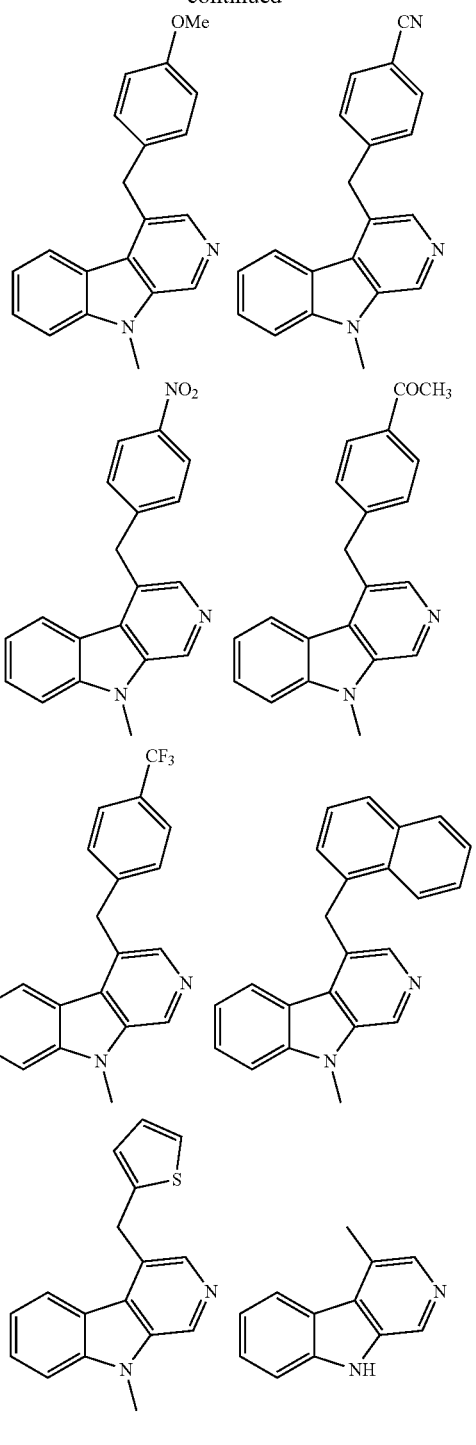

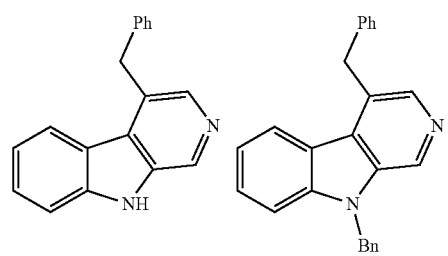

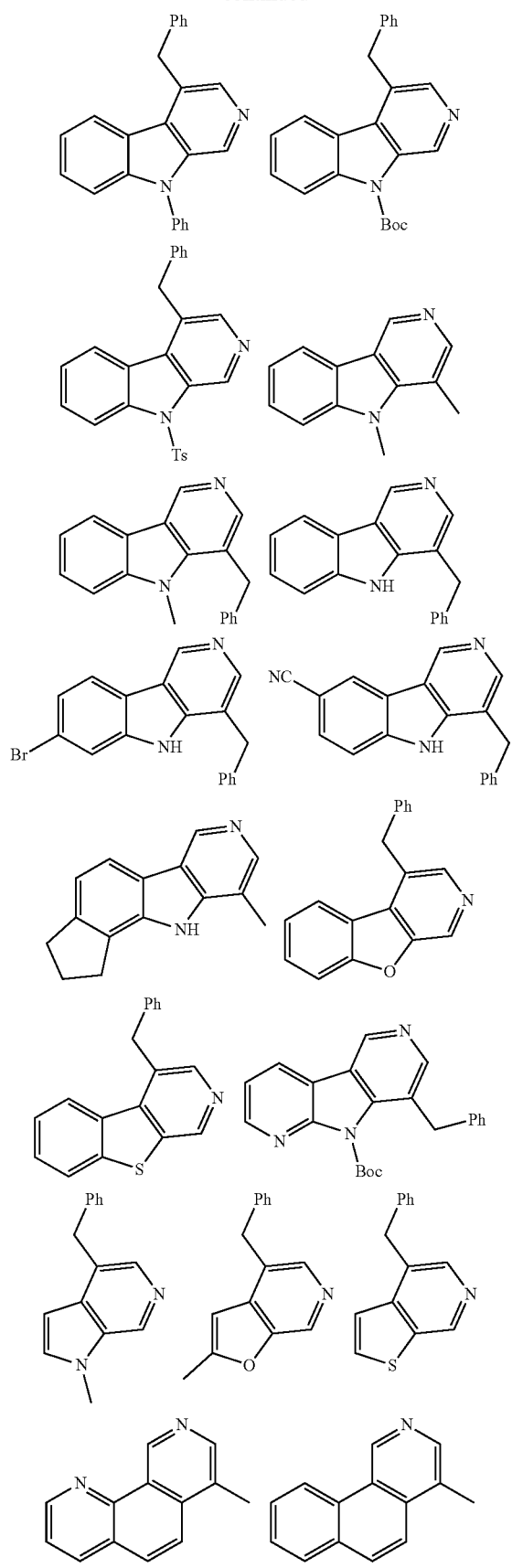
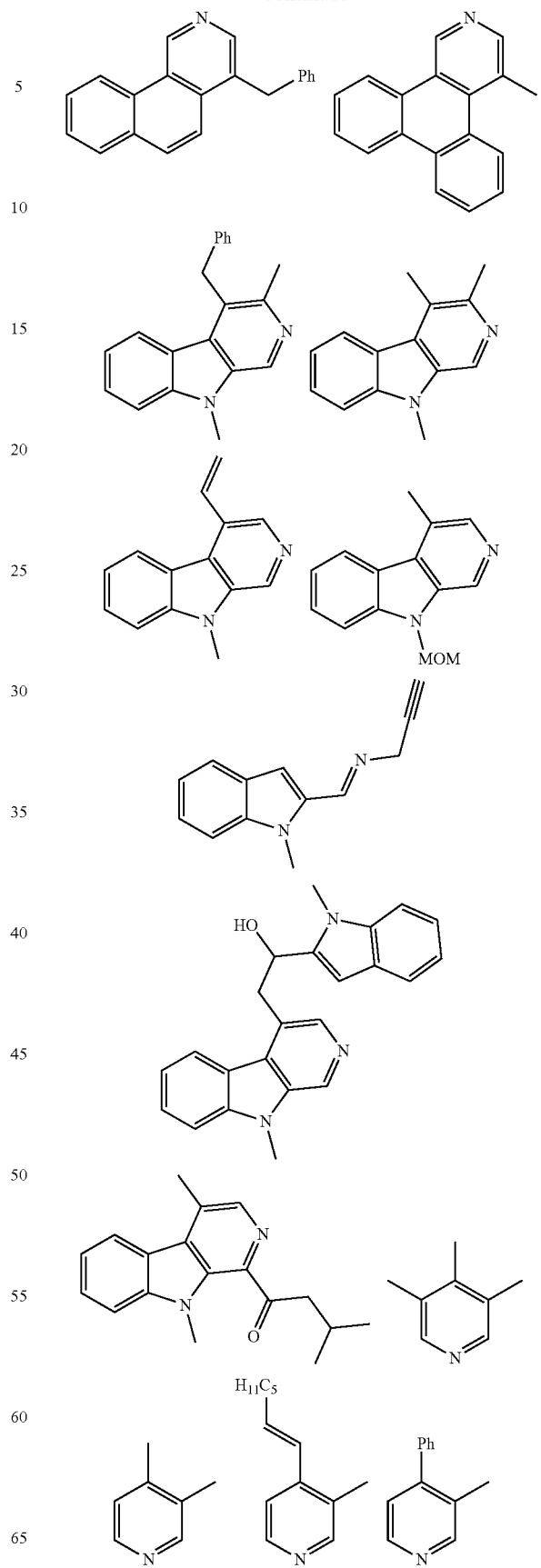

-continued
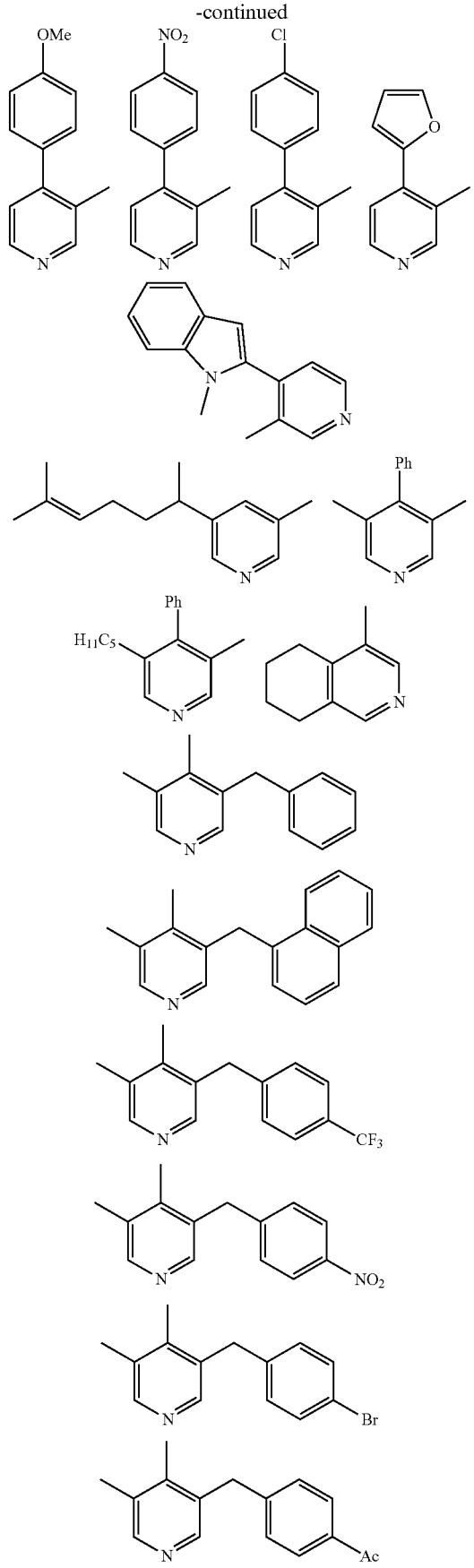
-continued
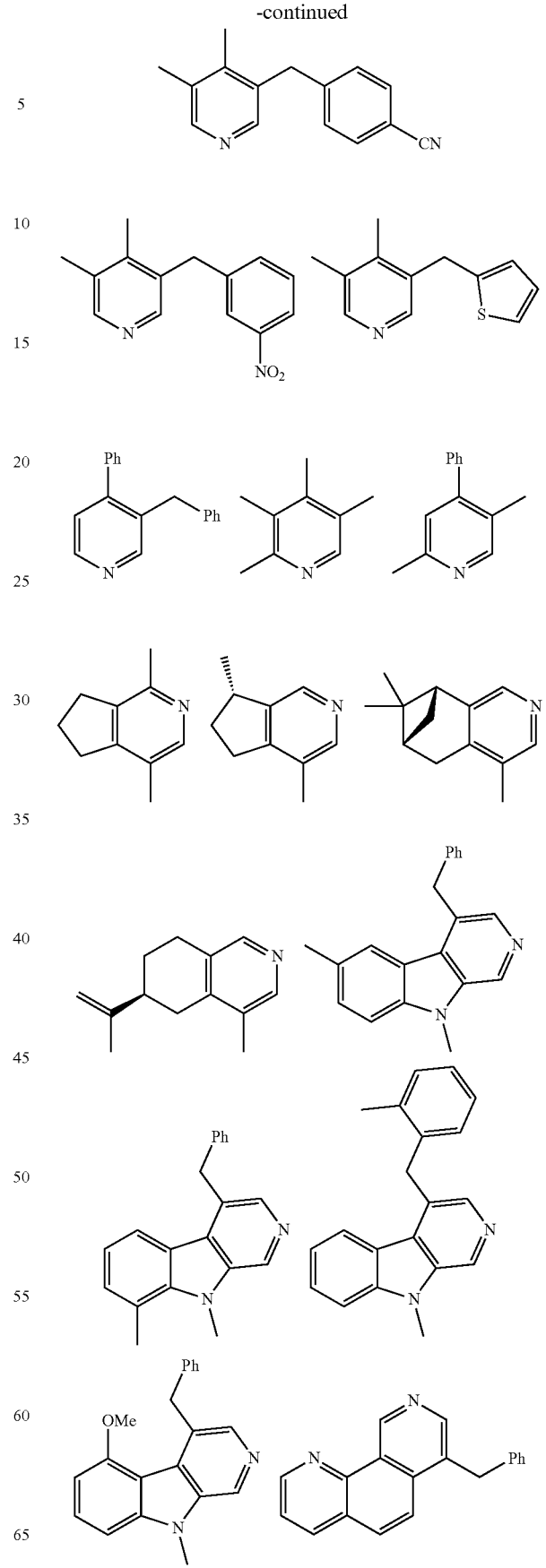

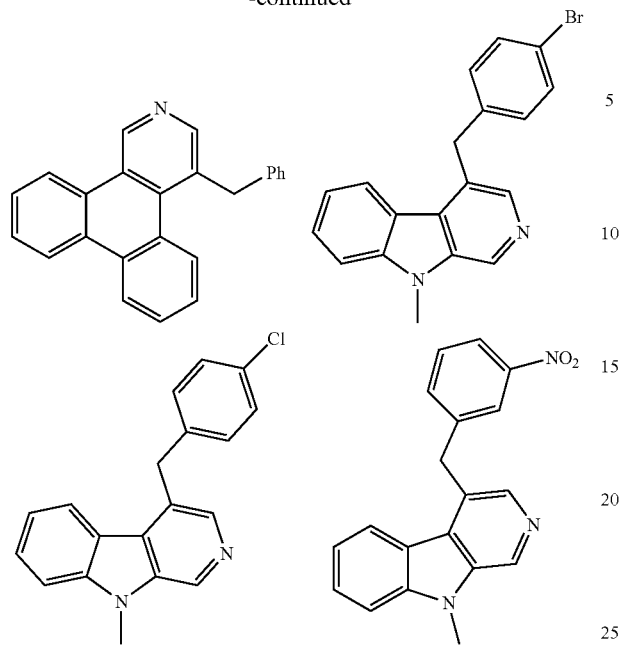
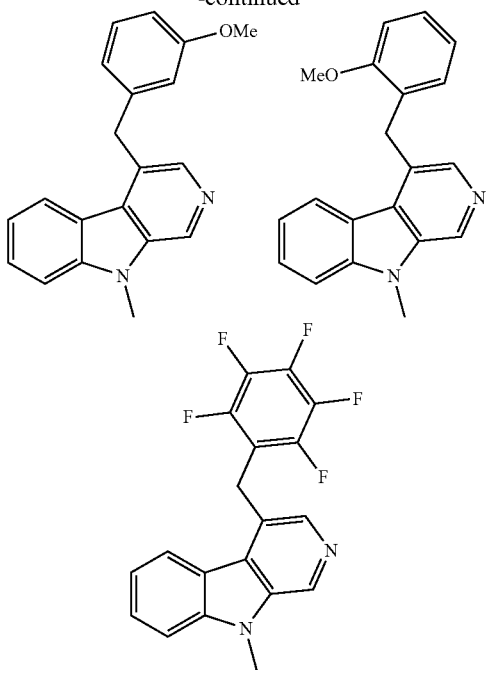
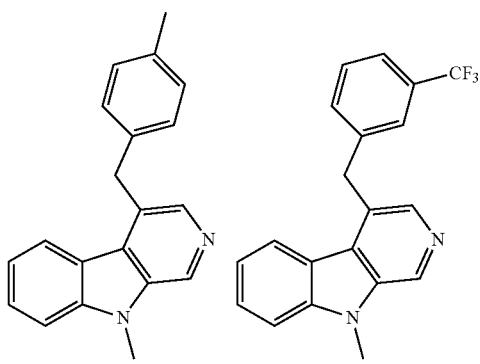

Without wishing to be bound by theory, it is believed that the reaction involves imine formation followed by concomitant cyclization through an allenyl intermediate to afford pyridines in excellent yields, with water as the sole by-product. This mild strategy is also suitable for functionalization of natural products or other advanced intermediates having α, β-unsaturated carbonyl functionality. For example, based on certain preliminary studies, a plausible mechanism for construction of a pyridine ring was proposed. First, taglic aldehyde 1a condenses with propargylamine 2a to give the stable imine intermediate 3aa, which converts into the allene in the presence of mild base, all in a single phase addition. The allene intermediate further undergoes 6π-azacyclization followed by aromatization through a [1,7]-H shift leading to the formation of substituted pyridine 3a.

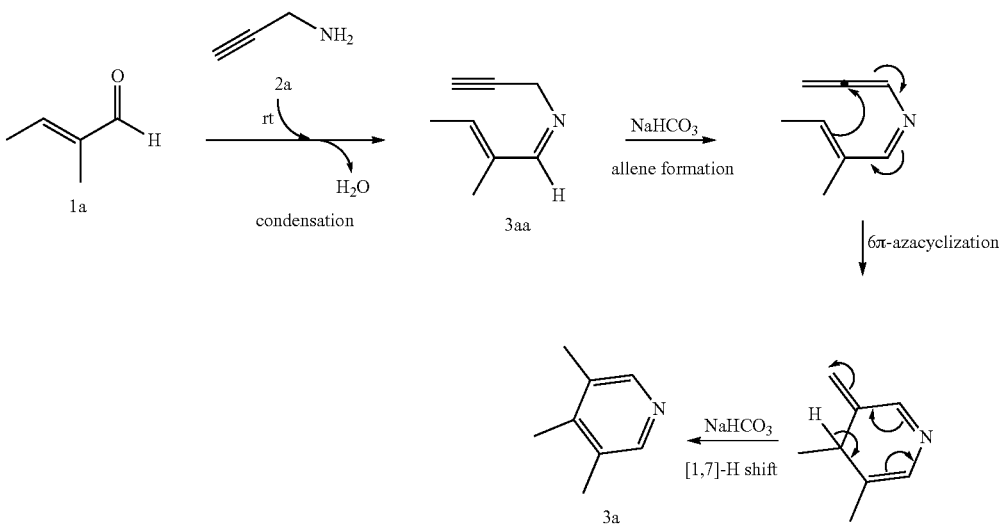

In certain embodiments of the present invention, the method comprises a one-step synthesis of the natural product, (−)-actinidine.

III. Compounds of the Invention

Compounds of the present invention may be prepared by the methods of the present invention. The compounds of the invention useful in the methods described herein may be selected from a compound of formula (I), or a salt, e.g., pharmaceutically acceptable salt, thereof.

As such, one embodiment of the present invention is a compound of formula (I)

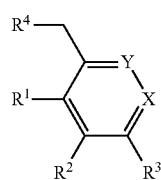
(I)

wherein
- $R^1$ is selected from the group consisting of H, $(C_1-C_4)$ alkyl (e.g., methyl), $(C_1-C_{10})$alkenyl (e.g., ethylene), phenyl, indolylalkyl (e.g., 2-hydroxy-2-(1-methyl-1H-indol-3-yl)ethyl), aryl (e.g., phenyl or napthyl), and heteroaryl (e.g., thiophenyl or furanyl), each of which may be optionally substituted with 1 to 5 substituents selected from the group consisting of $(C_1-C_4)$haloalkyl (e.g., $CF_3$), $(C_1-C_4)$alkoxy (e.g., $-OCH_3$), $-CN$, halogen (e.g., F, Br, Cl), $NO_2$, $(C_1-C_4)$alkyl (e.g., methyl) and OH;
- $R^2$ is selected from the group consisting of H and $(C_1-C_4)$alkyl (e.g., methyl);
- or $R^1$ and $R^2$ may be taken together with the carbons to which they are attached to form a ring structure selected from the group consisting of cycloalkyl, heterocyclyl, aryl, and heteroaryl (e.g., each of which monocyclic or polycyclic that may be fused or bridged), each of which may be optionally substituted with 1 to 3 substituents selected from the group consisting of $(C_1-C_4)$haloalkyl (e.g., $CF_3$), $(C_1-C_4)$alkoxy (e.g., $-OCH_3$), $-CN$, halogen (e.g., Br), $NO_2$, $(C_1-C_4)$alkyl (e.g., methyl), $(C_1-C_4)$alkenyl (e.g., propenyl), and OH;
- $R^3$ is selected from the group consisting of H, $(C_1-C_4)$ alkyl (e.g., methyl), $(C_1-C_6)$alkylcarbonyl (e.g., 3-methylbutanoyl), and benzyl;
- $R^4$ is selected from the group consisting of H, $-CH_2$, $(C_1-C_{10})$alkyl (e.g., straight or branched $(C_1-C_{10})$ alkyl (e.g., $CH_3$)), $(C_1-C_{10})$alkenyl (e.g., straight or branched $(C_1-C_{10})$alkenyl (e.g., heptenyl or octenyl)), each of which is optionally substituted with 1 to 4 substituents selected from the group consisting of $(C_1-C_4)$alkyl (e.g., methyl), halogen (e.g., Br), $-CN$, $-C(O)O-(C_1-C_4)$alkyl (e.g., $-C(O)OCH_3$), $-O-(C_1-C_4)$alkyl (e.g., $-OCH_3$); and
- X and Y are independently selected from N and $CR_5$, wherein $R_5$ is H or $(C_1-C_4)$alkyl (e.g., $CH_3$), and wherein one of X or Y is N and the other is $CR_5$.

with the proviso that the compound of formula (I) is not:

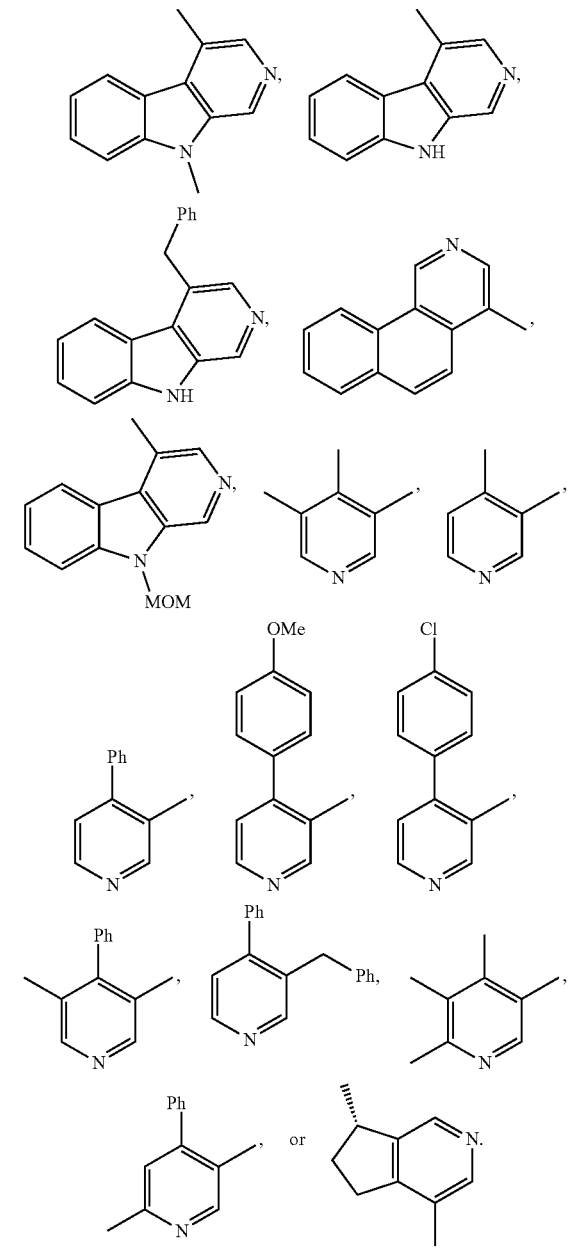

In certain embodiments, the compound of formula (I) is a compound of formula (IV):

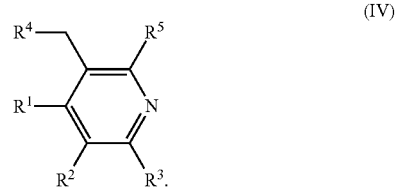
(IV)

In certain embodiments, the compound of formula (I) is a compound of formula (V):

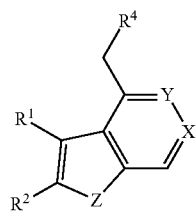

(V)

wherein

Z is selected from the group consisting of —O—, —S—, —N($R_6$)—, wherein $R_6$ is H, ($C_1$-$C_4$)alkyl (e.g., methyl), tosyl, benzyl, phenyl, tert-butyloxycarbonyl, In certain embodiments, the compound of formula (I) is a compound of formula (VI):

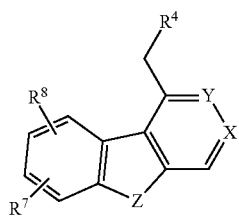

(VI)

wherein

Z is selected from the group consisting of —O—, —S—, —N($R_6$)—, wherein $R_6$ is H, ($C_1$-$C_4$)alkyl (e.g., methyl), tosyl, benzyl, phenyl, tert-butyloxycarbonyl; and $R^7$ and $R^8$ are each independently selected from the group consisting of H, ($C_1$-$C_4$)haloalkyl (e.g., $CF_3$), ($C_1$-$C_4$)alkoxy (e.g., —$OCH_3$), —CN, halogen (e.g., Br), $NO_2$, ($C_1$-$C_4$) alkyl (e.g., methyl), ($C_1$-$C_4$)alkenyl (e.g., propenyl), and OH.

Another embodiment of the present invention provides a compound selected from the following:

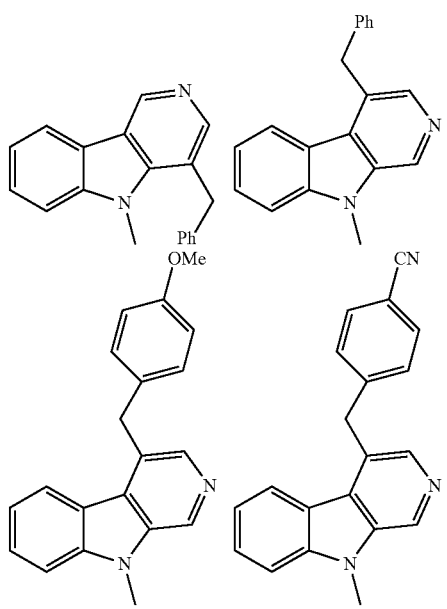

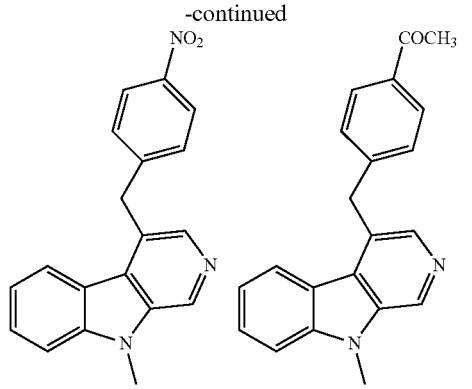

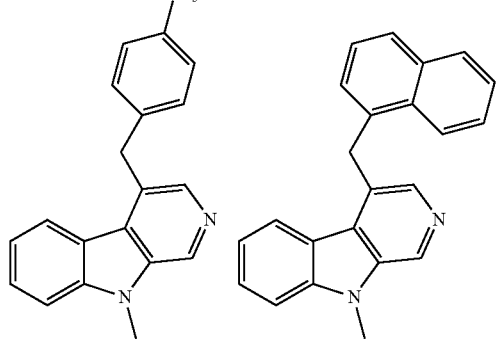

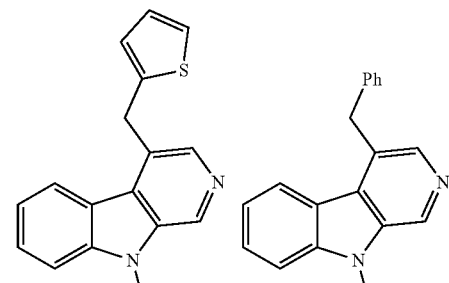

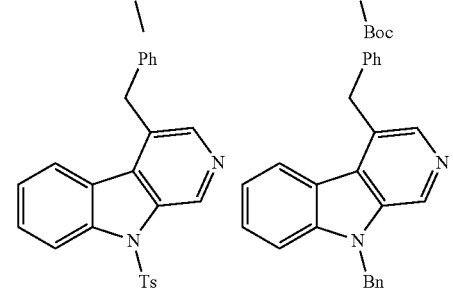

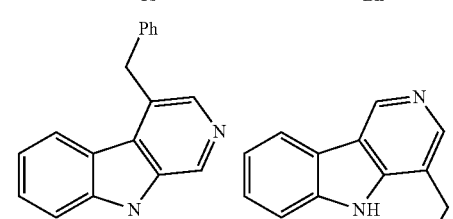

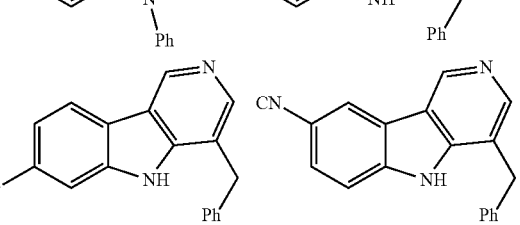

-continued
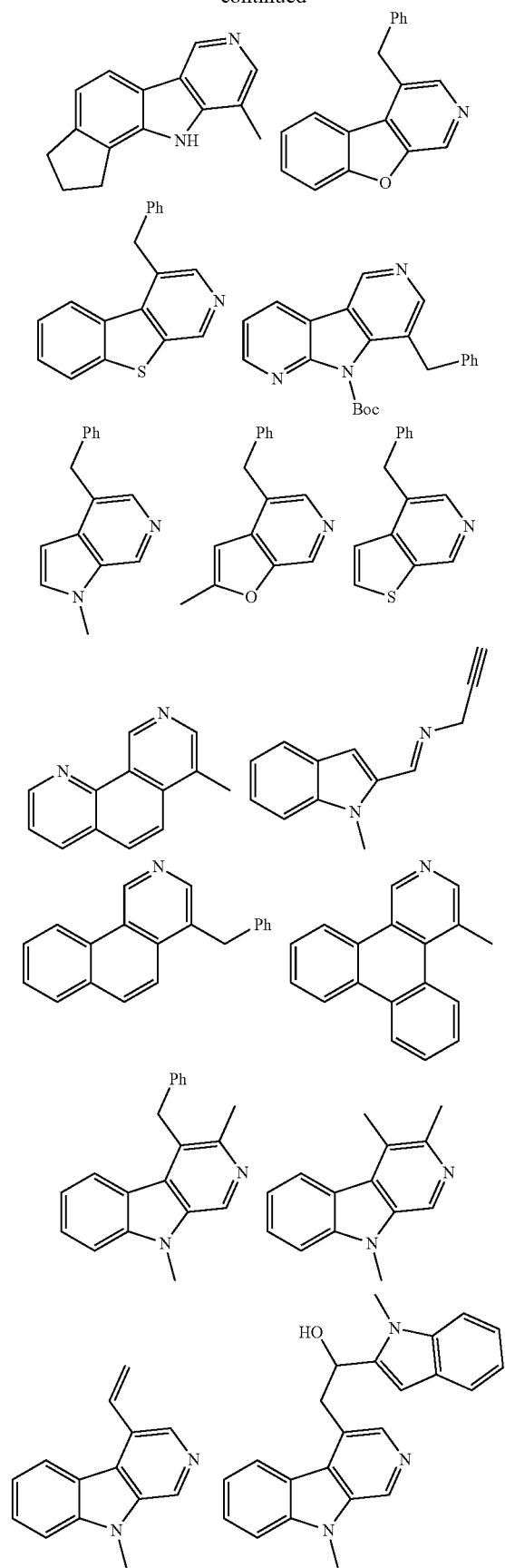
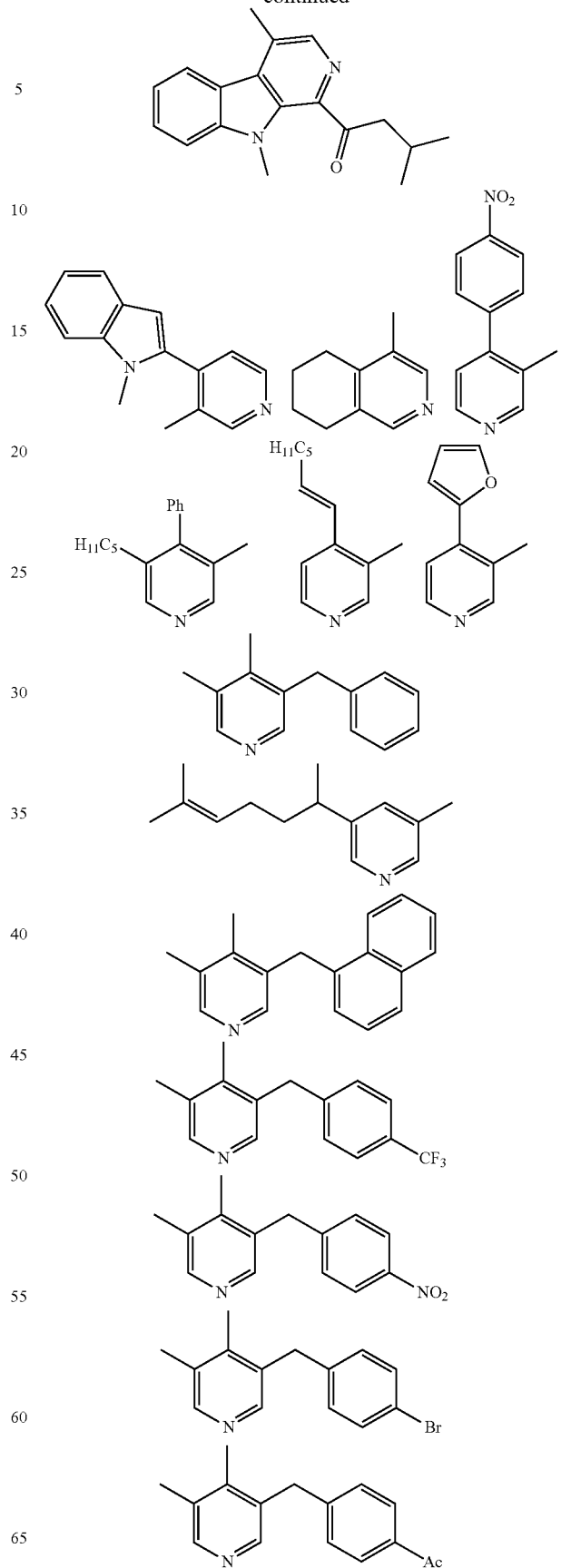

-continued

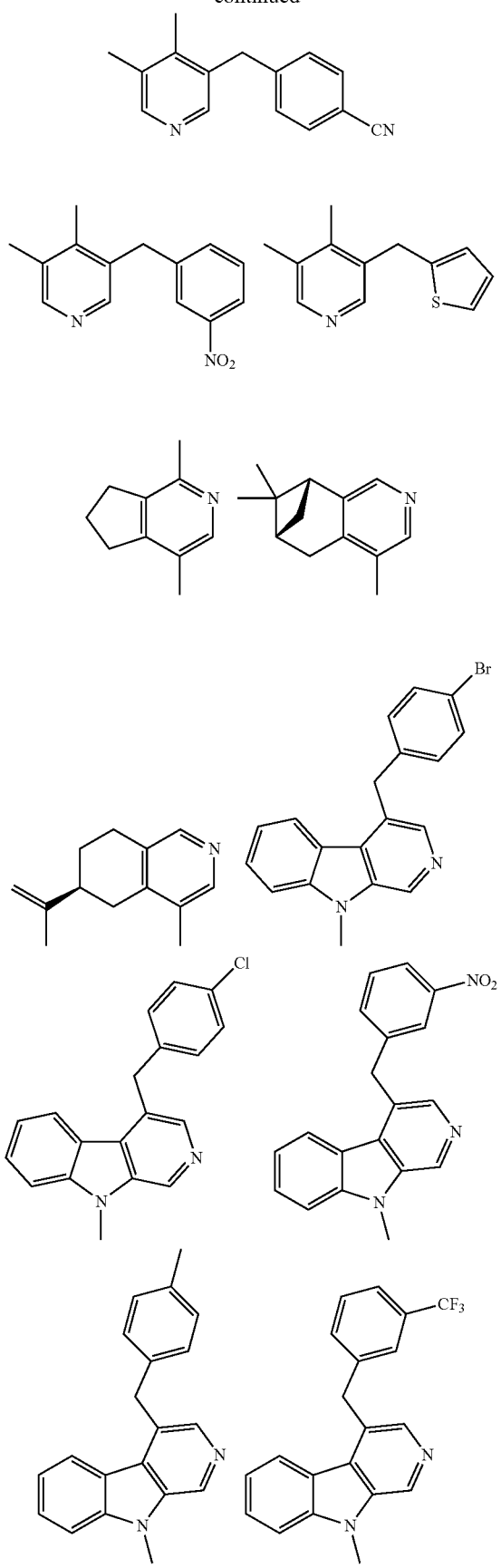
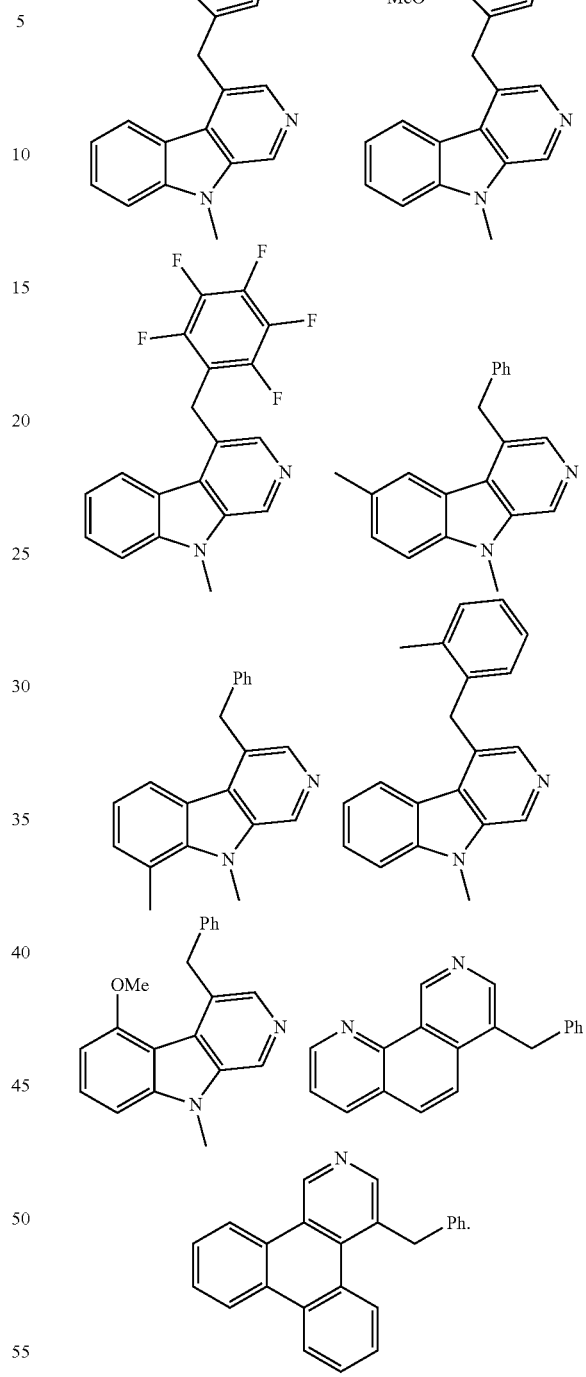

Additional Compound Forms:

Certain embodiments of formula (I) may contain asymmetric centers and exist as different enantiomers or diastereomers. Some compounds of the disclosure may have one or more chiral centers and/or geometric isomeric centers (E- and Z-isomers), and it is to be understood that the present disclosure encompasses all such optical, diastereoisomers and geometric isomers. The disclosure also comprises all tautomeric forms of the compounds disclosed herein. All enantiomers or diastereomeric forms are intended to be included within the scope of the present invention. The compounds of the invention may be racemic, or in a single enantiomer form In certain embodiments, compounds in the disclosure may be in the form of pharmaceutically acceptable salts. The phrase "pharmaceutically acceptable" refers to salts prepared from pharmaceutically acceptable non-toxic bases and acids, including inorganic and organic bases and inorganic and organic acids. Salts derived from inorganic bases include lithium, sodium, potassium, magnesium, calcium and zinc. Salts derived from organic bases include ammonia, primary (e.g. Tromethamine), secondary and tertiary amines, and amino acids (e.g. Lysine). Salts derived from inorganic acids include sulfuric, hydrochloric, phosphoric, methanesulphonic, hydrobromic. Salts derived from organic acids include $C_{1-6}$ alkyl carboxylic acids, di-carboxylic acids and tricarboxylic acids such as acetic acid, propionic acid, fumaric acid, maleic acid, succinic acid, tartaric acid, adipic acid and citric acid, and alkylsulfonic acids such as methanesulphonic, and aryl sulfonic acids such as para-toluene sulfonic acid and benzene sulfonic acid. For detailed list of slats see P. H. Stahl and C. G. Wermuth (eds.) "Handbook of Pharmaceutical Salts, Properties, Selection and Use" Wiley-VCH (ISBN 3-906390-26-8)

Compounds and pharmaceutically acceptable salts thereof may be in the form of a solvate. This occurs when a compound of the invention crystallizes in a manner that it incorporates solvent molecules into the crystal lattice. Examples of solvents forming solvates are water (hydrates), MeOH, EtOH, iPrOH, and acetone. Compounds of the invention described herein cover all solvates of the depicted compounds.

Compounds in the disclosure may exist in different crystal forms known as polymorphs.

Practitioners of the art will recognize that certain chemical groups may exist in multiple tautomeric forms. The scope of this disclosure is meant to include all such tautomeric forms. For example, a tetrazole may exist in two tautomeric forms, 1-H tetrazole and a 2-H tetrazole. This is depicted in FIG. below. This example is not meant to be limiting in the scope of tautomeric forms.

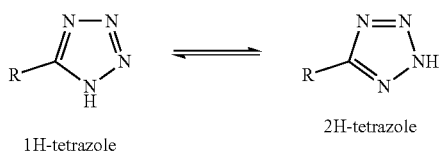

1H-tetrazole  2H-tetrazole

Practitioners of the art will also recognize that certain electrophilic ketones, may exist in a hydrated form. The scope of this disclosure is to include all such hydrated forms. For example, a trifluoromethyl ketone may exist in a hydrated form via addition of water to the carbonyl group. This is depicted in FIG. below. This example is not meant to be limiting in the scope of hydrated forms.

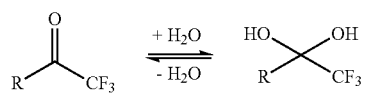

IV. Uses of the Compounds of the Invention

The compounds of the present invention may be useful as pharmaceuticals (e.g., for the therapeutically effective treatment of a disease or disorder), agrochemicals, in advanced organic materials such as OLEDs and fluorescent sensors. organic bases, ligand scaffolds, catalysts, directing groups in C—H activation reactions, and natural products.

A. Pharmaceutical Compositions

In certain embodiments, the compounds of the present invention may be used in pharmaceutical compositions.

For oral administration, a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; in particular embodiments, such materials also include lactose or milk sugar as well as high molecular weight polyethylene glycols. When aqueous suspensions and/or elixirs are desired for oral administration, the compounds/components of this invention can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of transdermal (e.g., topical) administration, dilute sterile, aqueous or partially aqueous solutions (usually in about 0.1% to 5% concentration), otherwise similar to the above parenteral solutions, may be prepared.

Methods of preparing various pharmaceutical compositions with a certain amount of active ingredient are known, or will be apparent in light of this disclosure, to those of ordinary skill in this art. For examples of methods of preparing pharmaceutical compositions, see Remington's Pharmaceutical Sciences, Mack Publishing Company, Easter, Pa., 15th Edition (1975). After a pharmaceutical composition has been formulated in an acceptable carrier, it can be placed in an appropriate container and labeled for treatment of an indicated condition. For administration of the compounds of the invention, such labeling would include, e.g., instructions concerning the amount, frequency and method of administration.

EXEMPLIFICATION

The present invention is illustrated by the following examples, which are not intended to be limiting in any way.

Example 1

General Parameter Studies 1-methyl-1H-indole-2-carbaldehyde (1a) was chosen as a model substrate in combination with propargylamine (2a).

The imine formation and cyclization reaction proceeded, and the corresponding β-carboline 3a was obtained in 15% yield using 2 mol % [Cp*RhCl₂]₂ and sodium acetate under an argon atmosphere in methanol at 60° C. for 24 h (Table 1, entry 1). Next, with the same catalyst and base, various solvents were screened, including toluene, DCE, HFIP and DMF. The investigation showed that toluene and DCE gave inferior yields (entries 2 and 3), whereas DMF was a better solvent than HFIP in this reaction (entries 4 and 5). It was determined that switching the catalyst to 5 mol % Pd(OAc)₂ was also efficient for this conversion in the presence of NaOAc in DMF at 80° C. for 24 h and delivered 3a in 50% yield (entry 6).

In sharp contrast, the replacement of NaOAc with NaHCO₃ as a base significantly improved the yield of 3a within 9 h at 80° C. (entry 7). Changing the base to Cs₂CO₃ or KHPO₄ had a deleterious effect on the reaction under Pd-catalysis (entries 8 and 9). Interestingly, higher yield was observed with Cu(OAc)₂ and NaHCO₃ conditions to deliver 3a in 84% yield (entry 10). Investigation of other bases with Cu(OAc)₂ deteriorated the reaction progress (entries 11-13).

In an attempt to improve the yield of transformation, alternative and environmentally benign conditions were screened. Surprisingly, further examination of the optimization conditions revealed that carboline 3a formed in good yield even in the absence of catalyst (86%, entry 14). The reaction fails to provide carboline 3a in the absence of both base and catalyst (entry 16). Rather, the corresponding imine (3aa) was isolated in 85% yield. Subsequent cyclization of this intermediate to 3a (88%) was accomplished using the optimized reaction conditions (NaHCO₃ in DMF at 80° C.) for 6 hours.

Oxopropalines D And G

The formal synthesis of oxopropalines D and G was also achieved on gram-scale (3a), in a single phase reaction from commercially available materials (where the previous shortest reported route to 3a was 5 steps). NMR studies of the conversion of imine intermediate 3aa to β-carboline 3a were conducted and revealed that the reaction proceeded through an allene intermediate.

Example 2

General Method of Preparation of β-Carbolines, γ-Carbolines and Fused Azaheterocycles To a stirred solution of aldehyde 1a-z (0.6 mmol) and propargylic amine/propargylic amine hydrochloride (0.9 mmol) in DMF (2 mL) were added 4 Å molecular sieves (200 mg) and NaHCO₃ (1.2 mmol for free propargylic amines and 1.8 mmol for propargylic amine hydrochlorides) at room temperature under an argon atmosphere. The reaction mixture was stirred for 3 h at room temperature, followed by 6 h at 80° C. (heated for 24 h at 80° C. in case of N—H indole aldehydes). The mixture was filtered through Celite, and water (10 mL) was added to filtrate. Two layers were separated, and the aqueous layer was extracted with EtOAc (2×10 mL). The combined organic layer was washed with ice cold water (2×15 mL), dried over magnesium sulfate and evaporated under reduced pressure. The crude product was purified by flash column chromatography on silica gel to afford the corresponding β-carbolines (3a-s and 3z), γ-carbolines (3t-y) and fused azaheterocycles (4a-j). Structures of Representative Aldehydes (1a-z):

TABLE 1

Optimization of reaction parameters.[a]

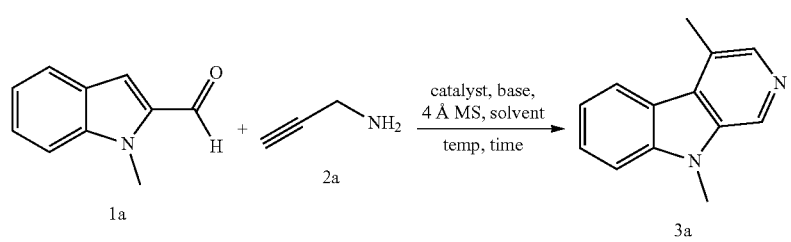

| entry | catalyst | base | solvent | temp (° C.) | time (h) | yield (%)[b] |
|---|---|---|---|---|---|---|
| 1 | [Cp * RhCl₂]₂ | NaOAc | MeOH | 60 | 24 | 15 |
| 2 | [Cp * RhCl₂]₂ | NaOAc | toluene | 100 | 24 | 30 |
| 3 | [Cp * RhCl₂]₂ | NaOAc | DCE | 80 | 24 | 30 |
| 4 | [Cp * RhCl₂]₂ | NaOAc | HFIP | 80 | 24 | 45 |
| 5 | [Cp * RhCl₂]₂ | NaOAc | DMF | 80 | 24 | 48 |
| 6 | Pd(OAc)₂ | NaOAc | DMF | 80 | 24 | 50 |
| 7 | Pd(OAc)₂ | NaHCO₃ | DMF | 80 | 9 | 80 |
| 8 | Pd(OAc)₂ | CsCO₃ | DMF | 80 | 24 | 47 |
| 9 | Pd(OAc)₂ | K₂HPO₄ | DMF | 80 | 24 | 25 |
| 10 | Cu(OAc)₂ | NaHCO₃ | DMF | 80 | 9 | 84 |
| 11 | Cu(OAc)₂ | Na₂CO₃ | DMF | 80 | 9 | 63 |
| 12 | Cu(OAc)₂ | K₂CO₃ | DMF | 80 | 9 | 67 |
| 13 | Cu(OAc)₂ | CsCO₃ | DMF | 80 | 9 | 63 |
| 14 | — | NaHCO₃ | DMF | 80 | 9 | 86 |
| 15 | Cu(OAc)₂ | — | DMF | 80 | 24 | 23 |
| 16[c] | — | — | DMF | 80 | 24 | 0 |

[a]Reaction conditions: 1a (0.6 mmol), 2a (0.9 mmol) and base (1.2 mmol); [Cp * RhCl₂]₂ (2 mol %), Pd (OAc)₂ (5 mol %), Cu (OAc)₂ (10 mol %);
[b]isolated yield;
[c]Imine 3aa was isolated (85%).

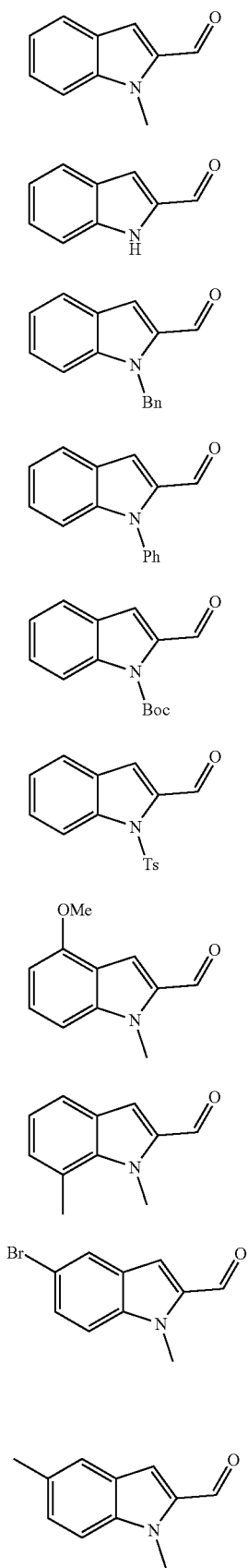
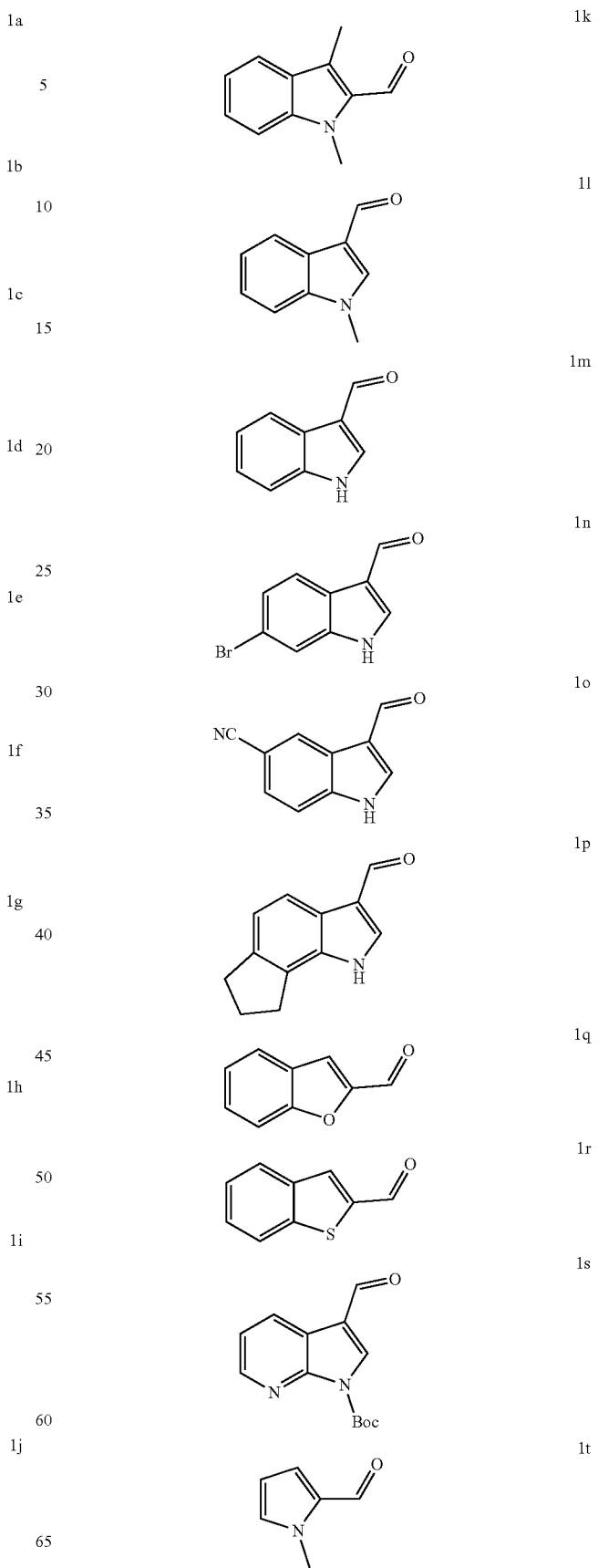

-continued
| | |
|---|---|
| 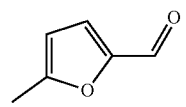 | 1u |
| 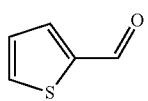 | 1v |
| 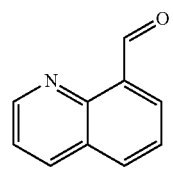 | 1w |
| 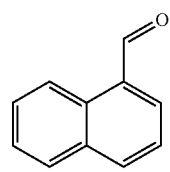 | 1x |
| 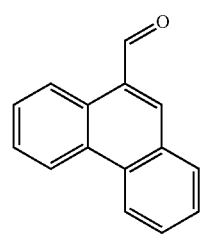 | 1y |
| 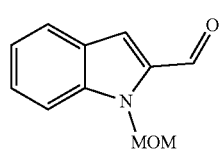 | 1z |
Structures of Representative Propargylic Amines (2a-l):
| | |
|---|---|
| 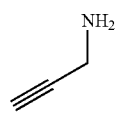 | 2a |
| 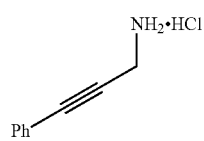 | 2b |
| 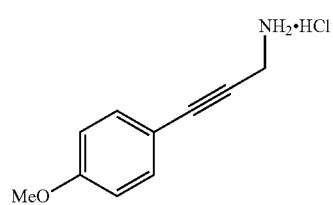 | 2c |
-continued
| | |
|---|---|
|  | 2d |
| 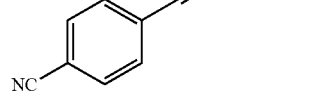 | 2e |
|  | 2f |
| 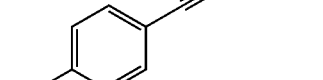 | 2g |
|  | 2h |
|  | 2i |
| 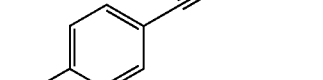 | 2j |
|  | 2k |

21

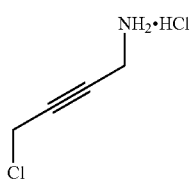

4,9-Dimethyl-9H-pyrido[3,4-b]indole (3a)

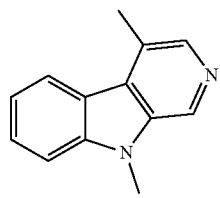

1-Methyl-1H-indole-2-carbaldehyde (1a, 95 mg, 0.60 mmol), propargylamine (2a, 49.5 mg, 0.90 mmol) and NaHCO$_3$ (101 mg, 1.20 mmol) in DMF (3 mL) were stirred for 3 h at room temperature followed by 6 h at 80° C. After column chromatography (CH$_2$Cl$_2$/MeOH 100:0 to 99:1), 101 mg (86%) of a pale, yellow solid was obtained. R$_f$=0.4 (CH$_2$Cl$_2$/MeOH 95:5), mp=143-144° C.; $^1$H NMR (400 MHz, CDCl$_3$): δ 8.77 (s, 1H), 8.27 (s, 1H), 8.22 (d, J=7.9 Hz, 1H), 7.62 (t, J=7.7 Hz, 1H), 7.49 (d, J=8.3 Hz, 1H), 7.32 (t, J=7.5 Hz, 1H), 3.93 (s, 3H), 2.84 (s, 3H); $^{13}$C{$^1$H}NMR (100 MHz, CDCl$_3$): δ 141.6, 139.4, 136.6, 129.4, 127.8, 127.1, 124.4, 123.7, 121.6, 119.7, 109.0, 29.4, 17.4; FTIR (neat): 3043, 2968, 2923, 1616, 1490, 1460, 1326, 1267, 1154, 1021, 855, 743, 728 cm$^{-1}$; MS (ESI): m/z 197 (M+H)$^+$; HRMS (ESI): m/z calcd for C$_{13}$H$_{13}$N$_2$ (M+H)$^+$: 197.1073, found: 197.1072.

4-Benzyl-9-methyl-9H-pyrido[3,4-b]indole (3b)

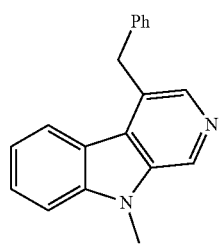 [SMILES: Cn1c2ccccc2c2c(Cc3ccccc3)cncc21]

1-Methyl-1H-indole-2-carbaldehyde (1a, 95 mg, 0.60 mmol), 3-phenylprop-2-yn-1-amine hydrochloride (2b, 150 mg, 0.90 mmol) and NaHCO$_3$ (151 mg, 1.80 mmol) in DMF (3 mL) were stirred for 3 h at room temperature followed by 6 h at 80° C. After column chromatography (CH$_2$Cl$_2$/MeOH 100:0 to 99:1), 142 mg (87%) of a pale, yellow solid was obtained. R$_f$=0.6 (CH$_2$Cl$_2$/MeOH 95:5), mp=134-136° C.; $^1$H NMR (400 MHz, CDCl$_3$): δ 8.83 (s, 1H), 8.27 (s, 1H), 8.01 (d, J=8.0 Hz, 1H), 7.61-7.53 (m, 1H), 7.45 (d, J=8.3 Hz, 1H), 7.30-7.13 (m, 6H), 4.60 (s, 2H), 3.93 (s, 3H); $^{13}$C{$^1$H}NMR (100 MHz, CDCl$_3$): δ 141.6, 140.3, 139.0, 136.8, 130.2, 129.1, 128.5, 128.5, 127.8, 126.9, 126.3, 123.9, 120.9, 119.7, 109.0, 37.1, 29.3; FTIR (neat): 3025, 2937, 1603, 1493, 1446, 1329, 1154, 1024, 981, 749, 727, 693 cm$^{-1}$; MS (ESI): m/z 273 (M+H)$^+$; HRMS (ESI): m/z calcd for C$_{19}$H$_{17}$N$_2$ (M+H)$^+$: 273.1386, found: 273.1382.

4-(4-Methoxybenzyl)-9-methyl-9H-pyrido[3,4-b]indole (3c)

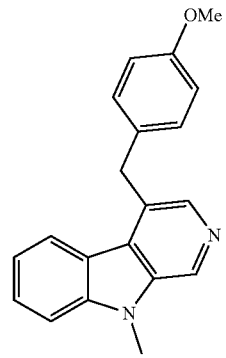 [SMILES: COc1ccc(Cc2cncc3c2c2ccccc2n3C)cc1]

1-Methyl-1H-indole-2-carbaldehyde (1a, 95 mg, 0.60 mmol), 3-(4-methoxyphenyl)prop-2-yn-1-amine hydrochloride (2c, 177 mg, 0.90 mmol) and NaHCO$_3$ (151 mg, 1.80 mmol) in DMF (3 mL) were stirred for 3 h at room temperature followed by 6 h at 80° C. After column chromatography (CH$_2$Cl$_2$/MeOH 100:0 to 99:1), 130 mg (72%) of a white solid was obtained. R$_f$=0.6 (CH$_2$Cl$_2$/MeOH 95:5), mp=111-113° C.; $^1$H NMR (400 MHz, CDCl$_3$): δ 8.83 (s, 1H), 8.26 (s, 1H), 8.03 (d, J=7.9 Hz, 1H), 7.58 (ddd, J=8.3, 5.6, 1.1 Hz, 1H), 7.47 (d, J=8.3 Hz, 1H), 7.23-7.18 (m, 1H), 7.14 (d, J=8.8 Hz, 2H), 6.84-6.75 (m, 2H), 4.55 (s, 2H), 3.96 (s, 3H), 3.75 (s, 3H); $^{13}$C{$^1$H}NMR (100 MHz, CDCl$_3$): δ 158.0, 141.6, 140.3, 136.9, 131.0, 130.3, 129.5, 129.4, 127.8, 126.9, 124.0, 121.0, 119.7, 114.0, 109.0, 55.2, 36.3, 29.4; FTIR (neat): 3028, 2923, 2850, 1661, 1492, 1447, 1433, 1328, 1245, 1172, 1027, 867, 746, 729, 694 cm$^{-1}$; MS (ESI): m/z 303 (M+H)$^+$; HRMS (ESI): m/z calcd for C$_{20}$H$_{19}$N$_2$O (M+H)$^+$: 303.1492, found: 303.1488.

4-((9-Methyl-9H-pyrido[3,4-b]indol-4-yl)methyl)benzonitrile (3d)

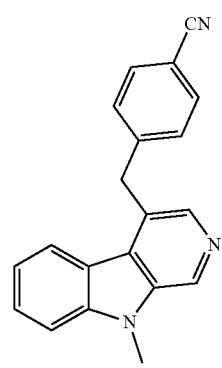 [SMILES: Cn1c2ccccc2c2c(Cc3ccc(C#N)cc3)cncc21]

1-Methyl-1H-indole-2-carbaldehyde (1a, 95 mg, 0.60 mmol), 4-(3-aminoprop-1-yn-1-yl)benzonitrile hydrochloride (2d, 172.8 mg, 0.90 mmol) and NaHCO$_3$ (151 mg, 1.80 mmol) in DMF (3 mL) were stirred for 3 h at room temperature followed by 6 h at 80° C. After column chromatography (CH$_2$Cl$_2$/MeOH 100:0 to 99:1), 157 mg (88%) of a pale, yellow solid was obtained. R$_f$=0.5 (CH$_2$Cl$_2$/MeOH 95:5), mp=125-127° C.; $^1$H NMR (400 MHz, CDCl$_3$): δ 8.90 (s, 1H), 8.29 (s, 1H), 7.89 (d, J=8.0 Hz, 1H), 7.65-7.59 (m, 1H), 7.57 (d, J=8.3 Hz, 2H), 7.52 (d, J=8.3 Hz, 1H), 7.34 (d, J=8.4 Hz, 2H), 7.25-7.19 (m, 1H), 4.68 (s, 2H), 4.00 (s, 3H); $^{13}C\{^1H\}$NMR (100 MHz, CDCl$_3$): δ 144.7, 141.7, 140.3, 136.9, 132.4, 131.0, 129.2, 128.1, 127.2, 126.8, 123.4, 120.5, 119.9, 118.8, 110.3, 109.3, 37.2, 29.5; FTIR (neat): 3065, 2926, 2226, 1603, 1491, 1444, 1442, 1328, 1229, 1156, 1017, 913, 809, 748, 732 cm$^{-1}$; MS (ESI): m/z 298 (M+H)$^+$; HRMS (ESI): m/z calcd for C$_{20}$H$_{16}$N$_3$ (M+H)$^+$: 298.1339, found: 298.1335.

9-Methyl-4-(4-nitrobenzyl)-9H-pyrido[3,4-b]indole (3e)

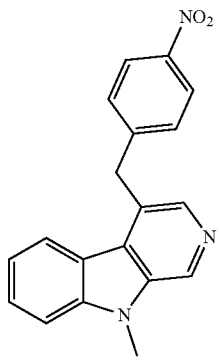 [SMILES: Cn1c2ccccc2c2c(Cc3ccc([N+](=O)[O-])cc3)cncc21]

1-Methyl-1H-indole-2-carbaldehyde (1a, 95 mg, 0.60 mmol), 3-(4-nitrophenyl)prop-2-yn-1-amine hydrochloride (2e, 190.8 mg, 0.90 mmol) and NaHCO$_3$ (151 mg, 1.80 mmol) in DMF (3 mL were stirred for 3 h at room temperature followed by 6 h at 80° C. After column chromatography (CH$_2$Cl$_2$/MeOH 100:0 to 99:1), 158 mg (83%) of a pale, yellow solid was obtained. R$_f$=0.6 (CH$_2$Cl$_2$/MeOH 95:5), mp=145-147° C.; $^1$H NMR (400 MHz, CDCl$_3$): δ 8.91 (s, 1H), 8.29 (s, 1H), 8.12 (d, J=8.7 Hz, 2H), 7.87 (d, J=8.0 Hz, 1H), 7.61 (t, J=7.7 Hz, 1H), 7.51 (d, J=8.3 Hz, 1H), 7.37 (d, J=8.6 Hz, 2H), 7.20 (t, J=7.6 Hz, 1H), 4.72 (s, 2H), 4.00 (s, 3H); $^{13}C\{^1H\}$NMR (100 MHz, CDCl$_3$): δ 146.8, 146.7, 141.8, 140.0, 130.9, 129.2, 129.2, 128.3, 126.9, 123.9, 123.9, 123.4, 120.5, 120.0, 109.4, 37.0, 29.5; FTIR (neat): 3209, 3051, 2853, 1696, 1512, 1455, 1400, 1343, 1109, 1051, 791, 729 cm$^{-1}$; MS (ESI): m/z 318 (M+H)$^+$; HRMS (ESI): m/z calcd for C$_{19}$H$_{16}$N$_3$O$_2$ (M+H)$^+$: 318.1237, found: 318.1231.

1-(4-((9-Methyl-9H-pyrido[3,4-b]indol-4-yl)methyl)phenyl)ethanone (3f)

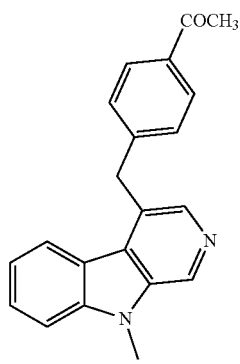 [SMILES: CC(=O)c1ccc(Cc2cncc3c2c2ccccc2n3C)cc1]

1-Methyl-1H-indole-2-carbaldehyde (1a, 95 mg, 0.60 mmol), 1-(4-(3-aminoprop-1-yn-1-yl)phenyl)ethanone hydrochloride (2f, 188 mg, 0.90 mmol) and NaHCO$_3$ (151 mg, 1.80 mmol) in DMF (3 mL were stirred for 3 h at room temperature followed by 6 h at 80° C. After column chromatography (CH$_2$Cl$_2$/MeOH 100:0 to 99:1), 152 mg (81%) of a white solid was obtained. R$_f$=0.6 (CH$_2$Cl$_2$/MeOH 95:5), mp=139-141° C.; $^1$H NMR (400 MHz, CDCl$_3$): δ 8.86 (s, 1H), 8.28 (s, 1H), 7.92 (d, J=8.0 Hz, 1H), 7.89-7.80 (m, 2H), 7.58 (ddd, J=8.3, 7.1, 1.1 Hz, 1H), 7.48 (d, J=8.3 Hz, 1H), 7.31 (d, J=8.5 Hz, 2H), 7.18 (ddd, J=8.0, 7.2, 1.0 Hz, 1H), 4.66 (s, 2H), 3.97 (s, 3H), 2.54 (s, 3H); $^{13}C\{^1H\}$NMR (100 MHz, CDCl$_3$): 5197.7, 144.7, 141.8, 140.0, 136.9, 135.5, 130.5, 128.8, 128.6, 128.4, 128.1, 127.0, 123.7, 120.7, 119.9, 109.2, 37.2, 29.5, 26.5; FTIR (neat): 3045, 2922, 2851, 1687, 1647, 1439, 1349, 1260, 1159, 996, 855, 728, 698 cm$^{-1}$; MS (ESI): m/z 315 (M+H)$^+$; HRMS (ESI): m/z calcd for C$_{21}$H$_{19}$N$_2$O (M+H)$^+$: 315.1492. found: 315.1489.

9-Methyl-4-(4-(trifluoromethyl)benzyl)-9H-pyrido[3,4-b]indole (3 g)

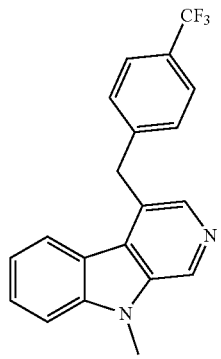

1-Methyl-1H-indole-2-carbaldehyde (1a, 95 mg, 0.60 mmol), 3-(4-(trifluoromethyl)phenyl)prop-2-yn-1-amine hydrochloride (2 g, 211 mg, 0.90 mmol) and NaHCO$_3$ (151 mg, 1.80 mmol) in DMF (3 mL were stirred for 3 h at room temperature followed by 6 h at 80° C. After column chromatography (CH$_2$Cl$_2$/MeOH 100:0 to 99:1), 190 mg (93%) of a white solid was obtained. R$_f$=0.5 (CH$_2$Cl$_2$/MeOH 95:5), mp=174-176° C.; $^1$H NMR (400 MHz, CDCl$_3$): δ 8.91 (s, 1H), 8.32 (s, 1H), 7.93 (d, J=8.0 Hz, 1H), 7.59 (t, J=7.7 Hz, 1H), 7.49 (t, J=8.1 Hz, 3H), 7.32 (d, J=8.0 Hz, 2H), 7.20 (t, J=7.5 Hz, 1H), 4.65 (s, 2H), 3.96 (s, 3H); $^{13}C\{^1H\}$NMR (100 MHz, CDCl$_3$): δ 143.2, 141.7, 140.3, 130.6, 128.8, 128.7, 128.5, 128.2, 128.0, 126.7, 125.5 (q, J=3.7 Hz), 123.6, 122.8, 120.7, 119.8, 109.2, 37.0, 29.4; FTIR (neat): 3066, 2923, 2852, 1617, 1469, 1442, 1323, 1268, 1154, 1113, 1023, 860, 744, 726 cm$^{-1}$; MS (ESI): m/z 341 (M+H)$^+$; HRMS (ESI): m/z calcd for C$_{20}$H$_{16}$F$_3$N$_2$ (M+H)$^+$: 341.1260, found: 341.1257.

9-Methyl-4-(naphthalen-1-ylmethyl)-9H-pyrido[3,4-b]indole (3h)

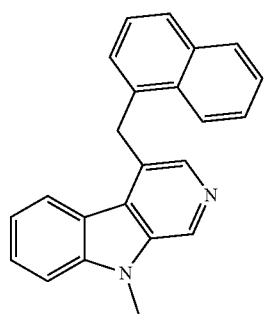 [SMILES: Cn1c2ccccc2c2c(Cc3cccc4ccccc34)cncc21]

1-Methyl-1H-indole-2-carbaldehyde (1a, 95 mg, 0.60 mmol), 3-(naphthalen-1-yl)prop-2-yn-1-amine hydrochloride (2h, 195 mg, 0.90 mmol) and NaHCO$_3$ (151 mg, 1.80 mmol) in DMF (3 mL were stirred for 3 h at room temperature followed by 6 h at 80° C. After column chromatography (CH$_2$Cl$_2$/MeOH 100:0 to 99:1), 164 mg (85%) of a pale, yellow solid was obtained. R$_f$=0.6 (CH$_2$Cl$_2$/MeOH 95:5), mp=203-205° C.; $^1$H NMR (400 MHz, CDCl$_3$): δ 8.89 (s, 1H), 8.16 (s, 1H), 8.14 (dd, J=6.2, 3.4 Hz, 1H), 7.93 (dd, J=6.1, 3.4 Hz, 1H), 7.87 (d, J=8.0 Hz, 1H), 7.76 (d, J=8.2 Hz, 1H), 7.62-7.49 (m, 4H), 7.31-7.24 (m, 1H), 7.12 (t, J=7.5 Hz, 1H), 7.04 (d, J=6.9 Hz, 1H), 5.05 (s, 2H), 4.00 (s, 3H); $^{13}$C{$^1$H}NMR (100 MHz, CDCl$_3$): δ 141.8, 134.2, 133.8, 132.0, 128.9, 128.9, 128.3, 128.0, 127.3, 126.4, 126.3, 126.2, 126.0, 125.8, 125.6, 125.1, 123.9, 123.5, 121.0, 119.9, 109.1, 34.4, 29.5; FTIR (neat): 3046, 2921, 2851, 1619, 1445, 1330, 1268, 1159, 1024, 980, 882, 791, 741 cm$^{-1}$; MS (ESI): m/z 323 (M+H)$^+$; HRMS (ESI): m/z calcd for C$_{23}$H$_{19}$N$_2$ (M+H)$^+$: 323.1543, found: 323.1536.

9-Methyl-4-(thiophen-2-ylmethyl)-9H-pyrido[3,4-b]indole (3i)

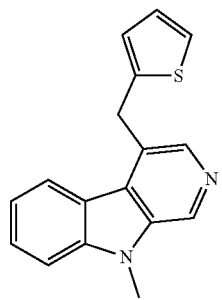 [SMILES: Cn1c2ccccc2c2c(Cc3cccs3)cncc21]

1-Methyl-1H-indole-2-carbaldehyde (1a, 95 mg, 0.60 mmol), 3-)thiophen 2-yl)prop-2-yn-1-amine hydrochloride (2i, 155.7 mg, 0.90 mmol) and NaHCO$_3$ (151 mg, 1.80 mmol) in DMF (3 mL were stirred for 3 h at room temperature followed by 6 h at 80° C. After column chromatography (CH$_2$Cl$_2$/MeOH 100:0 to 99:1), 135 mg (81%) of a pale, yellow solid was obtained. R$_f$=0.4 (CH$_2$Cl$_2$/MeOH 95:5), mp=156-158° C.; $^1$H NMR (400 MHz, CDCl$_3$): δ 8.84 (s, 1H), 8.35 (s, 1H), 8.07 (d, J=8.0 Hz, 1H), 7.62-7.54 (m, 1H), 7.47 (d, J=8.3 Hz, 1H), 7.26-7.18 (m, 1H), 7.12 (dd, J=5.1, 1.0 Hz, 1H), 6.87 (dd, J=5.1, 3.5 Hz, 1H), 6.81-6.71 (m, 1H), 4.73 (s, 2H), 3.94 (s, 3H); $^{13}$C{$^1$H}NMR (100 MHz, CDCl$_3$): δ 142.0, 141.7, 139.8, 136.9, 130.7, 128.7, 127.9, 126.9, 126.6, 125.2, 124.0, 123.9, 120.7, 119.8, 109.1, 31.8, 29.4; FTIR (neat): 3050, 2998, 2921, 1618, 1446, 1428, 1329, 1264, 1153, 1023, 813, 746, 691 cm$^{-1}$; MS (ESI): m/z 279 (M+H)$^+$; HRMS (ESI): m/z calcd for C$_{17}$H$_{15}$N$_2$S (M+H)$^+$: 279.0950, found: 279.0945.

4-Methyl-9H-pyrido[3,4-b]indole (3j)

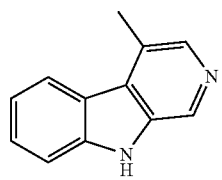

1H-Indole-2-carbaldehyde (1b, 87 mg, 0.60 mmol), propargylamine (2a, 49.5 mg, 0.90 mmol) and NaHCO$_3$ (101 mg, 1.20 mmol) in DMF (3 mL) were stirred for 3 h at room temperature followed by 21 h at 80° C. After column chromatography (CH$_2$Cl$_2$/MeOH 100:0 to 99:1), 67.7 mg (62%) of a pale, yellow solid was obtained. R$_f$=0.2 (CH$_2$Cl$_2$/MeOH 95:5), mp=206-208° C.; $^1$H NMR (400 MHz, CDCl$_3$: DMSO-d$_6$, 8:2): δ 11.12 (bs, 1H), 8.77 (s, 1H), 8.18 (d, J=10.3 Hz, 2H), 7.66-7.49 (m, 2H), 7.26 (t, J=7.3 Hz, 1H), 2.84 (s, 3H); $^{13}$C{$^1$H}NMR (100 MHz, CDCl$_3$: DMSO-d$_6$, 8:2): δ 140.0, 137.8, 134.9, 130.9, 126.6, 126.2, 125.9, 122.5, 120.7, 118.5, 110.9, 16.5; FTIR (neat): 3049, 2924, 2852, 1624, 1454, 1422, 1328, 1134, 1069, 847, 733, 691 cm$^{-1}$; MS (ESI): m/z 183 (M+H)$^+$; HRMS (ESI): m/z calcd for C$_{12}$H$_{11}$N$_2$ (M+H)$^+$: 183.0917, found: 183.0918.

4-Benzyl-9H-pyrido[3,4-b]indole (3k)

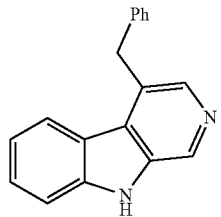

1H-Indole-2-carbaldehyde (1b, 87 mg, 0.60 mmol), 3-phenylprop-2-yn-1-amine hydrochloride (2b, 150 mg, 0.90 mmol) and NaHCO$_3$ (151 mg, 1.80 mmol) in DMF (3 mL) were stirred for 3 h at room temperature followed by 21 h at 80° C. After column chromatography (CH$_2$Cl$_2$/MeOH 100:0 to 99:1), 103 mg (67%) of a pale, yellow solid was obtained. R$_f$=0.3 (CH$_2$Cl$_2$/MeOH 95:5), mp=181-183° C.; $^1$H NMR (400 MHz, CDCl$_3$: DMSO-d$_6$, 8:2): δ 11.14 (bs, 1H), 8.85 (s, 1H), 8.18 (s, 1H), 7.99 (d, J=8.0 Hz, 1H), 7.60-7.51 (m, 1H), 7.47 (t, J=7.6 Hz, 1H), 7.29-7.20 (m, 4H), 7.16 (dt, J=15.0, 5.6 Hz, 2H), 4.59 (s, 2H); $^{13}$C{$^1$H}NMR (100 MHz, CDCl$_3$: DMSO-d$_6$, 8:2): δ 140.2, 138.8, 138.5, 135.5, 131.8, 128.2, 127.7, 127.7, 126.8, 126.1, 125.5, 122.8, 120.2, 118.6, 111.0, 36.3; FTIR (neat): 3010, 2856, 1569, 1457, 1403, 1346, 1259, 1173, 1005, 731, 697 cm$^{-1}$; MS (ESI): m/z 259 (M+H)$^+$; HRMS (ESI): m/z calcd for C$_{18}$H$_{15}$N$_2$ (M+H)$^+$: 259.1230, found: 259.1231.

4,9-Dibenzyl-9H-pyrido[3,4-b]indole (3l)

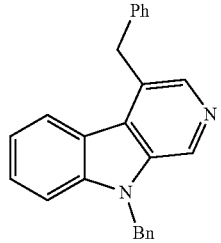

1-Benzyl-1H-indole-2-carbaldehyde (1c, 141 mg, 0.60 mmol), 3-phenylprop-2-yn-1-amine hydrochloride (2b, 150 mg, 0.90 mmol) and NaHCO$_3$ (151 mg, 1.80 mmol) in DMF (3 mL) were stirred for 3 h at room temperature followed by 6 h at 80° C. After column chromatography (CH$_2$Cl$_2$/MeOH 100:0 to 99:1), 164 mg (79%) of a pale, yellow solid was obtained. R$_f$=0.5 (CH$_2$Cl$_2$/MeOH 95:5), mp=135-136° C.; $^1$H NMR (400 MHz, CDCl$_3$): δ 8.80 (s, 1H), 8.27 (s, 1H), 8.06 (d, J=8.0 Hz, 1H), 7.53 (ddd, J=8.2, 7.1, 1.1 Hz, 1H), 7.45 (d, J=8.3 Hz, 1H), 7.33-7.24 (m, 7H), 7.24-7.13 (m, 4H), 5.60 (s, 2H), 4.64 (s, 2H); $^{13}$C{$^1$H}NMR (100 MHz, CDCl$_3$): δ 141.3, 140.7, 138.9, 136.6, 136.4, 131.7, 130.7, 128.9, 128.6, 128.6, 128.0, 127.8, 127.2, 126.5, 126.4, 124.1, 121.2, 120.0, 109.5, 46.9, 37.2; MS (ESI): m/z 349 (M+H)$^+$; HRMS (ESI): m/z calcd for C$_{25}$H$_{21}$N$_2$ (M+H)$^+$: 349.1699, found: 349.1695.

4-Benzyl-9-(phenylsulfonyl)-9H-pyrido[3,4-b]indole (3m)

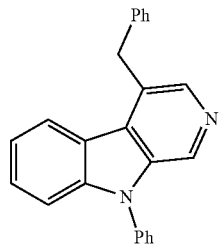 [SMILES: c1ccc(Cc2cncc3c2c2ccccc2n3-c2ccccc2)cc1]

1-Phenyl-1H-indole-2-carbaldehyde (1d, 132 mg, 0.60 mmol), 3-phenylprop-2-yn-1-amine hydrochloride (2b, 150 mg, 0.90 mmol) and NaHCO$_3$ (151 mg, 1.80 mmol) in DMF (3 mL) were stirred for 3 h at room temperature followed by 6 h at 80° C. After column chromatography (CH$_2$Cl$_2$/MeOH 100:0 to 99:1), 166 mg (83%) of a pale, yellow solid was obtained. R$_f$=0.5 (CH$_2$Cl$_2$/MeOH 95:5), mp=141-142° C.; $^1$H NMR (400 MHz, CDCl$_3$): δ 8.75 (s, 1H), 8.32 (s, 1H), 8.07 (d, J=8.0 Hz, 1H), 7.67-7.61 (m, 2H), 7.60-7.55 (m, 2H), 7.53-7.47 (m, 3H), 7.32-7.26 (m, 4H), 7.26-7.17 (m, 2H), 4.66 (s, 2H); $^{13}$C{$^1$H}NMR (100 MHz, CDCl$_3$): δ 141.6, 141.4, 138.9, 137.0, 136.7, 131.7, 130.1, 129.0, 128.6, 128.5, 128.1, 128.0, 127.5, 127.1, 126.4, 123.9, 121.4, 120.6, 110.3, 37.2; FTIR (neat): 3055, 2926, 1595, 1500, 1403, 1325, 1252, 1132, 1025, 869, 743, 730, 698 cm$^{-1}$; MS (ESI): m/z 335 (M+H)$^+$; HRMS (ESI): m/z calcd for C$_{24}$H$_{19}$N$_2$ (M+H)$^+$: 335.1543, found: 335.1547.

tert-Butyl 4-benzyl-9H-pyrido[3,4-b]indole-9-carboxylate (3n)

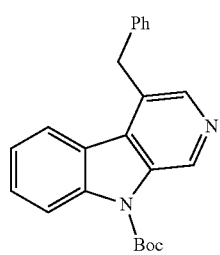 [SMILES: CC(C)(C)OC(=O)n1c2ccccc2c2c(Cc3ccccc3)cncc21]

tert-Butyl 2-formyl-1H-indole-1-carboxylate (1e, 147 mg, 0.60 mmol), 3-phenylprop-2-yn-1-amine hydrochloride (2b, 150 mg, 0.90 mmol) and NaHCO$_3$ (151 mg, 1.80 mmol) in DMF (3 mL) were stirred for 3 h at room temperature 6 h at 80° C. After column chromatography (CH$_2$Cl$_2$/MeOH 100:0 to 99:1), 189 mg (88%) of a pale, yellow solid was obtained. R$_f$=0.6 (CH$_2$Cl$_2$/MeOH 95:5), mp=157-159° C.; $^1$H NMR (400 MHz, CDCl$_3$): δ 9.58 (s, 1H), 8.47 (d, J=8.5 Hz, 1H), 8.40 (s, 1H), 7.96 (d, J=7.9 Hz, 1H), 7.59 (ddd, J=8.5, 7.3, 1.2 Hz, 1H), 7.34-7.27 (m, 3H), 7.25-7.18 (m, 3H), 4.61 (s, 2H), 1.81 (s, 9H); $^{13}$C{$^1$H}NMR (100 MHz, CDCl$_3$): 5150.4, 144.5, 139.2, 138.4, 136.9, 134.8, 130.4, 129.1, 128.7, 128.5, 128.4, 126.5, 123.8, 123.5, 123.4, 116.4, 84.9, 36.9, 28.3; FTIR (neat): 3058, 2972, 1720, 1452, 1423, 1349, 1312, 1251, 1149, 1120, 824, 741, 701 cm$^{-1}$; MS (ESI): m/z 359 (M+H)$^+$; HRMS (ESI): m/z calcd for C$_{23}$H$_{23}$N$_2$O$_2$ (M+H)$^+$: 359.1754, found: 359.1748.

4-Benzyl-9-tosyl-9H-pyrido[3,4-b]indole (3o)

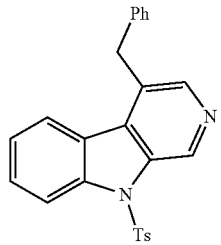 [SMILES: Cc1ccc(S(=O)(=O)n2c3ccccc3c3c(Cc4ccccc4)cncc32)cc1]

1-Tosyl-1H-indole-2-carbaldehyde (1f, 179 mg, 0.60 mmol), 3-phenylprop-2-yn-1-amine hydrochloride (2b, 150 mg, 0.90 mmol) and NaHCO$_3$ (151 mg, 1.80 mmol) in DMF (3 mL) were stirred for 3 h at room temperature followed by 6 h at 80° C. After column chromatography (CH$_2$Cl$_2$/MeOH 100:0 to 99:1), 176 mg (83%) of a white solid was obtained. R$_f$=0.6 (CH$_2$Cl$_2$/MeOH 95:5), mp=147-148° C.; $^1$H NMR (400 MHz, CDCl$_3$): δ 9.62 (s, 1H), 8.41 (d, J=8.5 Hz, 1H), 8.36 (s, 1H), 7.88 (d, J=7.6 Hz, 1H), 7.81-7.70 (m, 2H), 7.66-7.51 (m, 1H), 7.35-7.29 (m, 1H), 7.29-7.17 (m, 3H), 7.14 (dd, J=8.4, 7.8 Hz, 4H), 4.50 (s, 2H), 2.30 (s, 3H); $^{13}$C{$^1$H}NMR (100 MHz, CDCl$_3$): δ 145.4, 145.2, 138.9, 137.9, 135.6, 134.7, 134.5, 131.0, 129.9, 129.4, 129.0, 128.7, 128.4, 126.6, 126.6, 124.4, 124.2, 123.9, 115.0, 36.8, 21.5; FTIR (neat): 3058, 2965, 1642, 1535, 1464, 1356, 1211, 1189, 1017, 936, 759, 690 cm$^{-1}$; MS (ESI): m/z 413 (M+H)$^+$; HRMS (ESI): m/z calcd for C$_{25}$H$_{21}$N$_2$O$_2$S (M+H)$^+$: 413.1318, found: 413.1319.

5-Methoxy-4,9-dimethyl-9H-pyrido[3,4-b]indole (3p)

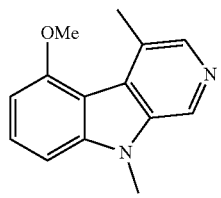

4-Methoxy-1-methyl-1H-indole-2-carbaldehyde (1 g, 113 mg, 0.60 mmol), propargylamine (2a, 49.5 mg, 0.90 mmol) and NaHCO$_3$ (101 mg, 1.20 mmol) in DMF (3 mL) were stirred for 3 h at room temperature followed by 6 h at 80° C. After column chromatography (gradient: CH$_2$Cl$_2$/MeOH 100:0 to 99:1) 120 mg (88%) of a pale, yellow solid was obtained. R$_f$=0.5 (CH$_2$Cl$_2$/MeOH 95:5), mp=153-155° C.; $^1$H NMR (400 MHz, CDCl$_3$): δ 8.66 (s, 1H), 8.22 (s, 1H), 7.50 (t, J=8.1 Hz, 1H), 7.03 (d, J=8.2, 1H), 6.68 (d, J=7.8 Hz, 1H), 4.01 (s, 3H), 3.87 (s, 3H), 2.92 (s, 3H); $^{13}$C{$^1$H}NMR (100 MHz, CDCl$_3$): δ 155.9, 143.3, 141.1, 136.2, 129.3, 129.0, 127.3, 126.9, 111.2, 101.8, 100.5, 55.0, 29.5, 20.4; FTIR (neat): 2925, 1616, 1577, 1464, 1337, 1267, 1074, 785, 712 cm$^{-1}$; MS (ESI): m/z 227 (M+H)$^+$.

4,8,9-Trimethyl-9H-pyrido[3,4-b]indole (3q)

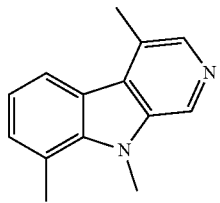 [SMILES: Cc1cncc2c1c1cccc(C)c1n2C]

1,7-Dimethyl-1H-indole-2-carbaldehyde (1h, 103 mg, 0.60 mmol), propargylamine (2a, 49.5 mg, 0.90 mmol) and NaHCO$_3$ (101 mg, 1.20 mmol) in DMF (3 mL) were stirred for 3 h at room temperature followed by 6 h at 80° C. After column chromatography (gradient: CH$_2$Cl$_2$/MeOH 100:0 to 99:1) 105 mg (83%) of a pale, yellow solid was obtained. R$_f$=0.5 (CH$_2$Cl$_2$/MeOH 95:5), mp=137-139° C.; $^1$H NMR (400 MHz, CDCl$_3$): δ 8.60 (s, 1H), 8.16 (s, 1H), 7.94 (d, J=7.7 Hz, 1H), 7.22 (d, J=7.2 Hz, 1H), 7.10 (t, J=7.6 Hz, 1H), 4.01 (s, 3H), 2.78 (s, 3H), 2.70 (s, 3H); $^{13}$C{$^1$H}NMR (100 MHz, CDCl$_3$): δ 140.0, 139.5, 137.0, 130.4, 129.6, 126.6, 126.4, 122.3, 121.5, 120.8, 119.5, 32.3, 20.3, 17.3; FTIR (neat): 3250, 2923, 1609, 1458, 1377, 1262, 1114, 950, 850, 745 cm$^{-1}$; MS (ESI): m/z 211 (M+H)$^+$.

6-Bromo-4,9-dimethyl-9H-pyrido[3,4-b]indole (3r)

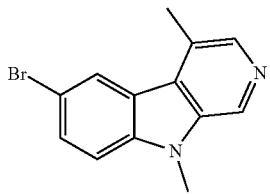 [SMILES: Cc1cncc2c1c1cc(Br)ccc1n2C]

5-Bromo-1-methyl-1H-indole-2-carbaldehyde (1i, 141 mg, 0.60 mmol), propargylamine (2a, 49.5 mg, 0.90 mmol) and NaHCO$_3$ (101 mg, 1.20 mmol) in DMF (3 mL) were stirred for 3 h at room temperature followed by 6 h at 80° C. After column chromatography (gradient: CH$_2$Cl$_2$/MeOH 100:0 to 99:1), 130 mg (70%) of a pale, yellow solid was obtained. R$_f$=0.5 (CH$_2$Cl$_2$/MeOH 95:5), mp=133-135° C.; $^1$H NMR (400 MHz, CDCl$_3$): δ 8.66 (s, 1H), 8.21 (d, J=0.6 Hz, 1H), 8.15 (d, J=1.7 Hz, 1H), 7.62 (dd, J=8.7, 1.9 Hz, 1H), 7.25 (d, J=8.7 Hz, 1H), 3.79 (s, 3H), 2.69 (s, 3H); $^{13}$C{$^1$H}NMR (100 MHz, CDCl$_3$): δ 139.9, 136.5, 130.2, 130.2, 129.8, 126.9, 125.9, 125.7, 123.0, 112.1, 110.3, 29.3, 17.1; FTIR (neat): 2969, 2920, 1629, 1486, 1309, 1268, 1149, 952, 855, 804, 683 cm$^{-1}$; MS (ESI): m/z 275 (M+H)$^+$.

4,6,9-Trimethyl-9H-pyrido[3,4-b]indole (3s)

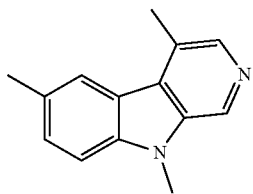 [SMILES: Cc1ccc2c(c1)c1c(C)cncc1n2C]

1,5-Dimethyl-1H-indole-2-carbaldehyde (1j, 103 mg, 0.60 mmol), propargylamine (2a, 49.5 mg, 0.90 mmol) and NaHCO$_3$ (101 mg, 1.20 mmol) in DMF (3 mL) were stirred for 3 h at room temperature followed by 6 h at 80° C. After column chromatography (gradient: CH$_2$Cl$_2$/MeOH 100:0 to 99:1) 109 mg (86%) of a pale, yellow solid was obtained. R$_f$=0.5 (CH$_2$Cl$_2$/MeOH 95:5), mp=122-124° C.; $^1$H NMR (400 MHz, CDCl$_3$): δ 8.63 (s, 1H), 8.18 (d, J=0.5 Hz, 1H), 7.93-7.85 (m, 1H), 7.41-7.34 (m, 1H), 7.27 (d, J=8.4 Hz, 1H), 3.78 (s, 3H), 2.75 (s, 3H), 2.53 (s, 3H); $^{13}$C{$^1$H}NMR (100 MHz, CDCl$_3$): δ 139.7, 139.2, 136.6, 129.4, 128.9, 128.7, 126.8, 126.5, 123.3, 121.6, 108.5, 29.1, 21.4, 17.3; FTIR (neat): 3035, 2915, 1617, 1450, 1349, 1309, 1259, 1059, 857, 805 cm$^{-1}$; MS (ESI): m/z 211 (M+H)$^+$.

4,5-Dimethyl-5H-pyrido[4,3-b]indole (3t)

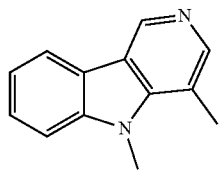

1-Methyl-1H-indole-3-carbaldehyde (1l, 95 mg, 0.60 mmol), propargylamine (2a, 49.5 mg, 0.90 mmol) and NaHCO$_3$ (151 mg, 1.20 mmol) in DMF (3 mL) were stirred for 3 h at room temperature followed by 6 h at 80° C. After column chromatography (CH$_2$Cl$_2$/MeOH 100:0 to 99:1), 108 mg (92%) of a pale, yellow solid was obtained. R$_f$=0.4 (CH$_2$Cl$_2$/MeOH 95:5), mp=129-130° C.; $^1$H NMR (400 MHz, CDCl$_3$): δ 9.13 (s, 1H), 8.22 (s, 1H), 8.09 (d, J=7.7 Hz, 1H), 7.51 (t, J=7.7 Hz, 1H), 7.36 (d, J=8.2 Hz, 1H), 7.29 (t, J=7.5 Hz, 1H), 4.02 (s, 3H), 2.74 (s, 3H); $^{13}$C{$^1$H}NMR (100 MHz, CDCl$_3$): δ 146.7, 143.6, 141.1, 141.1, 126.5, 121.2, 120.4, 120.2, 119.3, 115.0, 108.8, 31.7, 17.0; FTIR (neat): 3048, 2960, 2924, 1584, 1457, 1350, 1238, 1152, 1050, 910, 878, 771, 668 cm$^{-1}$; MS (ESI): m/z 197 (M+H)$^+$; HRMS (ESI): m/z calcd for C$_{13}$H$_{13}$N$_2$ (M+H)$^+$: 197.1073, found: 197.1071.

4-Benzyl-5-methyl-5H-pyrido[4,3-b]indole (3u)

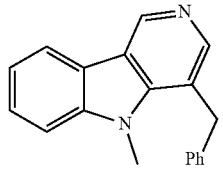 [SMILES: Cn1c2ccccc2c2cncc(Cc3ccccc3)c21]

1-Methyl-1H-indole-3-carbaldehyde (1l, 95 mg, 0.60 mmol), 3-phenylprop-2-yn-1-amine hydrochloride (2b, 150 mg, 0.90 mmol) and NaHCO$_3$ (151 mg, 1.80 mmol) in DMF (3 mL) were stirred for 3 h at room temperature followed by 6 h at 80° C. After column chromatography (CH$_2$Cl$_2$/MeOH 100:0 to 99:1), 141 mg (87%) of a pale, yellow solid was obtained. R$_f$=0.6 (CH$_2$Cl$_2$/MeOH 95:5), mp=127-129° C.; $^1$H NMR (400 MHz, CDCl$_3$): δ 9.31 (s, 1H), 8.38 (s, 1H), 8.19 (d, J=7.7 Hz, 1H), 7.54 (t, J=7.7 Hz, 1H), 7.42-7.19 (m, 5H), 7.12 (d, J=7.3 Hz, 2H), 4.55 (s, 2H), 3.82 (s, 3H); $^{13}$C{$^1$H}NMR (100 MHz, CDCl$_3$): δ 147.9, 143.6, 141.9, 141.2, 140.4, 128.8, 128.0, 126.7, 126.5, 121.3, 120.6, 120.3, 120.0, 116.8, 109.0, 36.2, 31.5; FTIR (neat): 3030, 2924, 2856, 1585, 1480, 1332, 1288, 1123, 1051, 881, 778, 695 cm$^{-1}$; MS (ESI): m/z 273 (M+H)$^+$; HRMS (ESI): m/z calcd for C$_{19}$H$_{17}$N$_2$ (M+H)$^+$: 273.1386, found: 273.1383.

4-Benzyl-5H-pyrido[4,3-b]indole (3v)

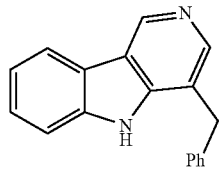 [SMILES: c1ccc(Cc2cncc3c2[nH]c2ccccc23)cc1]

1H-Indole-3-carbaldehyde (1m, 87 mg, 0.60 mmol), 3-phenylprop-2-yn-1-amine hydrochloride (2b, 150 mg, 0.90 mmol) and NaHCO$_3$ (151 mg, 1.80 mmol) in DMF (3 mL) were stirred for 3 h at room temperature followed by 21 h at 80° C. After column chromatography (CH$_2$Cl$_2$/MeOH 100:0 to 99:1), 106 mg (69%) of a yellow solid was obtained. R$_f$=0.3 (CH$_2$Cl$_2$/MeOH 95:5), mp=197-198° C.; $^1$H NMR (400 MHz, DMSO-d$_6$): δ 9.22 (s, 1H), 8.29 (s, 1H), 8.22 (d, J=7.8 Hz, 1H), 7.59 (d, J=8.1 Hz, 1H), 7.48 (dd, J=11.2, 4.0 Hz, 1H), 7.36 (d, J=7.2 Hz, 2H), 7.33-7.23 (m, 3H), 7.19 (t, J=7.2 Hz, 1H), 4.30 (s, 2H); $^{13}$C{$^1$H}NMR (100 MHz, DMSO-d$_6$): δ 144.6, 142.6, 141.0 (d, J=21.2 Hz), 139.9, 139.7, 128.5, 128.5, 128.5, 126.6, 126.2, 121.0, 120.7, 120.0, 119.2, 119.1, 111.6, 33.9; FTIR (neat): 3055, 2974, 2808, 1599, 1494, 1409, 1330, 1219, 1112, 1031, 731, 692 cm$^{-1}$; MS (ESI): m/z 259 (M+H)$^+$; HRMS (ESI): m/z calcd for C$_{18}$H$_{15}$N$_2$ (M+H)$^+$: 259.1230, found: 259.1232.

4-Benzyl-7-bromo-5H-pyrido[4,3-b]indole (3w)

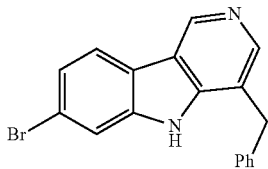 [SMILES: Brc1ccc2c(c1)[nH]c1c(Cc3ccccc3)cncc12]

6-Bromo-1H-indole-3-carbaldehyde (1n, 133 mg, 0.60 mmol), 3-phenylprop-2-yn-1-amine hydrochloride (2b, 150 mg, 0.90 mmol) and NaHCO$_3$ (151 mg, 1.80 mmol) in DMF (3 mL) were stirred for 3 h at room temperature followed by 21 h at 80° C. After column chromatography (CH$_2$Cl$_2$/MeOH 100:0 to 99:1), 151 mg (75%) of a yellow solid was obtained. R$_f$=0.3 (CH$_2$Cl$_2$/MeOH 95:5), mp=191-192° C.; $^1$H NMR (400 MHz, CDCl$_3$: DMSO-d$_6$, 1:1): δ 11.51 (bs, 1H), 9.15 (s, 1H), 8.29 (s, 1H), 8.00 (dt, J=8.6, 4.3 Hz, 1H), 7.82 (d, J=2.4 Hz, 1H), 7.68 (t, J=1.8 Hz, 1H), 7.35 (dt, J=8.3, 2.1 Hz, 1H), 7.27 (dd, J=8.1, 5.2 Hz, 3H), 7.23-7.14 (m, 1H), 4.31 (s, 2H); $^{13}$C{$^1$H}NMR (100 MHz, CDCl$_3$: DMSO-d$_6$, 1:1): δ 143.9, 142.2, 139.8, 139.7, 138.1, 127.3, 127.2, 125.1, 121.9, 120.5, 119.2, 118.3, 117.8, 117.7, 113.3, 33.2; FTIR (neat): 3032, 2956, 2813, 1549, 1439, 1405, 1356, 1213, 1091, 913, 856, 779, 696 cm$^{-1}$; MS (ESI): m/z 337 (M+H)$^+$; HRMS (ESI): m/z calcd for C$_{18}$H$_{14}$BrN$_2$ (M+H)$^+$: 337.0335, found: 337.0343.

4-Benzyl-5H-pyrido[4,3-b]indole-8-carbonitrile (3x)

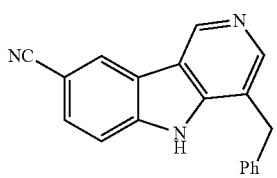 [SMILES: N#Cc1ccc2[nH]c3c(Cc4ccccc4)cncc3c2c1]

3-Formyl-1H-indole-5-carbonitrile (1o, 102 mg, 0.60 mmol), 3-phenylprop-2-yn-1-amine hydrochloride (2b, 150 mg, 0.90 mmol) and NaHCO$_3$ (151 mg, 1.80 mmol) in DMF (3 mL) were stirred for 21 h at room temperature followed by 6 h at 80° C. After column chromatography (CH$_2$Cl$_2$/MeOH 100:0 to 99:1), 113 mg (67%) of a pale, yellow solid was obtained. R$_f$=0.2 (CH$_2$Cl$_2$/MeOH 95:5), mp=179-180° C.; $^1$H NMR (400 MHz, DMSO-d$_6$): δ 9.35 (s, 1H), 8.83 (s, 1H), 8.40 (s, 1H), 7.86 (dd, J=8.5, 1.3 Hz, 1H), 7.73 (d, J=8.5 Hz, 1H), 7.40-7.25 (m, 4H), 7.20 (t, J=7.1 Hz, 1H), 4.32 (s, 2H); $^{13}$C{$^1$H}NMR (100 MHz, DMSO-d$_6$): δ 145.9, 143.4, 141.9, 139.6, 129.7, 128.5, 128.5, 128.4, 126.3, 126.2, 121.3, 120.1, 119.7, 118.4, 112.7, 102.0, 33.8; FTIR (neat): 3032, 2920, 2813, 2223, 1585, 1477, 1411, 1243, 1221, 1120, 884, 819, 742, 696 cm$^{-1}$; MS (ESI): m/z 284 (M+H)$^+$; HRMS (ESI): m/z calcd for C$_{19}$H$_{14}$N$_3$ (M+H)$^+$: 284.1182, found: 284.1185.

9-Benzyl-1,2,3,10-tetrahydrocyclopenta[g]pyrido[4,3-b]indole (3y)

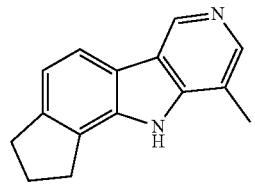 [SMILES: Cc1cncc2c1[nH]c1c3c(ccc12)CCC3]

1, 6, 7, 8-Tetrahydrocyclopenta[g]indole-3-carbaldehyde (1p, 111 mg, 0.60 mmol), 3-phenylprop-2-yn-1-amine hydrochloride (2b, 150 mg, 0.90 mmol) and NaHCO$_3$ (101 mg, 1.20 mmol) in DMF (3 mL) were stirred for 21 h at room temperature followed by 6 h at 80° C. After column chromatography (CH$_2$Cl$_2$/MeOH 100:0 to 99:1), 102 mg (77%) of a pale, yellow solid was obtained. R$_f$=0.3 (CH$_2$Cl$_2$/MeOH 95:5), mp=183-184° C.; $^1$H NMR (400 MHz, DMSO-d$_6$): δ 11.49 (bs, 1H), 9.13 (s, 1H), 8.21 (s, 1H), 7.97 (d, J=7.9 Hz, 1H), 7.15 (d, J=7.9 Hz, 1H), 3.16 (t, J=7.3 Hz, 2H), 3.04 (t, J=7.4 Hz, 2H), 2.54 (s, 3H), 2.27-2.13 (m, 2H); $^{13}$C{$^1$H}NMR (100 MHz, DMSO-d$_6$): δ 143.8, 143.4, 142.8, 140.0, 136.6, 125.8, 119.5, 119.3, 118.5, 116.7, 115.7, 33.0, 30.2, 25.1, 14.3; FTIR (neat): 2922, 2851, 1578, 1456, 1378, 1252, 1224, 1109, 804, 686 cm$^{-1}$; MS (ESI): m/z 223 (M+H)$^+$; HRMS (ESI): m/z calcd for C$_{15}$H$_{15}$N$_2$ (M+H)$^+$: 223.1230, found: 223.1232.

4-Benzylbenzofuro[2,3-c]pyridine (4a)

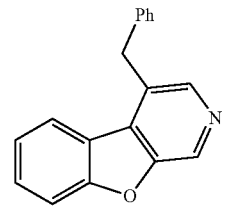 [SMILES: c1ccc(Cc2cncc3oc4ccccc4c23)cc1]

Benzofuran-2-carbaldehyde (1q, 88 mg, 0.60 mmol), 3-phenylprop-2-yn-1-amine hydrochloride (2b, 150 mg, 0.90 mmol) and NaHCO$_3$ (151 mg, 1.80 mmol) in DMF (3 mL) were stirred for 3 h at room temperature followed by 6 h at 80° C. After column chromatography (EtOAc/hexanes 10:90 to 40:60), 122 mg (79%) of a white solid was obtained. R$_f$=0.2 (EtOAc/hexanes 30:70), mp=110-112° C.; $^1$H NMR (400 MHz, CDCl$_3$): δ 8.92 (s, 1H), 8.40 (s, 1H), 7.88-7.81 (m, 1H), 7.66-7.62 (m, 1H), 7.56 (ddd, J=8.4, 7.3, 1.3 Hz, 1H), 7.35-7.25 (m, 3H), 7.25-7.19 (m, 3H), 4.53 (s, 2H); $^{13}C\{^{1}H\}$NMR (100 MHz, CDCl$_3$): δ 156.6, 152.6, 144.1, 138.3, 132.7, 130.0, 129.8, 129.4, 128.7, 128.4, 126.6, 123.7, 123.4, 122.2, 112.3, 36.7; FTIR (neat): 3023, 2921, 2852, 1625, 1448, 1416, 1268, 1201, 1151, 1041, 847, 751, 702 cm$^{-1}$; MS (ESI): m/z 260 (M+H)$^+$; HRMS (ESI): m/z calcd for C$_{18}$H$_{14}$NO (M+H)$^+$: 260.1070, found: 260.1066.

4-Benzylbenzo[4,5]thieno[2,3-c]pyridine (4b)

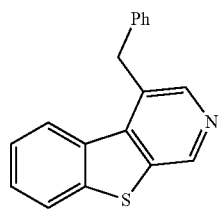 [SMILES: c1ccc(Cc2cncc3sc4ccccc4c23)cc1]

Benzo[b]thiophene-2-carbaldehyde (1r, 97 mg, 0.60 mmol), 3-phenylprop-2-yn-1-amine hydrochloride (2b, 150 mg, 0.90 mmol) and NaHCO$_3$ (151 mg, 1.80 mmol) in DMF (3 mL) were stirred for 3 h at room temperature followed by 6 h at 80° C. After column chromatography (EtOAc/hexanes 10:90 to 40:60), 136 mg (83%) of a pale, yellow solid was obtained. R$_f$=0.2 (EtOAc/hexanes 30:70), mp=103-104° C.; $^1$H NMR (400 MHz, CDCl$_3$) δ 9.09 (s, 1H), 8.40 (s, 1H), 8.16 (d, J=8.2 Hz, 1H), 7.91 (d, J=7.8 Hz, 1H), 7.51 (ddd, J=8.2, 7.2, 1.1 Hz, 1H), 7.37 (ddd, J=8.3, 7.2, 1.1 Hz, 1H), 7.30-7.26 (m, 2H), 7.24-7.13 (m, 3H), 4.64 (s, 2H); $^{13}C\{^{1}H\}$NMR (100 MHz, CDCl$_3$): δ 146.3, 143.4, 141.1, 140.1, 138.1, 136.0, 133.9, 130.3, 128.8, 128.3, 128.2, 126.6, 126.4, 124.8, 123.2, 37.7; FTIR (neat): 3027, 2922, 2851, 1493, 1441, 1405, 1254, 1228, 1132, 1072, 882, 735, 696 cm$^{-1}$; MS (ESI): m/z 276 (M+H)$^+$; HRMS (ESI): m/z calcd for C$_{18}$H$_{14}$NS (M+H)$^+$: 276.0841, found: 276.0839.

tert-Butyl 8-benzyl-9H-pyrrolo[2,3-b:4,5-c']dipyridine-9-carboxylate (4c)

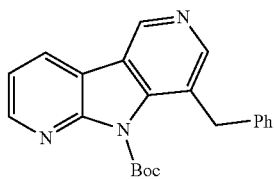 [SMILES: CC(C)(C)OC(=O)n1c2ncccc2c2cncc(Cc3ccccc3)c21]

tert-Butyl 3-formyl-1H-pyrrolo[2,3-b]pyridine-1-carboxylate (1s, 147 mg, 0.60 mmol), 3-phenylprop-2-yn-1-amine hydrochloride (2b, 150 mg, 0.90 mmol) and NaHCO$_3$ (151 mg, 1.80 mmol) in DMF (3 mL) were stirred for 3 h at room temperature followed by 6 h at 80° C. After column chromatography (CH$_2$Cl$_2$/MeOH 100:0 to 99:1), 174 mg (81%) of a pale, yellow solid was obtained. R$_f$=0.4 (CH$_2$Cl$_2$/MeOH 95:5), mp=137-138° C.; $^1$H NMR (400 MHz, CDCl$_3$): δ 9.22 (s, 1H), 8.55 (dd, J=4.8, 1.7 Hz, 1H), 8.47 (s, 1H), 8.35 (dd, J=7.7, 1.7 Hz, 1H), 7.34 (dd, J=7.7, 4.8 Hz, 1H), 7.24-7.17 (m, 3H), 7.05 (d, J=6.8 Hz, 2H), 4.46 (s, 2H), 1.59 (s, 9H); $^{13}C\{^{1}H\}$NMR (100 MHz, CDCl$_3$): δ 151.6, 149.7, 149.2, 148.0, 141.5, 141.2, 138.7, 132.6, 128.5, 128.4, 126.4, 121.7, 119.2, 118.9, 115.5, 85.5, 37.0, 27.8; FTIR (neat): 3063, 2976, 2925, 1739, 1576, 1495, 1400, 1254, 11456, 892, 757, 706 cm$^{-1}$; MS (ESI): m/z 360 (M+H)$^+$; HRMS (ESI): m/z calcd for C$_{22}$H$_{22}$N$_3$O$_2$ (M+H)$^+$: 360.1707. found: 360.1709.

4-Benzyl-1-methyl-1H-pyrrolo[2,3-c]pyridine (4d)

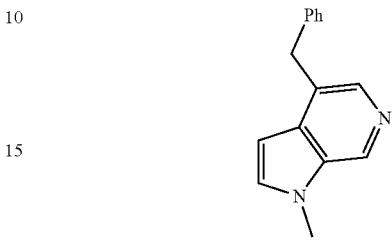

1-Methyl-1H-pyrrole-2-carbaldehyde (1t, 65 mg, 0.60 mmol), 3-phenylprop-2-yn-1-amine hydrochloride (2b, 150 mg, 0.90 mmol) and NaHCO$_3$ (151 mg, 1.80 mmol) in DMF (3 mL) were stirred for 3 h at room temperature followed by 6 h at 80° C. After column chromatography (CH$_2$Cl$_2$/MeOH 100:0 to 99:1), 62 mg (62%) of a pale, yellow solid was obtained. R$_f$=0.1 (CH$_2$Cl$_2$/MeOH 95:5), mp=107-108° C.; $^1$H NMR (400 MHz, CDCl$_3$): δ 8.66 (s, 1H), 8.13 (s, 1H), 7.28-7.22 (m, 4H), 7.20-7.15 (m, 1H), 7.12 (d, J=3.0 Hz, 1H), 6.37 (dd, J=3.0, 0.5 Hz, 1H), 4.23 (s, 2H), 3.88 (s, 3H); $^{13}C\{^{1}H\}$NMR (100 MHz, CDCl$_3$): δ 140.3, 138.5, 133.0, 132.0, 131.3, 128.7, 128.4, 128.4, 127.5, 126.1, 99.4, 37.2, 33.2; FTIR (neat): 3019, 2917, 2850, 1669, 1503, 1447, 1350, 1251, 1117, 1080, 864, 758, 699 cm$^{-1}$; MS (ESI): m/z 223 (M+H)$^+$; HRMS (ESI): m/z calcd for C$_{15}$H$_{15}$N$_2$ (M+H)$^+$: 223.1230, found: 223.1228.

4-Benzyl-2-methylfuro[2,3-c]pyridine (4t)

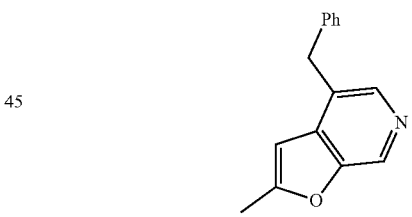

5-Methylfuran-2-carbaldehyde (1u, 66 mg, 0.60 mmol), 3-phenylprop-2-yn-1-amine hydrochloride (2b, 150 mg, 0.90 mmol) and NaHCO$_3$ (151 mg, 1.80 mmol) in DMF (3 mL) were stirred for 3 h at room temperature followed by 6 h at 80° C. After column chromatography (CH$_2$Cl$_2$/MeOH 100:0 to 99:1), 115 mg (86%) of a white solid was obtained. R$_f$=0.7 (CH$_2$Cl$_2$/MeOH 95:5), mp=119-120° C.; $^1$H NMR (400 MHz, CDCl$_3$): δ 8.65 (s, 1H), 8.25 (s, 1H), 7.31-7.25 (m, 2H), 7.24-7.17 (m, 3H), 6.25 (s, 1H), 4.16 (s, 2H), 2.45 (d, J=1.0 Hz, 3H); $^{13}C\{^{1}H\}$NMR (100 MHz, CDCl$_3$): δ 158.9, 142.3, 139.6, 135.3, 131.3, 128.7, 128.6, 128.6, 128.0, 126.4, 101.1, 37.0, 14.2; FTIR (neat): 3026, 2919, 2851, 1594, 1494, 1417, 1264, 1205, 1030, 939, 865, 730, 698 cm$^{-1}$; MS (ESI): m/z 224 (M+H)$^+$; HRMS (ESI): m/z calcd for C$_{15}$H$_{14}$NO (M+H)$^+$: 224.1070, found: 224.1067.

4-Benzylthieno[2,3-c]pyridine (4f)

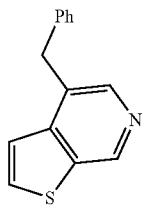 [SMILES: c1ccc(Cc2cncc3sccc23)cc1]

Thiophene-2-carbaldehyde (1v, 67 mg, 0.60 mmol), 3-phenylprop-2-yn-1-amine hydrochloride (2b, 150 mg, 0.90 mmol) and NaHCO$_3$ (151 mg, 1.80 mmol) in DMF (3 mL) were stirred for 3 h at room temperature followed by 6 h at 80° C. After column chromatography (CH$_2$Cl$_2$/MeOH 100:0 to 99:1), 101 mg (75%) of a pale, yellow solid was obtained. R$_f$=0.7 (CH$_2$Cl$_2$/MeOH 95:5), mp=147-148° C.; $^1$H NMR (400 MHz, CDCl$_3$): δ 9.09 (s, 1H), 8.38 (s, 1H), 7.67 (d, J=5.4 Hz, 1H), 7.34 (d, J=5.4 Hz, 1H), 7.31-7.24 (m, 2H), 7.21 (t, J=6.7 Hz, 3H), 4.31 (s, 2H); $^{13}$C{$^1$H}NMR (100 MHz, CDCl$_3$): 5144.4, 143.1, 142.9, 139.4, 132.0, 130.2, 128.6, 128.6, 128.4, 126.5, 121.6, 37.4; FTIR (neat): 3097, 3084, 2920, 1567, 1491, 1401, 1340, 1257, 1225, 957, 779, 746, 695 cm$^{-1}$; MS (ESI): m/z 226 (M+H)$^+$; HRMS (ESI): m/z calcd for C$_{14}$H$_{12}$NS (M+H)$^+$: 226.0685, found: 226.0681.

7-Methyl-1,9-phenanthroline (4g)

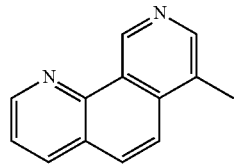

Quinoline-8-carbaldehyde (1w, 94 mg, 0.60 mmol), propargylamine (2a, 49.5 mg, 0.90 mmol) and NaHCO$_3$ (101 mg, 1.20 mmol) in DMF (3 mL) were stirred for 3 h at room temperature followed by 6 h at 80° C. After column chromatography (CH$_2$Cl$_2$/MeOH 100:0 to 99:1), 73 mg (63%) of a pale, yellow solid was obtained. R$_f$=0.5 (CH$_2$Cl$_2$/MeOH 95:5), mp=151-152° C.; $^1$H NMR (400 MHz, CDCl$_3$): δ 10.47 (s, 1H), 9.08 (dd, J=4.4, 1.8 Hz, 1H), 8.67 (d, J=0.7 Hz, 1H), 8.24 (dd, J=8.1, 1.8 Hz, 1H), 7.96 (s, 2H), 7.60 (dd, J=8.1, 4.4 Hz, 1H), 2.72 (s, 3H); $^{13}$C{$^1$H}NMR (100 MHz, CDCl$_3$): 5150.1, 147.3, 146.8, 146.3, 136.4, 135.9, 129.9, 127.3, 126.1, 125.2, 122.5, 122.3, 16.2; FTIR (neat): 3050, 2936, 2925, 1725, 1539, 1487, 1439, 1254, 1453, 903, 765, 720 cm$^{-1}$; MS (ESI): m/z 195 (M+H)$^+$; HRMS (ESI): m/z calcd for C$_{13}$H$_{11}$N$_2$ (M+H)$^+$: 195.0917, found: 195.0913.

4-Methylbenzo[h]isoquinoline (4h)

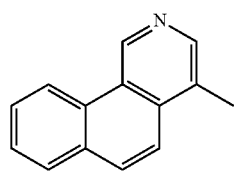

1-Naphthaldehyde (1x, 94 mg, 0.60 mmol), propargylamine (2a, 49.5 mg, 0.90 mmol) and NaHCO$_3$ (101 mg, 1.20 mmol) in DMF (3 mL) were stirred for 3 h at room temperature followed by 6 h at 80° C. After column chromatography (EtOAc/hexanes 10:90 to 40:60), 101 mg (87%) of a pale, yellow solid was obtained. R$_f$=0.3 (EtOAc/hexanes 30:70), mp=126-127° C.; $^1$H NMR (400 MHz, CDCl$_3$): δ 9.96 (s, 1H), 8.82 (d, J=8.3 Hz, 1H), 8.57 (s, 1H), 8.02 (d, J=9.1 Hz, 1H), 7.96 (dd, J=7.9, 1.2 Hz, 1H), 7.89 (d, J=9.1 Hz, 1H), 7.76 (ddd, J=8.4, 7.1, 1.4 Hz, 1H), 7.68 (ddd, J=8.1, 7.1, 1.2 Hz, 1H), 2.71 (s, 3H); $^{13}$C{$^1$H}NMR (100 MHz, CDCl$_3$): δ 144.8, 144.7, 135.1, 131.8, 131.7, 129.6, 128.9, 128.2, 128.0, 127.4, 124.4, 122.2, 121.1, 16.3; FTIR (neat): 3035, 2980, 2869, 1576, 1475, 1356, 1283, 1136, 996, 789, 699 cm$^{-1}$; MS (ESI): m/z 194 (M+H)$^+$; HRMS (ESI): m/z calcd for C$_{14}$H$_{12}$N (M+H)$^+$: 194.0959, found: 194.0964.

4-Benzylbenzo[h]isoquinoline (4i)

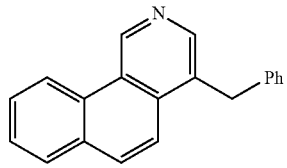 [SMILES: c1ccc(Cc2cncc3c2ccc2ccccc23)cc1]

1-Naphthaldehyde (1x, 94 mg, 0.60 mmol), 3-phenylprop-2-yn-1-amine hydrochloride (2b, 150 mg, 0.90 mmol) and NaHCO$_3$ (151 mg, 1.80 mmol) in DMF (3 mL) were stirred for 3 h at room temperature followed by 6 h at 80° C. After column chromatography (EtOAc/hexanes 10:90 to 40:60), 95 mg (82%) of a pale, yellow solid was obtained. R$_f$=0.3 (EtOAc/hexanes 30:70), mp=115-117° C.; $^1$H NMR (400 MHz, CDCl$_3$): δ 10.05 (s, 1H), 8.85 (d, J=8.3 Hz, 1H), 8.64 (s, 1H), 7.96-7.88 (m, 2H), 7.84 (d, J=9.1 Hz, 1H), 7.80-7.73 (m, 1H), 7.68 (dd, J=11.0, 4.0 Hz, 1H), 7.34-7.26 (m, 2H), 7.22 (dd, J=6.9, 4.4 Hz, 3H), 4.49 (s, 2H); $^{13}$C{$^1$H}NMR (100 MHz, CDCl$_3$): δ 146.1, 145.9, 139.8, 134.7, 131.7, 130.2, 129.7, 128.8, 128.6, 128.6, 128.5, 127.9, 127.4, 126.3, 124.9, 122.2, 121.4, 36.4; FTIR (neat): 3043, 2959, 2876, 1577, 1483, 1371, 1239, 1121, 887, 779, 696 cm$^{-1}$; MS (ESI): m/z 270 (M+H)$^+$; HRMS (ESI): m/z calcd for C$_{20}$H$_{16}$N (M+H)$^+$: 270.1277, found: 270.1278.

4-Methyldibenzo[f,h]isoquinoline (4j)

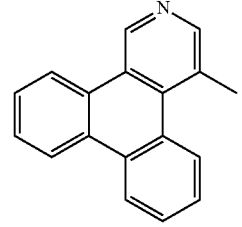 [SMILES: Cc1cncc2c3ccccc3c3ccccc3c12]

Phenanthrene-9-carbaldehyde (1y, 123 mg, 0.60 mmol), propargylamine (2a, 49.5 mg, 0.90 mmol) and NaHCO$_3$ (101 mg, 1.20 mmol) in DMF (3 mL) were stirred for 3 h at room temperature followed by 6 h at 80° C. After column chromatography (CH$_2$Cl$_2$/MeOH 100:0 to 99:1), 123 mg (85%) of a white solid was obtained. R$_f$=0.5 (CH$_2$Cl$_2$/MeOH 95:5), mp=173-175° C.; $^1$H NMR (400 MHz, CDCl$_3$): δ 9.85 (s, 1H), 8.76 (d, J=8.2 Hz, 1H), 8.73-8.68 (m, 2H), 8.66-8.59 (m, 2H), 7.75 (ddd, J=8.3, 7.1, 1.3 Hz, 1H), 7.72-7.62 (m, 3H), 3.04 (s, 3H); $^{13}$C{$^1$H}NMR (100 MHz, CDCl$_3$): δ 150.0, 144.8, 135.1, 132.3, 130.1, 129.0, 128.7, 128.6, 128.5, 128.4, 128.0, 127.9, 126.4, 125.2, 123.5, 123.2, 123.0, 23.6; FTIR (neat): 3057, 2961, 2871, 1587, 1416, 1375, 1249, 1156, 882, 752, 713 cm$^{-1}$; MS (ESI): m/z 244 (M+H)$^+$; HRMS (ESI): m/z calcd for C$_{18}$H$_{14}$N (M+H)$^+$: 244.1121, found: 244.1122.

4-Benzyl-3,9-dimethyl-9H-pyrido[3,4-b]indole (5a)

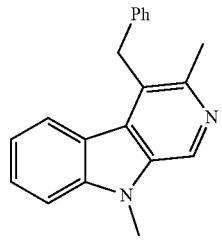 [SMILES: Cc1ncc2c(c1Cc1ccccc1)c1ccccc1n2C]

1-Methyl-1H-indole-2-carbaldehyde (1a, 95 mg, 0.60 mmol), 4-phenylbut-3-yn-2-amine hydrochloride (2 k, 162 mg, 0.90 mmol) and NaHCO$_3$ (151 mg, 1.80 mmol) in DMF (3 mL) were stirred for 3 h at room temperature followed by 6 h at 80° C. After column chromatography (CH$_2$Cl$_2$/MeOH 100:0 to 99:1), 139 mg (81%) of a pale, yellow solid was obtained. R$_f$=0.6 (CH$_2$Cl$_2$/MeOH 95:5), mp=161-163° C.; $^1$H NMR (400 MHz, CDCl$_3$): δ 8.72 (s, 1H), 8.04 (d, J=8.0 Hz, 1H), 7.60-7.51 (m, 1H), 7.44 (d, J=8.3 Hz, 1H), 7.25-7.19 (m, 2H), 7.16 (t, J=7.16 Hz, 4H), 4.65 (s, 2H), 3.92 (s, 3H), 2.66 (s, 3H); $^{13}$C{$^1$H}NMR (100 MHz, CDCl$_3$): δ 146.6, 142.1, 138.4, 136.1, 128.9, 128.6, 128.3, 128.1, 127.7, 126.6, 126.2, 123.8, 121.0, 119.5, 109.0, 35.4, 29.3, 21.5; FTIR (neat): 3026, 2918, 1492, 1452, 1329, 1277, 1074, 938, 742, 729, 696 cm$^{-1}$; MS (ESI): m/z 287 (M+H)$^+$; HRMS (ESI): m/z calcd for C$_{20}$H$_{19}$N$_2$ (M+H)$^+$: 287.1543, found: 287.1547.

3,4,9-Trimethyl-9H-pyrido[3,4-b]indole (5b)

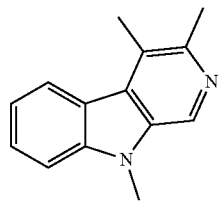 [SMILES: Cc1ncc2c(c1C)c1ccccc1n2C]

1-Methyl-1H-indole-2-carbaldehyde (1a, 95 mg, 0.60 mmol), but-3-yn-2-amine hydrochloride (2j, 94.5 mg, 0.90 mmol) and NaHCO$_3$ (151 mg, 1.80 mmol) in DMF (3 mL) were stirred for 3 h at room temperature followed by 6 h at 80° C. After column chromatography (CH$_2$Cl$_2$/MeOH 100:0 to 99:1), 114 mg (91%) of a pale, yellow solid was obtained. R$_f$=0.6 (CH$_2$Cl$_2$/MeOH 95:5), mp=147-149° C.; $^1$H NMR (400 MHz, CDCl$_3$): δ 8.56 (s, 1H), 8.22 (d, J=8.0 Hz, 1H), 7.59-7.53 (m, 1H), 7.41 (d, J=7.7 Hz, 1H), 7.28-7.23 (m, 1H), 3.82 (s, 3H), 2.76 (s, 3H), 2.69 (s, 3H); $^{13}$C{$^1$H}NMR (100 MHz, CDCl$_3$): δ 145.3, 141.9, 135.8, 127.7, 127.7, 127.4, 124.8, 123.8, 121.6, 119.2, 108.8, 29.1, 21.8, 15.9; FTIR (neat): 3059, 2921, 1620, 1460, 1327, 1282, 1159, 1002, 956, 725 cm$^{-1}$; MS (ESI): m/z 211 (M+H)$^+$; HRMS (ESI): m/z calcd for C$_{14}$H$_{15}$N$_2$ (M+H)$^+$: 211.1230, found: 211.1235.

9-Methyl-4-vinyl-9H-pyrido[3,4-b]indole (5c)

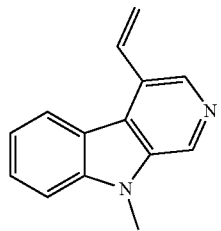 [SMILES: C=Cc1cncc2c1c1ccccc1n2C]

1-Methyl-1H-indole-2-carbaldehyde (1a, 95 mg, 0.60 mmol), 4-chlorobut-2-yn-1-amine hydrochloride (2l, 125 mg, 0.90 mmol) and NaHCO$_3$ (151 mg, 1.80 mmol) in DMF (3 mL) were stirred for 3 h at room temperature followed by 6 h at 80° C. After column chromatography (CH$_2$Cl$_2$/MeOH 100:0 to 99:1), 78 mg (63%) of a pale, yellow solid was obtained. R$_f$=0.4 (CH$_2$Cl$_2$/MeOH 95:5), mp=133-135° C.; $^1$H NMR (400 MHz, CDCl$_3$): δ 8.82 (s, 1H), 8.58 (s, 1H), 8.29 (d, J=8.0 Hz, 1H), 7.68-7.55 (m, 2H), 7.51 (d, J=8.3 Hz, 1H), 7.33 (ddd, J=11.3, 6.2, 2.6 Hz, 1H), 6.00 (dd, J=17.5, 1.3 Hz, 1H), 5.64 (dd, J=11.0, 1.2 Hz, 1H), 3.97 (s, 3H); $^{13}$C{$^1$H}NMR (100 MHz, CDCl$_3$): δ 141.8, 136.7, 136.7, 132.5, 130.6, 128.4, 128.0, 125.3, 124.1, 121.2, 119.8, 118.2, 109.1, 29.4; FTIR (neat): 3050, 2922, 1617, 1466, 1441, 1326, 1264, 1136, 1098, 916, 745, 730 cm$^{-1}$; MS (ESI): m/z 209 (M+H)$^+$; HRMS (ESI): m/z calcd for C$_{14}$H$_{13}$N$_2$ (M+H)$^+$: 209.1073, found: 209.1076.

9-(Methoxymethyl)-4-methyl-9H-pyrido[3,4-b]indole (3z)

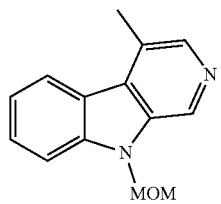

1-(Methoxymethyl)-1H-indole-2-carbaldehyde (1z, 113 mg, 0.60 mmol), propargylamine (2a, 49.5 mg, 0.90 mmol) and NaHCO$_3$ (101 mg, 1.20 mmol) in DMF (3 mL) were stirred for 3 h at room temperature followed by 6 h at 80° C. After column chromatography (CH$_2$Cl$_2$/MeOH 100:0 to 99:1), 126 mg (93%) of a pale, yellow solid was obtained. R$_f$=0.5 (CH$_2$Cl$_2$/MeOH 95:5), mp=128-129° C.; $^1$H NMR (400 MHz, CDCl$_3$): δ 8.88 (s, 1H), 8.30 (s, 1H), 8.22 (d, J=7.9 Hz, 1H), 7.68-7.54 (m, 2H), 7.43-7.31 (m, 1H), 5.74 (s, 2H), 3.30 (s, 3H), 2.84 (s, 3H); $^{13}$C{$^1$H}NMR (100 MHz, CDCl$_3$): δ 141.1, 140.8, 136.3, 130.3, 128.0, 127.7, 127.1, 123.7, 122.4, 120.7, 109.8, 74.3, 56.3, 17.4; FTIR (neat): 2944, 1617, 1451, 1327, 1263, 1135, 1068, 1101, 911, 753, 689 cm$^{-1}$; MS (ESI): m/z 227 (M+H)$^+$; HRMS (ESI): m/z calcd for C$_{14}$H$_{15}$N$_2$O (M+H)$^+$: 227.1179, found: 227.1181.

(E)—N—((1-methyl-1H-indol-2-yl)methylene)prop-2-yn-1-amine (3aa)

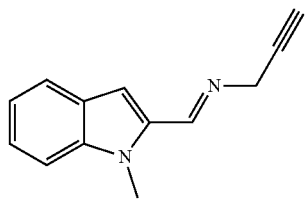

1-Methyl-1H-indole-2-carbaldehyde (1a, 95 mg, 0.60 mmol), propargylamine (2a, 49.5 mg, 0.90 mmol) and 4 Å molecular sieves in DMF (3 mL) were stirred for 3 h at room temperature followed by 6 h at 80° C. After column chromatography (EtOAc/hexanes 1:99 to 5:95), 100 mg (85%) of a pale, yellow solid was obtained. $R_f$=0.5 (EtOAc/hexanes 10:90), mp=102-103° C.; $^1$H NMR (400 MHz, CDCl$_3$): δ 8.65 (t, J=1.8 Hz, 1H), 7.65 (d, J=8.0 Hz, 1H), 7.33 (ddd, J=14.4, 8.3, 4.0 Hz, 2H), 7.12 (t, J=7.4 Hz, 1H), 6.87 (s, 1H), 4.54 (t, J=2.1 Hz, 2H), 4.11 (s, 3H), 2.54 (t, J=2.4 Hz, 1H); $^{13}$C{$^1$H}NMR (100 MHz, CDCl$_3$): δ 155.1, 140.0, 135.1, 126.9, 124.1, 121.8, 120.0, 110.0, 109.7, 79.0, 75.7, 47.5, 31.9; FTIR (neat): 3242, 2940, 2869, 1638, 1469, 1322, 1182, 1122, 1026, 920, 804, 740 cm$^{-1}$; MS (ESI): m/z 197 (M+H)$^+$; HRMS (ESI): m/z calcd for C$_{13}$H$_{13}$N$_2$ (M+H)$^+$: 197.1073, found: 197.1072.

Gram-Scale Synthesis of 3a

Synthesis of Carboline 3a from Imine Intermediate 3aa:

To a stirred solution of imine 3aa (0.6 mmol) in DMF (2 mL) was added NaHCO$_3$ (1.2 mmol) at room temperature under argon. The reaction mixture was stirred for 6 h at 80° C. After completion of the reaction, water (10 mL) was added. The two layers were separated, and the aqueous layer was extracted with EtOAc (2×10 mL). The combined organic layer was washed with ice cold water (2×15 mL), dried over magnesium sulfate and evaporated under reduced pressure. The crude product was purified by flash column chromatography on silica gel to afford β-carboline 3a in 88% yield.

Gram—Scale Synthesis of 3a:

1-Methyl-1H-indole-2-carbaldehyde (1a, 95 mg, 0.60 mmol), propargylamine (2a, 49.5 mg, 0.90 mmol) and NaHCO$_3$ (101 mg, 1.20 mmol) in DMF (3 mL) were stirred for 3 h at room temperature followed by 6 h at 80° C. Column chromatography (CH$_2$Cl$_2$/MeOH 100:0 to 99:1) gave 3a (79%) and 5 (5%).

Synthesis of Oxopropaline Analogue (7)

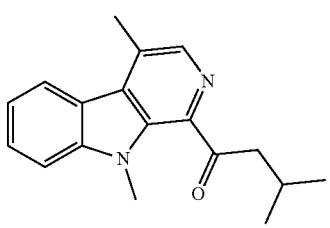 [SMILES: Cc1cnc(C(=O)CC(C)C)c2c1c1ccccc1n2C]

To a solution of 3a (0.2 mmol), isovaleraldehyde (0.8 mmol) and TMSN$_3$ (0.4 mmol) in benzene (1.5 mL), phenyliodinebis(trifluoroacetate) (PIFA) (0.4 mmol) was added portionwise over a 10 minute period at room temperature. After stirring for 2 h at room temperature, triethylamine (0.5 mL) was added and the mixture was stirred for 10 min. The volatiles were removed under reduced pressure. Flash column chromatography (EtOAc/hexanes 1:99 to 5:95) gave the product 7 as a semisolid in 87% yield. $^1$H NMR (400 MHz, CDCl$_3$): δ 8.25 (d, J=0.6 Hz, 1H), 8.18 (d, J=7.9 Hz, 1H), 7.61 (ddd, J=8.3, 7.1, 1.2 Hz, 1H), 7.51 (d, J=8.3 Hz, 1H), 7.32 (ddd, J=8.0, 7.2, 0.9 Hz, 1H), 3.87 (s, 3H), 3.28 (d, J=7.0 Hz, 2H), 2.86 (d, J=0.5 Hz, 3H), 2.47-2.34 (m, 1H), 1.07 (d, J=6.7 Hz, 6H); $^{13}$C{$^1$H}NMR (100 MHz, CDCl$_3$): δ 203.5, 143.2, 138.5, 138.3, 135.0, 130.7, 130.0, 128.2, 123.4, 121.3, 120.2, 109.9, 48.8, 34.0, 25.0, 22.8, 17.8; FTIR (neat): 2954, 2869, 1680, 1615, 1464, 1275, 1183, 1108, 1011, 934, 734 cm$^{-1}$; MS (ESI): m/z 281 (M+H)$^+$; HRMS (ESI): m/z calcd for C$_{18}$H$_{21}$N$_2$O (M+H)$^+$: 281.1648, found: 281.1652.

Example 3

General Method of Preparation of Substituted Pyridines

Representative Substituted Pyridines (8a-8aa):

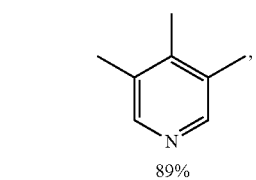

8a

89%

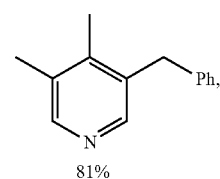

8b

81%

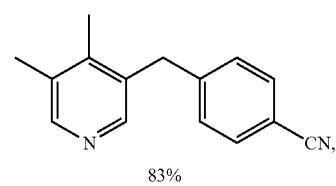

8c

83%

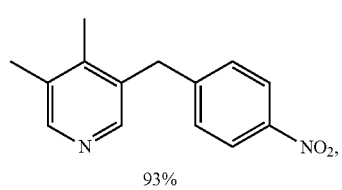

8d

93%

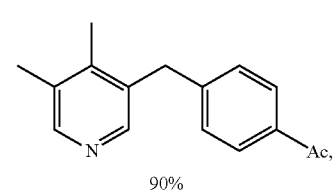

8e

90%

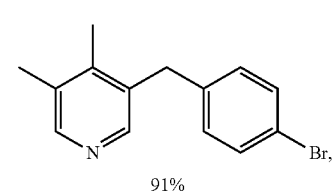

8f

91%

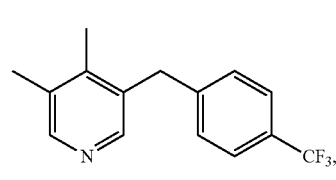

8g

95%

-continued
8h
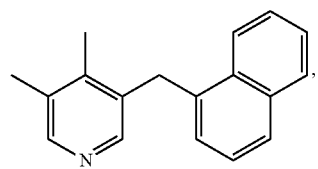
87%
8i
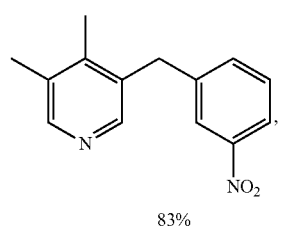
83%
8j
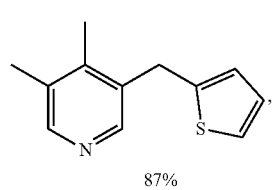
87%
8k
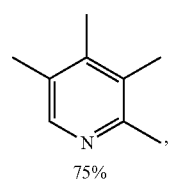
75%
8l
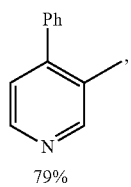
79%
8m
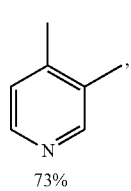
73%
8n
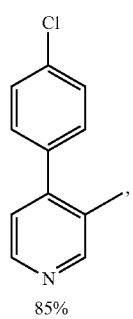
85%
-continued
8o
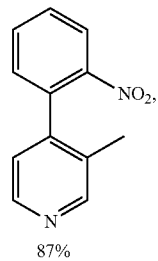
87%
8p
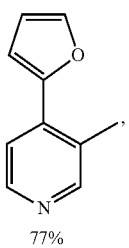
77%
8q
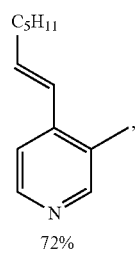
72%
8r
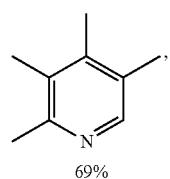
69%
8s
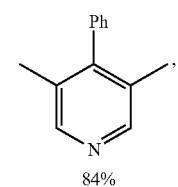
84%
8t
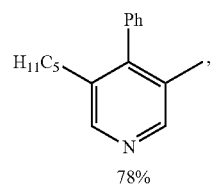
78%
8u
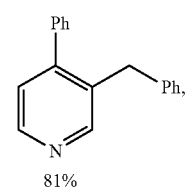
81%

-continued

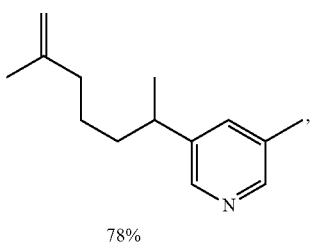
8v
78%

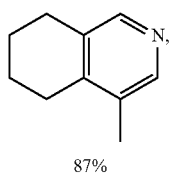
8w
87%

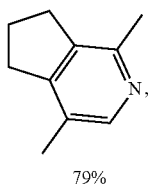
8x
79%

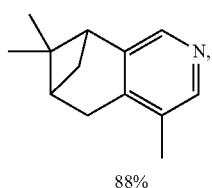
8y
88%

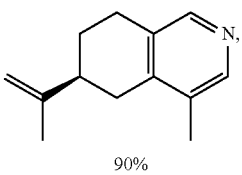
8z
90%

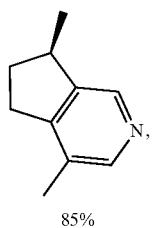
8aa
85%

To a stirred solution of α, β-unsaturated carbonyl compounds 1a-s (0.6 mmol) and propargylic amine/propargylic amine hydrochloride (0.9 mmol) in DMF (3 mL) were added 4 Å molecular sieves (200 mg) and NaHCO₃ (1.2 mmol for free propargylic amines and 1.8 mmol for propargylic amine hydrochlorides) at room temperature under an argon atmosphere. The reaction mixture was stirred for 3 h at room temperature, followed by 12 h at 80° C. The mixture was filtered through Celite, washed with Et₂O (10 mL) and water (10 mL) was added to the filtrate. The two layers were separated, and the aqueous layer was extracted with Et₂O (2×10 mL). The combined organic layer was washed with ice cold water (2×15 mL), dried over magnesium sulfate and evaporated under reduced pressure. The crude product was purified by flash column chromatography on silica gel to afford the corresponding pyridines.

Glassware was dried in an oven (120° C.), heated under reduced pressure, and cooled under argon before use. Unless otherwise noted, materials obtained from commercial suppliers were used without further purification. Reactions were monitored by thin-layer chromatography on Analtech silica gel plates using UV-light and ceric sulfate or β-naphthol for visualization. Column chromatography was performed on silica gel (230-400 mesh) using n-hexane/ethyl acetate, diethyl ether/hexanes as eluents. Evaporation of solvents was conducted under reduced pressure at 50° C. FTIR spectra were recorded neat on a Perkin-Elmer Spectrum 65. NMR spectra were recorded on a Bruker Avance III 400 NMR spectrometer at 400 MHz ($^1$H) and 100 MHz ($^{13}$C), respectively. Deuterated chloroform was used as the solvent unless otherwise noted, and spectra were calibrated against the residual solvent peak (7.24 ppm for $^1$H and 77.0 ppm for $^{13}$C). Chemical shifts (δ) and coupling constants (J) are given in ppm (parts per million) and Hz (Hertz), respectively. The following abbreviations were used to explain multiplicities: s=singlet, d=doublet, t=triplet, m=multiplet, bs=broad singlet. High Resolution mass spectra were obtained on a VG 70-70H or LC/MSD trapSL spectrometer operating at 70 eV using a direct inlet system.

Structures of Aldehyde Starting Materials (1a-s):

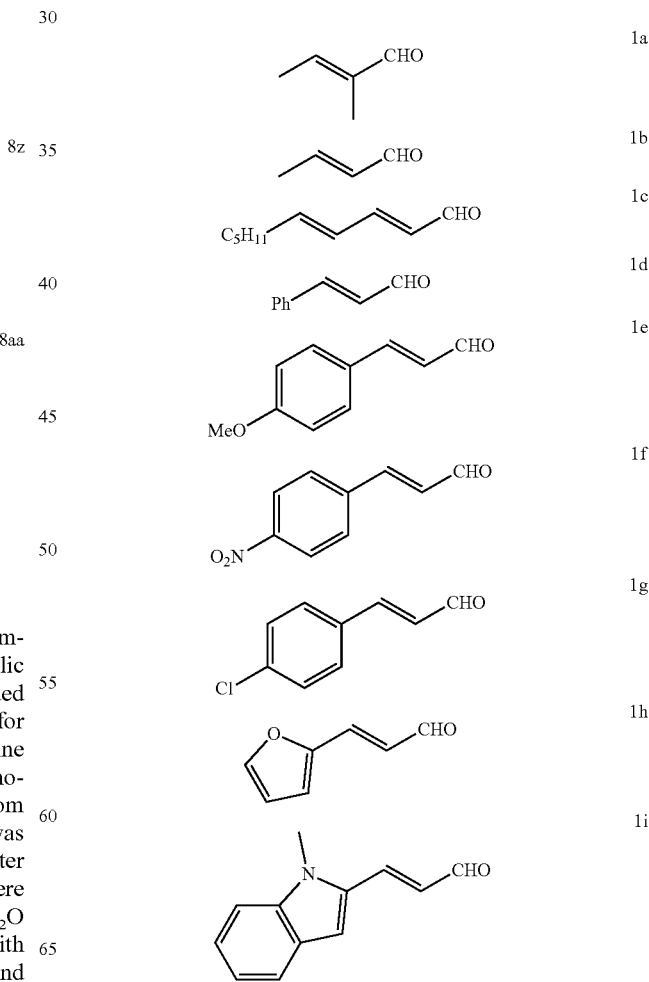

-continued
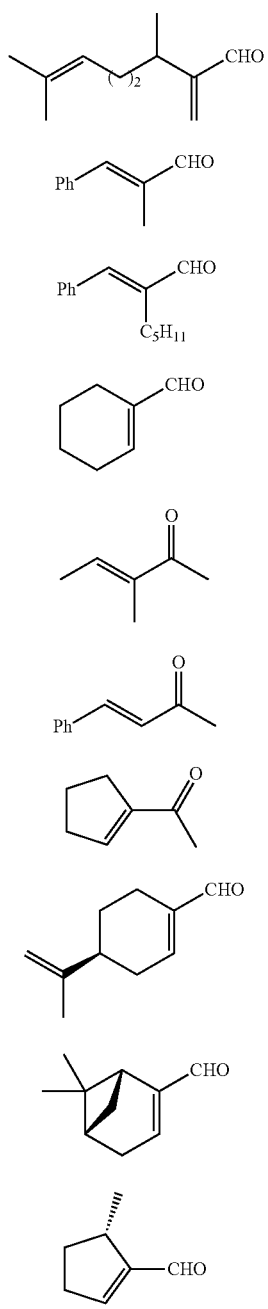
Structures of Propargylic Amines (2a-j):
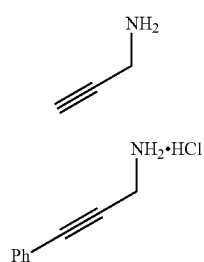
-continued
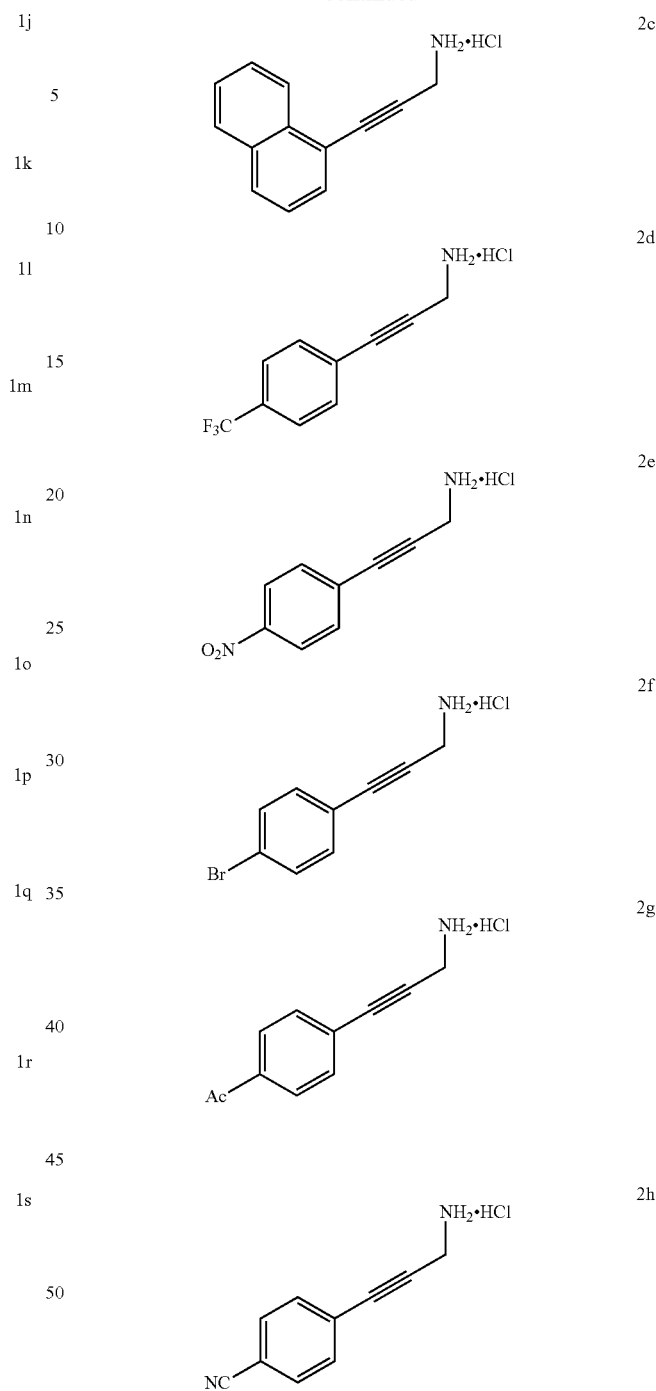

-continued

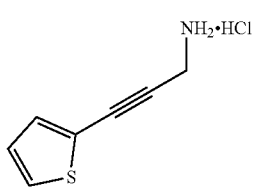

Commercially available aldehydes (1a-h and 1 k-r) and propargylic amines (2a and 2b) were used without further purification. All remaining starting aldehydes (1i and 1j, 1s) and propargylic amines (2e, 2h, 2f, and 2j) were synthesized according to literature procedures.

General Procedure for the Synthesis of Propargylic Amine Hydrochloride Salts 2c-j:

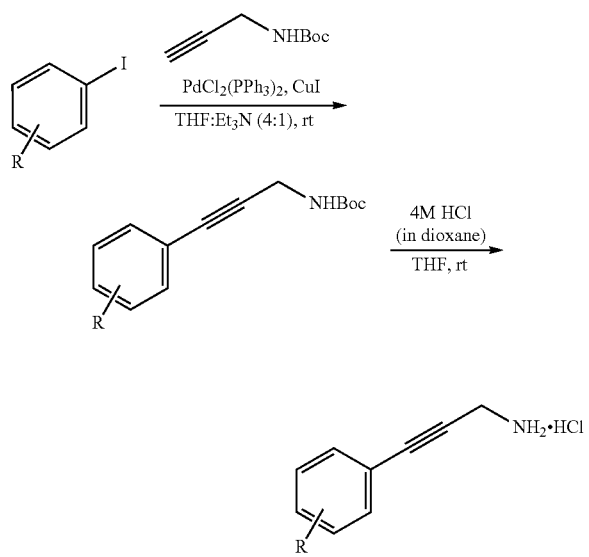

To a degassed solution of aryl iodide (5.5 mmol) and tert-butyl prop-2-yn-1-yl carbamate (0.77 g, 5.0 mmol) in THF/Et$_3$N (0.45 M, 4:1) under argon, were added CuI (38.1 mg, 0.20 mmol) and PdCl$_2$(PPh$_3$)$_2$ (70.2 mg, 0.10 mmol) at room temperature. The mixture was stirred overnight, and an aqueous solution of saturated NH$_4$Cl was added, and the mixture was extracted with Et$_2$O (3×30 mL). The combined organic layer was washed with brine (50 mL) and dried over anhydrous magnesium sulfate, filtered, and concentrated under reduced pressure. The residue was purified by flash column chromatography on silica gel (gradient, 0→20% EtOAc/hexanes) to give the corresponding propargylic amine derivatives in high yield (81-91%).

To a solution of the coupling product (4.0 mmol) in THF (4 mL) was added 4.0 M HCl in 1,4-dioxane solution (4.0 mL, 16 mmol) at room temperature, and the reaction mixture was stirred overnight. The solution was diluted with Et$_2$O upon completion. The organic layer was removed by decantation, and the precipitate was washed with Et$_2$O (3×15 mL). The solid compound was dried under vacuum to give the corresponding propargylic amine hydrochloride salts 2c-j.

3-(Naphthalen-1-yl)prop-2-yn-1-amine hydrochloride (2c)

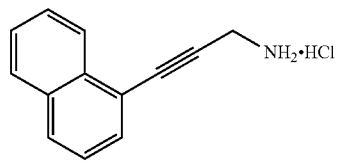

$^1$H NMR (400 MHz, DMSO-d$_6$): δ 8.79 (s, 3H), 8.40 (dd, J=8.1, 0.9 Hz, 1H), 8.02 (t, J=7.4 Hz, 2H), 7.74 (dd, J=7.1, 1.0 Hz, 1H), 7.70-7.59 (m, 2H), 7.58-7.51 (m, 1H), 4.14 (s, 2H); $^{13}$C{$^1$H}NMR (100 MHz, DMSO-d$_6$): δ 133.2, 133.1, 131.1, 130.0, 129.0, 127.7, 127.3, 126.2, 126.0, 119.3, 88.1, 83.9, 29.6.

3-(4-(Trifluoromethyl)phenyl)prop-2-yn-1-amine Hydrochloride (2d)

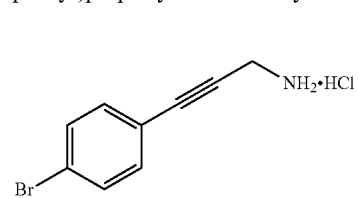

$^1$H NMR (400 MHz, DMSO-d$_6$): δ8.72 (s, 3H), 7.81 (d, J=8.2 Hz, 2H), 7.70 (d, J=8.0 Hz, 2H), 4.02 (s, 2H); $^{13}$C{$^1$H}NMR (100 MHz, DMSO-d$_6$): δ132.3, 127.7 (q, J=373.4 Hz), 125.8 (q, J=3.7 Hz), 125.4, 122.5, 85.7, 84.1, 28.8.

3-(4-Nitrophenyl)prop-2-yn-1-amine Hydrochloride (2e)

$^1$H NMR (400 MHz, DMSO-d$_6$): δ 8.67 (s, 3H), 7.68-7.57 (m, 2H), 7.45-7.35 (m, 2H), 3.95 (s, 2H); $^{13}$C{$^1$H}NMR (100 MHz, DMSO-d$_6$): δ 147.3, 132.8, 128.0, 124.1, 88.0, 83.8, 28.9.

3-(4-Bromophenyl)prop-2-yn-1-amine Hydrochloride (2f)

$^1$H NMR (400 MHz, DMSO-d$_6$): δ 8.73 (bs, 3H), 8.35-8.18 (m, 2H), 7.80-7.66 (m, 2H), 4.05 (s, 2H); $^{13}$C{$^1$H}NMR (100 MHz, DMSO-d$_6$): δ 133.4, 132.0, 122.7, 120.5, 84.5, 84.2, 28.8.

1-(4-(3-Aminoprop-1-yn-1-yl)phenyl)ethanone Hydrochloride (2g)

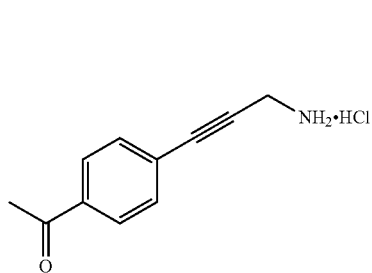

¹H NMR (400 MHz, DMSO-d₆): δ 8.68 (bs, 3H), 8.03-7.94 (m 2H), 7.64-7.58 (m, 2H), 4.03 (s, 2H), 2.60 (s, 3H); ¹³C{¹H}NMR (100 MHz, DMSO-d₆): δ 197.3, 136.7, 131.7, 128.6, 125.8, 85.9, 84.8, 28.9, 26.8.

4-(3-Aminoprop-1-yn-1-yl)benzonitrile Hydrochloride (2h)

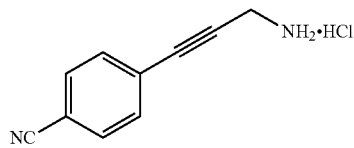

¹H NMR (400 MHz, DMSO-d₆): δ 8.67 (bs, 3H), 7.92 (d, J=8.6 Hz, 2H), 7.65 (d, J=8.6 Hz, 2H), 4.03 (s, 2H); ¹³C{¹H}NMR (100 MHz, DMSO-d₆): δ 132.8, 132.3, 126.1, 118.3, 111.6, 87.1, 84.1, 28.9.

3-(3-Nitrophenyl)prop-2-yn-1-amine Hydrochloride (2i)

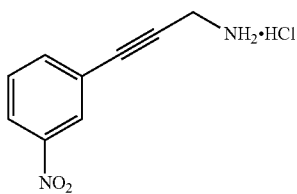

¹H NMR (400 MHz, DMSO-d₆): δ 8.77 (s, 3H), 8.27 (m, 1H), 8.23-8.18 (m, 1H), 7.93-7.87 (m, 1H), 7.76-7.67 (m, 1H), 4.01 (s, 2H); ¹³C{¹H}NMR (100 MHz, DMSO-d₆): δ 147.8, 137.5, 130.7 125.9, 124.0, 122.8, 85.4, 83.3, 28.7.

3-(Thiophen-2-yl)prop-2-yn-1-amine Hydrochloride (2j)

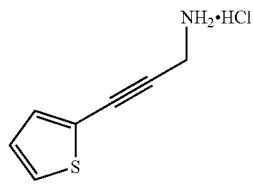

¹H NMR (400 MHz, DMSO-d₆): δ 8.62 (s, 3H), 7.68 (dd, J=5.1, 1.1 Hz, 1H), 7.37 (dd, J=3.6, 0.9 Hz, 1H), 7.11 (dd, J=5.1, 3.7 Hz, 1H), 4.00 (s, 2H); ¹³C{¹H}NMR (100 MHz, DMSO-d₆): δ 133.2, 129.2, 127.5, 120.5, 86.5, 78.7, 28.8.

3,4,5-Collidine (3a): (CAS NO: 20579-43-5)

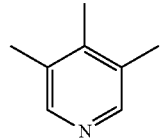

Tiglic aldehyde (1a, 50 mg, 0.60 mmol), propargylamine (2a, 49.5 mg, 0.90 mmol) and NaHCO₃ (101 mg, 1.20 mmol) in DMF (3 mL) were stirred for 3 h at room temperature followed by 12 h at 80° C. After column chromatography (Et₂O/hexanes 5:95 to 20:80), 60 mg (83%) of a pale, yellow liquid was obtained. R_f=0.3 (Et₂O/hexanes 30:70); ¹H NMR (400 MHz, CDCl₃): δ 8.18 (s, 2H), 2.24 (s, 6H), 2.18 (s, 3H); ¹³C{¹H}NMR (100 MHz, CDCl₃): δ 147.9, 144.2, 131.4, 16.8, 14.9.

3,4-Lutidine (3b): (CAS NO: 583-58-4)

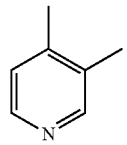

Crotonaldehyde (1b, 42 mg, 0.60 mmol), propargylamine (2a, 49.5 mg, 0.90 mmol) and NaHCO₃ (101 mg, 1.20 mmol) in DMF (3 mL) were stirred for 3 h at room temperature followed by 12 h at 80° C. After column chromatography (Et₂O/hexanes 5:95 to 30:70), 46 mg (72%) of a pale yellow liquid was obtained. R_f=0.4 (Et₂O/hexanes 30:70); ¹H NMR (400 MHz, CDCl₃): δ 8.32 (s, 1H), 8.30 (d, J=4.9 Hz, 1H), 7.04 (d, J=4.9 Hz, 1H), 2.26 (s, 3H), 2.24 (s, 3H); ¹³C{¹H}NMR (100 MHz, CDCl₃): δ 150.0, 147.3, 145.5, 132.1, 124.5, 19.0, 16.3.

(E)-4-(Hept-1-en-1-yl)-3-methylpyridine (3c)

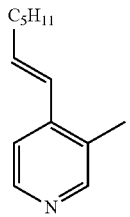

(2E,4E)-Deca-2,4-dienal (1c, 91 mg, 0.60 mmol), propargylamine (2a, 49.5 mg, 0.90 mmol) and NaHCO₃ (101 mg, 1.20 mmol) in DMF (3 mL) were stirred for 3 h at room temperature followed by 12 h at 80° C. After column chromatography (EtOAc/hexanes 5:95 to 20:80), 88 mg (78%) of a pale, yellow liquid was obtained. R_f=0.4 (EtOAc/hexanes 30:70); ¹H NMR (400 MHz, CDCl₃): δ 8.35-8.33 (m, 2H), 7.26 (d, J=5.2 Hz, 1H), 6.49 (d, J=15.7 Hz, 1H), 6.34 (dt, J=15.7, 6.8 Hz, 1H), 2.29 (s, 3H), 2.25 (ddd, J=10.4, 5.5, 1.9 Hz, 2H), 1.54-1.44 (m, 2H), 1.37-1.29 (m, 4H), 0.91 (t, J=7.0 Hz, 3H); ¹³C{¹H}NMR (100 MHz, CDCl₃): δ 151.0, 147.4, 144.1, 136.8, 129.6, 125.2, 119.1, 33.3, 31.3, 28.7, 22.4, 16.4, 14.0; FTIR (neat): 2929, 2856, 1710, 1602, 1384, 1278, 1037, 856, 699 cm⁻¹; MS (ESI): m/z 190 (M+H)⁺; HRMS (ESI): m/z calcd for C₁₃H₂₀N (M+H)⁺: 190.1590, found: 190.1595.

3-Methyl-4-phenylpyridine (3d)

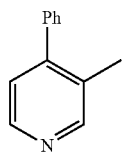

trans-Cinnamaldehyde (1d, 80 mg, 0.60 mmol), propargylamine (2a, 49.5 mg, 0.90 mmol) and NaHCO$_3$ (101 mg, 1.20 mmol) in DMF (3 mL) were stirred for 3 h at room temperature followed by 12 h at 80° C. After column chromatography (Et$_2$O/hexanes 5:95 to 20:80), 90 mg (89%) of a pale, yellow liquid was obtained. R$_f$=0.4 (Et$_2$O/hexanes 30:70); $^1$H NMR (400 MHz, CDCl$_3$): δ 8.51 (s, 1H), 8.47 (d, J=5.0 Hz, 1H), 7.50-7.37 (m, 3H), 7.36-7.30 (m, 2H), 7.15 (d, J=5.0 Hz, 1H), 2.28 (s, 3H); $^{13}$C{$^1$H}NMR (100 MHz, CDCl$_3$): δ 151.3, 149.1, 147.3, 139.0, 130.6, 128.5, 128.4, 127.9, 124.0, 17.2.

4-(4-Methoxyphenyl)-3-methylpyridine (3e)

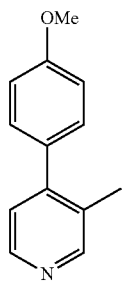

trans-p-Methoxycinnamaldehyde (1e, 97 mg, 0.60 mmol), propargylamine (2a, 49.5 mg, 0.90 mmol) and NaHCO$_3$ (101 mg, 1.20 mmol) in DMF (3 mL) were stirred for 3 h at room temperature followed by 12 h at 80° C. After column chromatography (EtOAc/hexanes 5:95 to 20:80), 107 mg (90%) of a pale, yellow solid was obtained. R$_f$=0.5 (EtOAc/hexanes 30:70), mp=112-114° C.; $^1$H NMR (400 MHz, CDCl$_3$): δ 8.48 (s, 1H), 8.44 (d, J=4.8 Hz, 1H), 7.29-7.24 (m, 2H), 7.13 (d, J=5.0 Hz, 1H), 7.01-6.95 (m, 2H), 3.85 (s, 3H), 2.29 (s, 3H); $^{13}$C{$^1$H}NMR (100 MHz, CDCl$_3$): δ 159.3, 151.2, 148.6, 147.3, 131.2, 130.5, 129.7, 123.9, 113.7, 55.2, 17.3.

3-Methyl-4-(4-nitrophenyl)pyridine (3f)

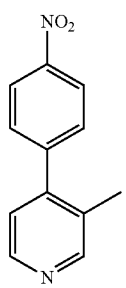 [SMILES: Cc1cnccc1-c1ccc([N+](=O)[O-])cc1]

4-Nitrocinnamaldehyde (1f, 106 mg, 0.60 mmol), propargylamine (2a, 49.5 mg, 0.90 mmol) and NaHCO$_3$ (101 mg, 1.20 mmol) in DMF (3 mL) were stirred for 3 h at room temperature followed by 12 h at 80° C. After column chromatography (EtOAc/hexanes 5:95 to 25:75), 106 mg (83%) of a pale, yellow solid was obtained. R$_f$=0.4 (EtOAc/hexanes 30:70), mp=139-141° C.; $^1$H NMR (400 MHz, CDCl$_3$): δ 8.58 (s, 1H), 8.54 (d, J=5.0 Hz, 1H), 8.36-8.31 (m, 2H), 7.55-7.50 (m, 2H), 7.16 (d, J=5.0 Hz, 1H), 2.29 (s, 3H); $^{13}$C{$^1$H}NMR (100 MHz, CDCl$_3$): δ 151.5, 147.6, 146.9, 145.5, 130.2, 129.6, 123.8, 123.8, 123.1, 17.1; FTIR (neat): 2928, 1590, 1512, 1344, 1106, 994, 855, 735, 697 cm$^{-1}$; MS (ESI): m/z 215 (M+H)$^+$; HRMS (ESI): m/z calcd for C$_{12}$H$_{11}$N$_2$O$_2$ (M+H)$^+$: 215.0815, found: 215.0818.

4-(4-Chlorophenyl)-3-methylpyridine (3g)

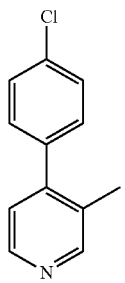

4-Chlorocinnamaldehyde (1 g, 100 mg, 0.60 mmol), propargylamine (2a, 49.5 mg, 0.90 mmol) and NaHCO$_3$ (101 mg, 1.20 mmol) in DMF (3 mL) were stirred for 3 h at room temperature followed by 12 h at 80° C. After column chromatography (EtOAc/hexanes 5:95 to 20:80), 111 mg (93%) of a pale, yellow liquid was obtained. R$_f$=0.4 (EtOAc/hexanes 30:70); $^1$H NMR (400 MHz, CDCl$_3$): δ 8.51 (s, 1H), 8.47 (d, J=5.0 Hz, 1H), 7.47-7.40 (m, 2H), 7.30-7.23 (m, 2H), 7.12 (d, J=5.0 Hz, 1H), 2.27 (s, 3H); $^{13}$C{$^1$H}NMR (100 MHz, CDCl$_3$): δ 151.3, 147.8, 147.4, 137.3, 134.0, 130.4, 129.8, 128.6, 123.7, 17.1.

4-(Furan-2-yl)-3-methylpyridine (3h)

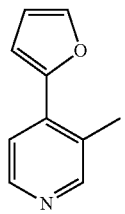

(E)-3-(Furan-2-yl)acrylaldehyde (1h, 73 mg, 0.60 mmol), propargylamine (2a, 49.5 mg, 0.90 mmol) and NaHCO$_3$ (101 mg, 1.20 mmol) in DMF (3 mL) were stirred for 3 h at room temperature followed by 12 h at 80° C. After column chromatography (EtOAc/hexanes 5:95 to 25:75), 83 mg (87%) of a pale, yellow semi solid was obtained. R$_f$=0.4 (EtOAc/hexanes 30:70); $^1$H NMR (400 MHz, CDCl$_3$): δ 8.47 (d, J=3.9 Hz, 2H), 7.62 (d, J=5.2 Hz, 1H), 7.59 (dd, J=1.8, 0.6 Hz, 1H), 6.80 (dd, J=3.5, 0.5 Hz, 1H), 6.57 (dd, J=3.5, 1.8 Hz, 1H), 2.50 (s, 3H); $^{13}$C{$^1$H}NMR (100 MHz, CDCl$_3$): 5151.9, 150.9, 147.5, 143.3, 136.6, 128.1, 119.4, 112.0, 111.9, 19.0; FTIR (neat): 2921, 1619, 1445, 1330, 1268, 1159, 1024, 980, 882, 791, 741 cm$^{-1}$; MS (ESI): m/z 160 (M+H)$^+$; HRMS (ESI): m/z calcd for C$_{10}$H$_{10}$NO (M+H)$^+$: 160.0757, found: 160.0756.

1-Methyl-2-(3-methylpyridin-4-yl)-1H-indole (3i)

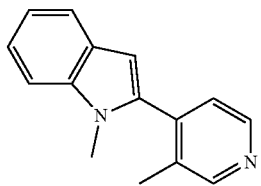 [SMILES: Cc1cnccc1-c1cc2ccccc2n1C]

(E)-3-(1-Methyl-1H-indol-2-yl)acrylaldehyde (1i, 111 mg, 0.60 mmol), propargylamine (2a, 49.5 mg, 0.90 mmol) and NaHCO$_3$ (101 mg, 1.20 mmol) in DMF (3 mL) were stirred for 3 h at room temperature followed by 12 h at 80° C. After column chromatography (EtOAc/hexanes 5:95 to 30:70), 114 mg (86%) of a yellow semisolid was obtained. R$_f$=0.4 (EtOAc/hexanes 30:70); $^1$H NMR (400 MHz, CDCl$_3$): δ 8.59 (s, J=0.6 Hz, 1H), 8.52 (d, J=4.9 Hz, 1H), 7.69-7.62 (m, 1H), 7.38 (dd, J=8.2, 0.8 Hz, 1H), 7.29 (ddd, J=8.2, 7.0, 1.2 Hz, 1H), 7.21 (d, J=4.9 Hz, 1H), 7.17 (ddd, J=7.0, 5.5, 1.0 Hz, 1H), 6.51 (d, J=0.8 Hz, 1H), 3.55 (s, 3H), 2.25 (s, 3H); $^{13}$C{$^1$H}NMR (100 MHz, CDCl$_3$): δ 151.3, 147.1, 140.2, 137.7, 137.2, 132.8, 127.7, 125.0, 122.1, 120.7, 120.0, 109.6, 102.6, 30.6, 17.0; FTIR (neat): 2976, 1576, 1495, 1400, 1254, 1145, 892, 757, 698 cm$^{-1}$; MS (ESI): m/z 223 (M+H)$^+$; HRMS (ESI): m/z calcd for C$_{15}$H$_{15}$N$_2$ (M+H)$^+$: 223.1230, found: 223.1233.

3-Methyl-5-(6-methylhept-5-en-2-yl)pyridine (3j)

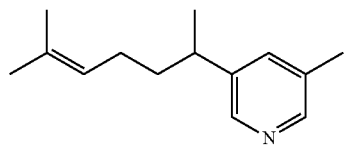

3,7-dimethyl-2-methyleneoct-6-enal (1j, 100 mg, 0.60 mmol), propargylamine (2a, 49.5 mg, 0.90 mmol) and NaHCO$_3$ (101 mg, 1.20 mmol) in DMF (3 mL) were stirred for 12 h at room temperature followed by 12 h at 80° C. After column chromatography (EtOAc/hexanes 5:95 to 20:80), 98 mg (81%) of a pale, yellow liquid was obtained. R$_f$=0.3 (EtOAc/hexanes 30:70); $^1$H NMR (400 MHz, CDCl$_3$): δ 8.26 (s, 1H), 8.23 (s, 1H), 7.29 (s, 1H), 5.07 (m, 1H), 2.69 (h, J=7.1 Hz, 1H), 2.32 (s, 3H), 1.95-1.83 (m, 2H), 1.67 (s, 3H), 1.61 (q, J=7.6 Hz, 2H), 1.51 (s, 3H), 1.24 (d, J=7.0 Hz, 3H); $^{13}$C{$^1$H}NMR (100 MHz, CDCl$_3$): δ 147.8, 146.3, 142.0, 134.8, 132.7, 131.8, 124.0, 38.0, 36.7, 26.0, 25.7, 22.1, 18.4, 17.6; FTIR (neat): 2961, 1682, 1577, 1438, 1376, 1147, 1028, 983, 873, 719 cm$^{-1}$; MS (ESI): m/z 204 (M+H)$^+$; HRMS (ESI): m/z calcd for C$_{14}$H$_{22}$N (M+H)$^+$: 204.1747, found: 204.1741.

2,6-Dimethyl-1,1'-biphenyl (3k)

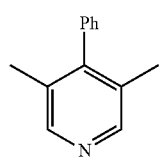

α-Methyl-trans-cinnamaldehyde (1k, 87 mg, 0.60 mmol), propargylamine (2a, 49.5 mg, 0.90 mmol) and NaHCO$_3$ (101 mg, 1.20 mmol) in DMF (3 mL) were stirred for 3 h at room temperature followed by 12 h at 80° C. After column chromatography (EtOAc/hexanes 5:95 to 20:80), 90 mg (83%) of a white solid was obtained. R$_f$=0.4 (EtOAc/hexanes 30:70), mp=106-108° C.; $^1$H NMR (400 MHz, CDCl$_3$): δ 8.35 (s, 2H), 7.50-7.43 (m, 2H), 7.42-7.35 (m, 1H), 7.15-7.08 (m, 2H), 2.03 (s, 6H); $^{13}$C{$^1$H}NMR (100 MHz, CDCl$_3$): δ 149.3, 148.3, 138.0, 130.8, 128.7, 127.9, 127.5, 17.3.

3-Methyl-5-pentyl-4-phenylpyridine (3l)

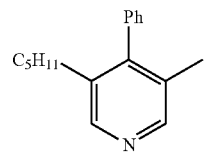

(E)-alpha-Amyl cinnamaldehyde (Jasmonal A, 1l, 121 mg, 0.60 mmol), propargylamine (2a, 49.5 mg, 0.90 mmol) and NaHCO$_3$ (101 mg, 1.20 mmol) in DMF (3 mL) were stirred for 3 h at room temperature followed by 12 h at 80° C. After column chromatography (EtOAc/hexanes 5:95 to 25:75), 129 mg (91%) of a colorless liquid was obtained. R$_f$=0.3 (EtOAc/hexanes 30:70); $^1$H NMR (400 MHz, CDCl$_3$): δ 8.36 (s, 1H), 8.33 (s, 1H), 7.48-7.35 (m, 3H), 7.16-7.08 (m, 2H), 2.40-2.30 (m, 2H), 2.00 (s, 3H), 1.42-1.32 (m, 2H), 1.20-1.08 (m, 4H), 0.78 (t, J=6.9 Hz, 3H); $^{13}$C{$^1$H}NMR (100 MHz, CDCl$_3$): δ 148.9, 148.1, 148.0, 137.7, 135.4, 130.9, 128.4, 128.2, 127.4, 31.4, 30.5, 30.5, 22.1, 17.4, 13.8; FTIR (neat): 2955, 1582, 1464, 1380, 1158, 1041, 885, 758, 702 cm$^{-1}$; MS (ESI): m/z 240 (M+H)$^+$; HRMS (ESI): m/z calcd for C$_{17}$H$_{22}$N (M+H)$^+$: 240.1747, found: 240.1749.

4-Methyl-5,6,7,8-tetrahydroisoquinoline (3m)

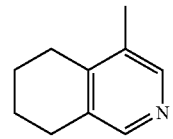

1-Cyclohexene-1-carboxaldehyde (1m, 66 mg, 0.60 mmol), propargylamine (2a, 49.5 mg, 0.90 mmol) and NaHCO$_3$ (101 mg, 1.20 mmol) in DMF (3 mL) were stirred for 3 h at room temperature followed by 12 h at 80° C. After column chromatography (Et$_2$O/hexanes 5:95 to 20:80), 76 mg (87%) of a pale, yellow liquid was obtained. R$_f$=0.5 (Et$_2$O/hexanes 30:70); $^1$H NMR (400 MHz, CDCl$_3$): δ 8.15 (s, 1H), 8.14 (s, 1H), 2.73 (t, J=6.1 Hz, 2H), 2.60 (t, J=6.3 Hz, 2H), 2.17 (s, 3H), 1.89-1.74 (m, 4H); $^{13}$C{$^1$H}NMR (100 MHz, CDCl$_3$): δ 148.1, 147.0, 144.5, 132.2, 131.4, 26.6, 26.0, 22.5, 22.3, 15.9; FTIR (neat): 2929, 1680, 1588, 1449, 1421, 1192, 1141, 909, 800, 718 cm$^{-1}$; MS (ESI): m/z 148 (M+H)$^+$; HRMS (ESI): m/z calcd for C$_{10}$H$_{14}$N (M+H)$^+$: 148.1121, found: 148.1125.

3-Benzyl-4,5-dimethylpyridine (3n)

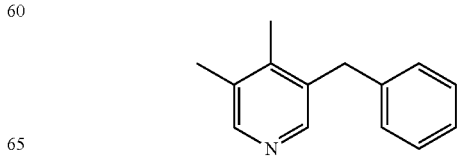

Tiglic aldehyde (1a, 50 mg, 0.60 mmol), 3-phenylprop-2-yn-1-amine hydrochloride (2b, 150 mg, 0.90 mmol) and NaHCO₃ (151 mg, 1.80 mmol) in DMF (3 mL) were stirred for 3 h at room temperature followed by 12 h at 80° C. After column chromatography (EtOAc/hexanes 5:95 to 20:80), 93 mg (79%) of a pale, yellow semi solid was obtained. $R_f$=0.4 (EtOAc/hexanes 30:70); ¹H NMR (400 MHz, CDCl₃): δ 8.25 (s, 1H), 8.24 (s, 1H), 7.30-7.23 (m, 2H), 7.22-7.15 (m, 1H), 7.09 (ddd, J=8.1, 2.4, 1.8 Hz, 2H), 3.99 (s, 2H), 2.24 (s, 3H), 2.11 (s, 3H); ¹³C{¹H}NMR (100 MHz, CDCl₃): δ 148.7, 148.7, 144.6, 139.5, 133.8, 132.2, 128.5, 128.4, 126.2, 36.9, 16.9, 15.1; FTIR (neat): 2925, 1669, 1598, 1491, 1385, 1197, 1125, 797, 757, 695 cm⁻¹; MS (ESI): m/z 198 (M+H)⁺; HRMS (ESI): m/z calcd for $C_{14}H_{16}N$ (M+H)⁺: 198.1277, found: 198.1280.

3,4-Dimethyl-5-(naphthalen-1-ylmethyl)pyridine (3o)

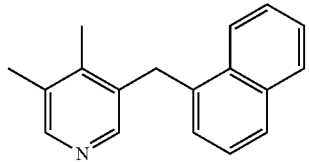 [SMILES: Cc1cncc(Cc2cccc3ccccc23)c1C]

Tiglic aldehyde (1a, 50 mg, 0.60 mmol), 3-(naphthalen-1-yl)prop-2-yn-1-amine hydrochloride (2c, 195 mg, 0.90 mmol) and NaHCO₃ (151 mg, 1.80 mmol) in DMF (3 mL) were stirred for 3 h at room temperature followed by 12 h at 80° C. After column chromatography (EtOAc/hexanes 5:95 to 20:80), 127 mg (86%) of a pale, yellow solid was obtained. $R_f$=0.5 (EtOAc/hexanes 30:70); mp=121-123° C.; ¹H NMR (400 MHz, CDCl₃): δ 8.29 (s, 1H), 8.11 (s, 1H), 8.04 (d, J=7.9 Hz, 1H), 7.91-7.85 (m, 1H), 7.74 (d, J=8.2 Hz, 1H), 7.57-7.47 (m, 2H), 7.33 (t, J=7.7 Hz, 1H), 6.89 (d, J=7.0 Hz, 1H), 4.41 (s, 2H), 2.29 (s, 3H), 2.14 (s, 3H); ¹³C{¹H}NMR (100 MHz, CDCl₃): δ 148.9, 148.8, 144.7, 135.1, 133.7, 133.2, 132.0, 131.9, 128.8, 127.1, 126.2, 125.8, 125.7, 125.5, 123.3, 33.6, 17.0, 15.0; FTIR (neat): 2917, 1597, 1440, 1399, 1186, 1074, 887, 793, 774, 757 cm⁻¹; MS (ESI): m/z 248 (M+H)⁺; HRMS (ESI): m/z calcd for $C_{18}H_{18}N$ (M+H)⁺: 248.1434, found: 248.1437.

3,4-Dimethyl-5-(4-(trifluoromethyl)benzyl)pyridine (3p)

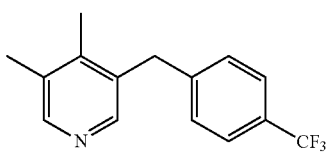 [SMILES: Cc1cncc(Cc2ccc(C(F)(F)F)cc2)c1C]

Tiglic aldehyde (1a, 50 mg, 0.60 mmol), 3-(4-(trifluoromethyl)phenyl)prop-2-yn-1-amine hydrochloride (2d, 211 mg, 0.90 mmol) and NaHCO₃ (151 mg, 1.80 mmol) in DMF (3 mL) were stirred for 3 h at room temperature 12 h at 80° C. After column chromatography (EtOAc/hexanes 5:95 to 20:80), 145 mg (93%) of a pale, yellow solid was obtained. $R_f$=0.5 (EtOAc/hexanes 30:70); mp=127-129° C.; ¹H NMR (400 MHz, CDCl₃): δ 8.29 (s, 1H), 8.25 (s, 1H), 7.52 (d, J=8.1 Hz, 2H), 7.21 (d, J=8.0 Hz, 2H), 4.05 (s, 2H), 2.25 (s, 3H), 2.09 (s, 3H); ¹³C{¹H}NMR (100 MHz, CDCl₃): δ 149.1, 148.7, 144.5, 143.7, 132.9, 132.4, 128.7, 128.6 (q, J=32.4 Hz), 125.4 (q, J=3.9 Hz), 124.1 (q, J=271.9 Hz), 36.7, 16.9, 15.1; FTIR (neat): 2925, 1618, 1416, 1321, 1160, 1107, 1065, 1017, 815, 726 cm⁻¹; MS (ESI): m/z 266 (M+H)⁺; HRMS (ESI): m/z calcd for $C_{15}H_{15}F_3N$ (M+H)⁺: 266.1151, found: 266.1154.

3,4-Dimethyl-5-(4-nitrobenzyl)pyridine (3q)

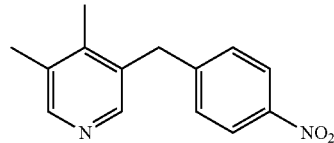 [SMILES: Cc1cncc(Cc2ccc([N+](=O)[O-])cc2)c1C]

Tiglic aldehyde (1a, 50 mg, 0.60 mmol), 3-(4-nitrophenyl)prop-2-yn-1-amine hydrochloride (2e, 190.8 mg, 0.90 mmol) and NaHCO₃ (151 mg, 1.80 mmol) in DMF (3 mL) were stirred for 3 h at room temperature followed by 12 h at 80° C. After column chromatography (EtOAc/hexanes 5:95 to 20:80), 126 mg (87%) of a pale, yellow solid was obtained. $R_f$=0.6 (EtOAc/hexanes 30:70), mp=163-165° C.; ¹H NMR (400 MHz, CDCl₃): δ 8.31 (s, 1H), 8.26 (s, 1H), 8.14 (d, J=8.8 Hz, 2H), 7.26 (d, J=8.9 Hz, 2H), 4.11 (s, 2H), 2.26 (s, 3H), 2.09 (s, 3H); ¹³C{¹H}NMR (100 MHz, CDCl₃): δ 149.5, 148.7, 147.3, 146.6, 144.5, 132.6, 132.3, 129.1, 123.8, 36.8, 16.9, 15.2; FTIR (neat): 2923, 1594, 1440, 1340, 1105, 930, 834, 733, 698 cm⁻¹; MS (ESI): m/z 243 (M+H)⁺; HRMS (ESI): m/z calcd for $C_{14}H_{15}N_2O_2$ (M+H)⁺: 243.1128, found: 243.1132.

3-(4-Bromobenzyl)-4,5-dimethylpyridine (3r)

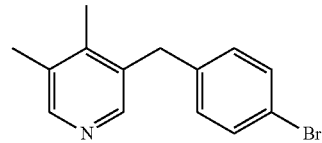 [SMILES: Cc1cncc(Cc2ccc(Br)cc2)c1C]

Tiglic aldehyde (1a, 50 mg, 0.60 mmol), 3-(4-bromophenyl)prop-2-yn-1-amine hydrochloride (2f, 219 mg, 0.90 mmol) and NaHCO₃ (151 mg, 1.80 mmol) in DMF (3 mL) were stirred for 3 h at room temperature followed by 12 h at 80° C. After column chromatography (EtOAc/hexanes 5:95 to 20:80), 146 mg (88%) of a pale, yellow solid was obtained. $R_f$=0.5 (EtOAc/hexanes 30:70), mp=127-129° C.; ¹H NMR (400 MHz, CDCl₃): δ 8.27 (s, 1H), 8.23 (s, 1H), 7.38 (d, J=8.4 Hz, 2H), 6.96 (d, J=8.5 Hz, 2H), 3.94 (s, 2H), 2.24 (s, 3H), 2.08 (s, 3H); ¹³C{¹H}NMR (100 MHz, CDCl₃): δ 149.0, 148.7, 144.4, 138.5, 133.2, 132.3, 131.5, 130.1, 120.0, 36.3, 16.9, 15.1; FTIR (neat): 2920, 1585, 1485, 1414, 1072, 1012, 897, 793, 746 cm⁻¹; MS (ESI): m/z 276 (M+H)⁺; HRMS (ESI): m/z calcd for $C_{14}H_{15}BrN$ (M+H)⁺: 276.0382, found: 276.0385.

1-(4-((4,5-Dimethylpyridin-3-yl)methyl)phenyl)ethanone (3s)

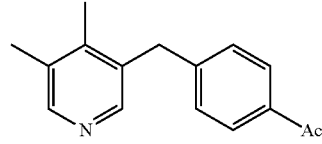 [SMILES: CC(=O)c1ccc(Cc2cncc(C)c2C)cc1]

Tiglic aldehyde (1a, 50 mg, 0.60 mmol), 1-(4-(3-aminoprop-1-yn-1-yl)phenyl)ethanone hydrochloride (2 g, 188 mg, 0.90 mmol) and NaHCO₃ (151 mg, 1.80 mmol) in DMF (3 mL) were stirred for 3 h at room temperature followed by 12 h at 80° C. After column chromatography (EtOAc/hexanes 5:95 to 20:80) 120 mg (84%) of a pale yellow solid was obtained. $R_f$=0.5 (EtOAc/hexanes 30:70), mp=122-124° C.; $^1$H NMR (400 MHz, CDCl$_3$): 58.28 (s, 1H), 8.26 (s, 1H), 7.87 (d, J=8.4 Hz, 2H), 7.19 (d, J=8.5 Hz, 2H), 4.05 (s, 2H), 2.57 (s, 3H), 2.25 (s, 3H), 2.09 (s, 3H); $^{13}$C{$^1$H}NMR (100 MHz, CDCl$_3$): δ 197.6, 149.1, 148.7, 145.2, 144.5, 135.3, 133.0, 132.4, 128.6, 128.5, 36.9, 26.5, 16.9, 15.1; FTIR (neat): 2919, 1677, 1606, 1412, 1356, 1269, 1018, 958, 895, 749 cm$^{-1}$; MS (ESI): m/z 240 (M+H)$^+$; HRMS (ESI): m/z calcd for C$_{16}$H$_{18}$NO (M+H)$^+$: 240.1383, found: 240.1386.

4-((4,5-Dimethylpyridin-3-yl)methyl)benzonitrile (3t)

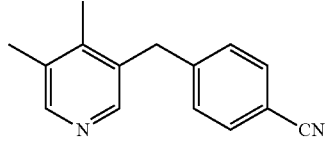 [SMILES: Cc1cncc(Cc2ccc(C#N)cc2)c1C]

Tiglic aldehyde (1a, 50 mg, 0.60 mmol), 4-(3-aminoprop-1-yn-1-yl)benzonitrile hydrochloride (2h, 172.8 mg, 0.90 mmol) and NaHCO$_3$ (151 mg, 1.80 mmol) in DMF (3 mL) were stirred for 3 h at room temperature followed by 12 h at 80° C. After column chromatography (gradient: EtOAc/hexanes 5:95 to 20:80) 120 mg (90%) of a pale, yellow solid was obtained. $R_f$=0.5 (EtOAc/hexanes 30:70), mp=145-147° C.; $^1$H NMR (400 MHz, CDCl$_3$): δ 8.30 (s, 1H), 8.24 (s, 1H), 7.57 (d, J=8.4 Hz, 2H), 7.21 (dd, J=8.0, 0.5 Hz, 2H), 4.06 (s, 2H), 2.26 (s, 3H), 2.08 (s, 3H); $^{13}$C{$^1$H}NMR (100 MHz, CDCl$_3$): 5149.3, 148.7, 145.2, 144.4, 132.5, 132.3, 132.3, 129.1, 118.7, 110.2, 36.9, 16.9, 15.1; FTIR (neat): 2945, 2224, 1584, 1500, 1412, 1172, 995, 892, 812, 755 cm$^{-1}$; MS (ESI): m/z 223 (M+H)$^+$; HRMS (ESI): m/z calcd for C$_{15}$H$_{15}$N$_2$ (M+H)$^+$ 223.1230, found: 223.1234.

3,4-Dimethyl-5-(3-nitrobenzyl)pyridine (3u)

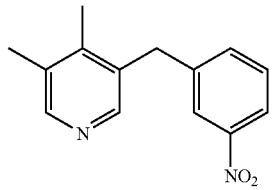 [SMILES: Cc1cncc(Cc2cccc([N+](=O)[O-])c2)c1C]

Tiglic aldehyde (1a, 50 mg, 0.60 mmol), 3-(3-nitrophenyl)prop-2-yn-1-amine hydrochloride (2i, 190.8 mg, 0.90 mmol) and NaHCO$_3$ (151 mg, 1.80 mmol) in DMF (3 mL) were stirred for 3 h at room temperature followed by 12 h at 80° C. After column chromatography (EtOAc/hexanes 5:95 to 20:80), 132 mg (91%) of a pale, yellow solid was obtained. $R_f$=0.6 (EtOAc/hexanes 30:70), mp=170-172° C.; $^1$H NMR (400 MHz, CDCl$_3$): δ 8.30 (d, J=10.9 Hz, 1H), 8.26 (s, 1H), 8.07 (d, J=6.8 Hz, 1H), 7.99 (s, 1H), 7.45 (m, 2H), 4.11 (s, 2H), 2.27 (s, 3H), 2.11 (s, 3H); $^{13}$C{$^1$H}NMR (100 MHz, CDCl$_3$): δ 149.5, 148.7, 148.4, 144.3, 141.7, 134.5, 132.5, 132.3, 129.4, 123.2, 121.5, 36.5, 16.9, 15.2; FTIR (neat): 2921, 1530, 1438, 1384, 1093, 996, 928, 804, 726, 691 cm$^{-1}$; MS (ESI): m/z 243 (M+H)$^+$; HRMS (ESI): m/z calcd for C$_{14}$H$_{15}$N$_2$O$_2$ (M+H)$^+$: 243.1128, found: 243.1129.

3,4-Dimethyl-5-(thiophen-2-ylmethyl)pyridine (3v)

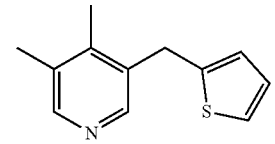

Tiglic aldehyde (1a, 50 mg, 0.60 mmol), 3-(thiophen-2-yl)prop-2-yn-1-amine hydrochloride (2j, 155.7 mg, 0.90 mmol) and NaHCO$_3$ (151 mg, 1.80 mmol) in DMF (3 mL) were stirred for 3 h at room temperature followed by 12 h at 80° C. After column chromatography (EtOAc/hexanes 5:95 to 20:80) 102 mg (84%) of a pale, yellow liquid was obtained. $R_f$=0.5 (EtOAc/hexanes 30:70); $^1$H NMR (400 MHz, CDCl$_3$): δ 8.28 (s, 1H), 8.27 (s, 1H), 7.13 (dd, J=5.1, 1.2 Hz, 1H), 6.90 (dd, J=5.1, 3.5 Hz, 1H), 6.72-6.64 (m, 1H), 4.15 (s, 2H), 2.25 (s, 3H), 2.18 (s, 3H); $^{13}$C{$^1$H}NMR (100 MHz, CDCl$_3$): δ 149.0, 148.3, 144.3, 142.8, 133.6, 132.3, 126.8, 124.9, 123.8, 31.3, 16.9, 14.9; FTIR (neat): 2919, 1586, 1437, 1286, 1230, 1108, 1017, 886, 821, 694 cm$^{-1}$; MS (ESI): m/z 204 (M+H)$^+$; HRMS (ESI): m/z calcd for C$_{12}$H$_{14}$NOS (M+H)$^+$: 204.0841, found: 204.0843.

3-Benzyl-4-phenylpyridine (3w)

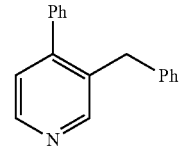

trans-Cinnamaldehyde (1d, 80 mg, 0.60 mmol), 3-phenylprop-2-yn-1-amine hydrochloride (2b, 150 mg, 0.90 mmol) and NaHCO$_3$ (151 mg, 1.80 mmol) in DMF (3 mL) were stirred for 3 h at room temperature followed by 12 h at 80° C. After column chromatography (EtOAc/hexanes 5:95 to 30:70), 117 mg (80%) of a pale, yellow semi-solid was obtained. $R_f$=0.5 (EtOAc/hexanes 30:70); $^1$H NMR (400 MHz, CDCl$_3$): δ 8.63-8.25 (m, 2H), 7.41-7.35 (m, 3H), 7.23-7.13 (m, 6H), 6.96-6.89 (m, 2H), 3.98 (s, 2H); $^{13}$C{$^1$H}NMR (100 MHz, CDCl$_3$): δ 151.6, 149.7, 147.6, 140.1, 138.7, 133.6, 128.6, 128.5, 128.4, 128.3, 128.0, 126.1, 124.5, 36.3; FTIR (neat): 3057, 1668, 1588, 1493, 1407, 1179, 838, 752, 695 cm$^{-1}$; MS (ESI): m/z 246 (M+H)$^+$; HRMS (ESI): m/z calcd for C$_{18}$H$_{16}$N (M+H)$^+$: 246.1277, found: 246.1279.

2,3,4,5-Tetramethylpyridine (3x)

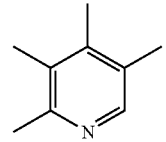

(E)-3-Methylpent-3-en-2-one (1n, 59 mg, 0.60 mmol), propargylamine (2a, 49.5 mg, 0.90 mmol) and NaHCO$_3$ (101 mg, 1.20 mmol) in DMF (3 mL) were stirred for 3 h at room temperature followed by 12 h at 80° C. After column chromatography (Et$_2$O/hexanes 5:95 to 20:80), 59 mg (73%) of a pale, yellow liquid was obtained. $R_f$=0.4 (Et$_2$O/hexanes 30:70); $^1$H NMR (400 MHz, CDCl$_3$): δ 8.07 (s, 1H), 2.49 (s, 3H), 2.22 (s, 3H), 2.20 (s, 3H), 2.19 (s, 3H); $^{13}$C{$^1$H}NMR (100 MHz, CDCl$_3$): δ 154.0, 146.3, 143.9, 129.4, 129.3, 23.2, 17.1, 15.4, 15.1.

2,5-Dimethyl-4-phenylpyridine (3y)

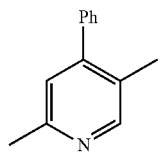

4-Phenyl-3-buten-2-one (1o, 88 mg, 0.60 mmol), propargylamine (2a, 49.5 mg, 0.90 mmol) and NaHCO$_3$ (101 mg, 1.20 mmol) in DMF (3 mL) were stirred for 3 h at room temperature followed by 12 h at 80° C. After column chromatography (EtOAc/hexanes 5:95 to 20:80), 82 mg (75%) of a pale, yellow liquid was obtained. R$_f$=0.4 (EtOAc/hexanes 30:70); $^1$H NMR (400 MHz, CDCl$_3$): δ 8.37 (s, 1H), 7.47-7.35 (m, 3H), 7.33-7.28 (m, 2H), 7.02 (s, 1H), 2.54 (s, 3H), 2.22 (s, 3H); $^{13}$C{$^1$H}NMR (100 MHz, CDCl$_3$): δ 155.6, 150.4, 149.5, 139.2, 128.4, 128.3, 127.7, 127.4, 123.5, 23.7, 16.7.

1,4-Dimethyl-6,7-dihydro-5H-cyclopenta[c]pyridine (3z)

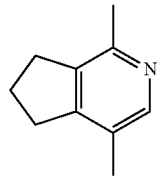

1-Acetylcyclopentene (1p, 66 mg, 0.60 mmol), propargylamine (2a, 49.5 mg, 0.90 mmol) and NaHCO$_3$ (101 mg, 1.20 mmol) in DMF (3 mL) were stirred for 3 h at room temperature followed by 12 h at 80° C. After column chromatography (Et$_2$O/hexanes 5:95 to 20:80) 130 mg (70%) of a pale, yellow liquid was obtained. R$_f$=0.3 (Et$_2$O/hexanes 30:70); $^1$H NMR (400 MHz, CDCl$_3$): δ 8.07 (s, 1H), 2.91-2.81 (m, 4H), 2.43 (s, 3H), 2.20 (s, 3H), 2.14-2.05 (m, 2H); $^{13}$C{$^1$H}NMR (100 MHz, CDCl$_3$): δ 152.2, 151.1, 146.8, 137.2, 126.8, 31.4, 30.9, 23.8, 21.7, 15.9; FTIR (neat): 2920, 1669, 1596, 1434, 1312, 1045, 926, 906, 722 cm$^{-1}$; MS (ESI): m/z 148 (M+H)$^+$; HRMS (ESI): m/z calcd for C$_{10}$H$_{14}$N (M+H)$^+$: 148.1121, found: 148.1125.

(Z)—N—((E)-2-methylbut-2-en-1-ylidene)prop-2-yn-1-amine (3aa)

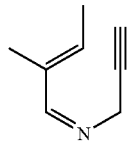

Tiglic aldehyde (1a, 50 mg, 0.60 mmol) and propargylamine (2a, 49.5 mg, 0.90 mmol) in DMF (3 mL) were stirred for 36 h at room temperature. After column chromatography (Et$_2$O/hexanes 5:95 to 10:80), 62 mg (85%) of a pale, yellow liquid was obtained. R$_f$=0.6 (Et$_2$O/hexanes 20:70); $^1$H NMR (400 MHz, CDCl$_3$): δ 8.08 (t, J=1.5 Hz, 1H), 6.26-5.86 (m, 1H), 4.36 (dd, J=2.5, 1.5 Hz, 2H), 2.44 (t, J=2.5 Hz, 1H), 1.86 (d, J=5.5 Hz, 3H), 1.85 (s, 3H); $^{13}$C{$^1$H}NMR (100 MHz, CDCl$_3$): δ 167.0, 137.5, 136.5, 79.6, 74.6, 46.7, 14.2, 11.1; FTIR (neat): 3010, 2919, 1630, 1423, 1298, 1125, 1013, 978, 847, 726 cm$^{-1}$; MS (ESI): m/z 122 (M+H)$^+$.

(S)-4-Methyl-6-(prop-1-en-2-yl)-5,6,7,8-tetrahydroisoquinoline (4a)

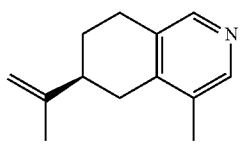

(S)—(—)—Perillaldehyde (1q, 90 mg, 0.60 mmol), propargylamine (2a, 49.5 mg, 0.90 mmol) and NaHCO$_3$ (101 mg, 1.20 mmol) in DMF (3 mL) were stirred for 3 h at room temperature followed by 12 h at 80° C. After column chromatography (EtOAc/hexanes 5:95 to 30:70), 95 mg (85%) of a brown liquid was obtained. R$_f$=0.2 (EtOAc/hexanes 30:70); [α]$_D^{25}$=−37.8 (c=0.53, CHCl$_3$); $^1$H NMR (400 MHz, CDCl$_3$) δ 8.18 (s, 1H), 8.15 (s, 1H), 4.83-4.80 (m, 1H), 4.79-4.76 (m, 1H), 2.92-2.70 (m, 3H), 2.51-2.32 (m, 2H), 2.19 (s, 3H), 2.06-1.97 (m, 1H), 1.82 (s, 3H), 1.68-1.54 (m, 1H); $^{13}$C{$^1$H}NMR (100 MHz, CDCl$_3$): δ 148.8, 147.9, 147.2, 144.1, 131.5, 131.3, 109.6, 41.1, 31.5, 27.1, 26.6, 20.6, 16.0; FTIR (neat): 2923, 1644, 1586, 1435, 1376, 1149, 1034, 886, 720 cm$^{-1}$; MS (ESI): m/z 188 (M+H)$^+$; HRMS (ESI): m/z calcd for C$_{13}$H$_{18}$N (M+H)$^+$: 188.1434, found: 188.1436.

(6R,8R)-4,7,7-Trimethyl-5,6,7,8-tetrahydro-6,8-methanoisoquinoline (4b)

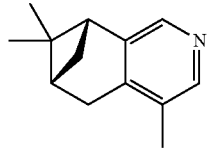

(1R)—(−)—Myrtenal (1r, 90 mg, 0.60 mmol), propargylamine (2a, 49.5 mg, 0.90 mmol) and NaHCO$_3$ (101 mg, 1.20 mmol) in DMF (3 mL) were stirred for 3 h at room temperature followed by 12 h at 80° C. After column chromatography (EtOAc/hexanes 5:95 to 30:70), 91 mg (81%) of a brown liquid was obtained. R$_f$=0.2 (EtOAc/hexanes 30:70); [α]$_D^{25}$−34.7 (c 1.12, CHCl$_3$); $^1$H NMR (400 MHz, CDCl$_3$): δ 8.22 (s, 1H), 7.99 (s, 1H), 2.88-2.72 (m, 3H), 2.66 (dt, J=9.7, 5.8 Hz, 1H), 2.34 (dq, J=8.7, 2.8 Hz, 1H), 2.20 (s, 3H), 1.40 (s, 3H), 1.18 (d, J=9.5 Hz, 1H), 0.60 (s, 3H); $^{13}$C{$^1$H}NMR (100 MHz, CDCl$_3$): δ 148.5, 143.8, 142.4, 141.5, 131.0, 44.4, 39.9, 38.7, 31.6, 31.3, 25.8, 21.2, 15.2; FTIR (neat): 2921, 1588, 1472, 1424, 1289, 1221, 1132, 955, 844, 792, 735 cm$^{-1}$; MS (ESI): m/z 188 (M+H)$^+$; HRMS (ESI): m/z calcd for C$_{13}$H$_{18}$N (M+H)$^+$: 188.1434, found: 188.1437.

(R)-4,7-Dimethyl-6,7-dihydro-5H-cyclopenta[c]pyridine ((−)-actinidine) (5)

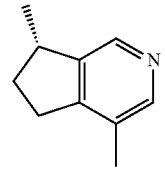

(R)-5-Methylcyclopent-1-enecarbaldehyde (1s, 66 mg, 0.60 mmol), propargylamine (2a, 49.5 mg, 0.90 mmol) and NaHCO$_3$ (101 mg, 1.20 mmol) in DMF (3 mL) were stirred for 3 h at room temperature followed by 12 h at 80° C. After column chromatography (Et$_2$O/hexanes 05:95 to 20:80), 73 mg (85%) of a pale, yellow liquid was obtained. R$_f$=0.3 (Et$_2$O/hexanes 30:70); [α]$_D^{25}$−14.6 (c 0.2, CHCl$_3$); $^1$H NMR (400 MHz, CDCl$_3$): δ 8.26 (s, 1H), 8.19 (s, 1H), 3.34-3.16 (m, 1H), 2.86 (ddd, J=16.7, 8.8, 4.1 Hz, 1H), 2.73 (dt, J=16.7, 8.3 Hz, 1H), 2.42-2.29 (m, 1H), 2.24 (s, 3H), 1.62 (ddd, J=16.7, 12.7, 8.3 Hz, 1H), 1.31 (d, J=6.9 Hz, 3H); $^{13}$C{$^1$H}NMR (100 MHz, CDCl$_3$): δ 151.9, 147.7, 143.6, 142.5, 129.1, 37.9, 33.8, 29.7, 20.0, 16.0;

REFERENCES

1. Baiceanu, E.; Nguyen, K. A.; Gonzalez-Lobato, L.; Nasr, R.; Baubichon-Cortay, H.; Loghin, F.; Le Borgne, M.; Chow, L.; Boumendjel, A.; Peuchmaur, M.; Falson, P., Eur. J. Med. Chem. 2016, 122, 408-418.
2. Lu, W.; Xin, X.; Yuanhong, L., Angew. Chem. Int. Ed. 2013, 52, 13302-13306.
3. Carlier, P. R.; Lam, P. C. H.; Wong, D. M., J. Org. Chem. 2002, 67, 6256-6259.
4. Zhang, Y. Y.; Wei, Y.; Tang, X. Y.; Shi, M., Chem. Comm. 2017, 53, 5966-5969.
5. (a) Jouha, J.; Buttard, F.; Lorion, M.; Berthonneau, C.; Khouili, M.; Hiebel, M. A.; Guillaumet, G.; Brière, J. F.; Suzenet, F., Org. Lett. 2017, 19, 4770-4773; (b) Qiaoyi, W.; E., M. S.; G., A. N.; L., P. J.; Xiaodong, S., Angew. Chem. Int. Ed. 2014, 53, 5418-5422.
6. Shanmugam, S.; Ashish, S.; Rengarajan, B., Eur. J. Org. Chem. 2017, 2017, 3941-3946.
7. Song, H.; Liu, Y.; Wang, Q., Org. Lett. 2013, 15, 3274-3277.
8. Kolleth, A.; Christoph, S.; Arseniyadis, S.; Cossy, J., Chem. Comm. 2012, 48, 10511-10513.
9. Kiran, M.; P., A. A., Angew. Chem. Int. Ed. 2013, 52, 2082-2086.
10. T. T. Wang, L. Zhao, Y. J. Zhang and W. W. Liao, Org Lett, 2016, 18, 5002-5005.
11. L. Candish and D. W. Lupton, Org Biomol Chem, 2011, 9, 8182-8189.
12. (a) J. Jouha, F. Buttard, M. Lorion, C. Berthonneau, M. Khouili, M. A. Hiebel, G. Guillaumet, J. F. Brière and F. Suzenet, Org Lett, 2017, 19, 4770-4773; (b) Q. Wang, S. E. Motika, N. G. Akhmedov, J. L. Petersen and X. Shi, Angew Chem Int Ed Engl, 2014, 53, 5418-5422.
13. X. Zhou, Z. Jiang, L. Xue, P. Lu and Y. Wang, E J Org Chem, 2015, 2015, 5789-5797.
14. S. Sakthivel, A. Sharma and R. Balamurugan, E J Org Chem, 2017, 2017, 3941-3946.
15. Y. Fukumoto, M. Hirano and N. Chatani, ACS Catalysis, 2017, 7, 3152-3156.
16. M. Boruah and D. Konwar, Synlett, 2001, 2001, 0795-0796.
17. S. Chiba, Y. J. Xu and Y. F. Wang, J Am Chem Soc, 2009, 131, 12886-12887.
18. D. Xue, Z. H. Jia, C. J. Zhao, Y. Y. Zhang, C. Wang and J. Xiao, Chem Eur J, 2014, 20, 2960-2965.
19. M. J. Shiao, C. J. Peng, J. S. Wang and Y. T. Ma, J Chin Chem Soc, 1992, 39, 173-176.
20. C. Siv, G. Vernin and J. Metzger, Helv Chim Acta, 1979, 62, 1570-1585.
21. D. A. Colby, R. G. Bergman and J. A. Ellman, J Am Chem Soc, 2008, 130, 3645-3651.
22. H. Wei, Y. Li, K. Xiao, B. Cheng, H. Wang, L. Hu and H. Zhai, Org Lett, 2015, 17, 5974-5977.
23. J. S. Beckett, J. D. Beckett and J. E. Hofferberth, Org Lett, 2010, 12, 1408-1411.

INCORPORATION BY REFERENCE

The entire contents of all patents, published patent applications and other references cited herein are hereby expressly incorporated herein in their entireties by reference.

EQUIVALENTS

Those skilled in the art will recognize, or be able to ascertain using no more than routine experimentation, numerous equivalents to the specific procedures described herein. Such equivalents were considered to be within the scope of this invention and are covered by the following claims. Moreover, any numerical or alphabetical ranges provided herein are intended to include both the upper and lower value of those ranges. In addition, any listing or grouping is intended, at least in one embodiment, to represent a shorthand or convenient manner of listing independent embodiments; as such, each member of the list should be considered a separate embodiment.

What is claimed is:
1. A method of preparation of a substituted pyridine of formula I:

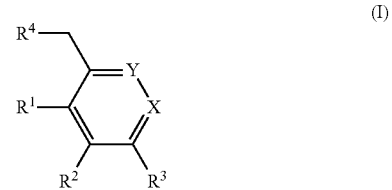

wherein
R$^1$ is selected from the group consisting of H, (C$_1$-C$_4$) alkyl, (C$_2$-C$_{10}$)alkenyl, indolylalkyl, aryl, and heteroaryl, each of which may be optionally substituted with 1 to 5 substituents selected from the group consisting of (C$_1$-C$_4$)haloalkyl, (C$_1$-C$_4$)alkoxy, —CN, halogen, NO$_2$, (C$_1$-C$_4$)alkyl and OH;
R$^2$ is selected from the group consisting of H and (C$_1$-C$_4$)alkyl; or R$^1$ and R$^2$ may be taken together with the carbons to which they are attached to form a ring structure selected from the group consisting of cycloalkyl, heterocyclyl, aryl, and heteroaryl, each of which may be optionally substituted with 1 to 3 substituents selected from the group consisting of (C$_1$-C$_4$)haloalkyl, (C$_1$-C$_4$)alkoxy, —CN, halogen, NO$_2$, (C$_1$-C$_4$)alkyl, (C$_2$-C$_4$)alkenyl, and OH;
R$^3$ is selected from the group consisting of H, (C$_1$-C$_4$) alkyl, and benzyl;
R$^4$ is selected from the group consisting of H, —CH$_2$, (C$_1$-C$_{10}$)alkyl, (C$_2$-C$_{10}$)alkenyl, indolylalkyl, aryl, and heteroaryl each of which is optionally substituted with 1 to 4 substituents selected from the group consisting of (C$_1$-C$_4$)alkyl, (C$_1$-C$_4$)haloalkyl, (C$_1$-C$_4$)alkoxy, halogen, —CN, NO$_2$, —C(O)O—(C$_1$-C$_4$)alkyl, —C(O)(C$_1$-C$_4$)alkyl, —O—(C$_1$-C$_4$)alkyl, and OH; and
X is N and Y is CR$_5$, wherein R$_5$ is H or (C$_1$-C$_4$)alkyl, comprising the step of single phase addition of an α,β-unsaturated carbonyl to a propargyl amine under metal-free conditions (MFC) wherein the metal-free conditions (MFC) comprise a mild base, with the proviso that the compound of formula (I) is not:

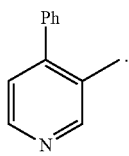

2. The method of claim 1, wherein the metal-free conditions (MFC) comprise a mild base held at less than or equal to 100° C.

3. The method of claim 2, wherein the mild base is selected from the group consisting of $K_2CO_3$, $NaHCO_3$, NaOAc, $CsCO_3$, $K_2HPO_4$, and DBU.

4. The method of claim 2, wherein the mild base is $NaHCO_3$.

5. The method of claim 1, wherein the method produces yields of greater than 80%.

6. The method of claim 1, wherein the mild base addition is performed in DMF.

7. The method of claim 1, wherein the α,β-unsaturated carbonyl is a compound of formula II:

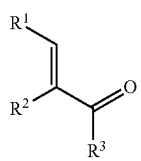

(II)

wherein
$R^1$ is selected from the group consisting of H, $(C_1-C_4)$ alkyl, $(C_2-C_{10})$alkenyl indolylalkyl, aryl, and heteroaryl, each of which may be optionally substituted with 1 to 5 substituents selected from the group consisting of $(C_1-C_4)$haloalkyl, $(C_1-C_4)$alkoxy, —CN, halogen, $NO_2$, $(C_1-C_4)$alkyl and OH;
$R^2$ is selected from the group consisting of H and $(C_1-C_4)$alkyl; or $R^1$ and $R^2$ may be taken together with the carbons to which they are attached to form a ring structure selected from the group consisting of cycloalkyl, heterocyclyl, aryl, and heteroaryl, each of which may be optionally substituted with 1 to 3 substituents selected from the group consisting of $(C_1-C_4)$haloalkyl, $(C_1-C_4)$alkoxy, —CN, halogen, $NO_2$, $(C_1-C_4)$alkyl, $(C_2-C_4)$alkenyl, and OH; and
$R^3$ is selected from the group consisting of H, $(C_1-C_4)$ alkyl, and benzyl.

8. The method of claim 1, wherein the propargyl amine is a compound of formula III:

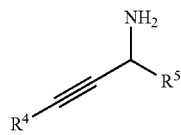

(III)

wherein
$R^4$ is selected from the group consisting of H, $—CH_2$, $(C_1-C_{10})$alkyl, $(C_2-C_{10})$alkenyl indolylalkyl, aryl, and heteroaryl each of which is optionally substituted with 1 to 4 substituents selected from the group consisting of $(C_1-C_4)$alkyl, $(C_1-C_4)$haloalkyl, $(C_1-C_4)$alkoxy, halogen, —CN, $NO_2$, —C(O)O—$(C_1-C_4)$alkyl, —C(O)$(C_1-C_4)$alkyl, —O—$(C_1-C_4)$alkyl, and OH; and
$R_5$ is H or $(C_1-C_4)$alkyl.

9. The method of claim 1, wherein the compound of formula (I) is selected from a compound of formula (IV):

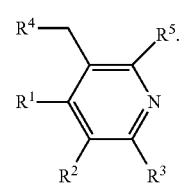

(IV)

10. The method of claim 1, wherein the compound of formula (I) is selected from a compound of formula (V):

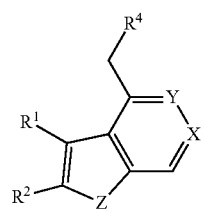

(V)

wherein
Z is selected from the group consisting of —O—, —S—, —N($R_6$)—, wherein $R_6$ is H, $(C_1-C_4)$alkyl, tosyl, benzyl, phenyl, tert-butyloxycarbonyl.

11. The method of claim 1, wherein the compound of formula (I) is selected from a compound of formula (VI):

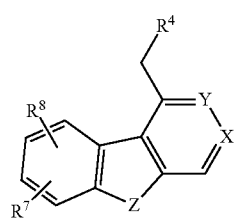

(VI)

wherein
Z is selected from the group consisting of —O—, —S—, —N($R_6$)—, wherein $R_6$ is H, $(C_1-C_4)$alkyl, tosyl, benzyl, phenyl, tert-butyloxycarbonyl; and
$R^7$ and $R^8$ are each independently selected from the group consisting of H, $(C_1-C_4)$haloalkyl, $(C_1-C_4)$alkoxy, —CN, halogen, $NO_2$, $(C_1-C_4)$alkyl, $(C_2-C_4)$alkenyl, and OH.

* * * * *